United States Patent
Yoo et al.

(10) Patent No.: US 10,669,282 B2
(45) Date of Patent: Jun. 2, 2020

(54) METHOD FOR SYNTHESIZING 3-PHENYL-2,3,4,8,9,10-HEXAHYDRO PYRANO[2.3-F]CHROMENE DERIVATIVE AND OPTICAL ISOMER OF THEREOF

(71) Applicant: GLACEUM, INC., Suwon-si, Gyeonggi-do (KR)

(72) Inventors: Sang Ku Yoo, Suwon-si (KR); Jin Wook Chung, Seoul (KR); In Geun Jo, Cheonan-si (KR); Ji Young Kim, Seoul (KR); Jeong Ho Im, Gwangju-si (KR); Ku Suk Kang, Yongin-si (KR); Jin Young Kim, Suwon-si (KR)

(73) Assignee: GLACEUM, INC., Suwon-si, Gyeonggi-do (KR)

( * ) Notice: Subject to any disclaimer, the term of this patent is extended or adjusted under 35 U.S.C. 154(b) by 0 days.

(21) Appl. No.: 16/339,288

(22) PCT Filed: Sep. 27, 2017

(86) PCT No.: PCT/KR2017/010679
§ 371 (c)(1),
(2) Date: Apr. 3, 2019

(87) PCT Pub. No.: WO2018/066872
PCT Pub. Date: Apr. 12, 2018

(65) Prior Publication Data
US 2020/0048272 A1 Feb. 13, 2020

(30) Foreign Application Priority Data

Oct. 4, 2016 (KR) ........................ 10-2016-0127805

(51) Int. Cl.
*C07D 493/04* (2006.01)
*C07D 311/04* (2006.01)

(52) U.S. Cl.
CPC .......... *C07D 493/04* (2013.01); *C07D 311/04* (2013.01); *C07B 2200/07* (2013.01)

(58) Field of Classification Search
None
See application file for complete search history.

(56) References Cited

U.S. PATENT DOCUMENTS

2016/0272650 A1   9/2016   Yoo et al.

FOREIGN PATENT DOCUMENTS

| CN | 103030647 | 4/2013 |
| JP | 2019520381 | 7/2019 |
| KR | 1020070052211 | 5/2007 |
| KR | 1020150075030 | 7/2015 |

OTHER PUBLICATIONS

Van Heerden et al. "Structure and Synthesis of Some Complex Pyranoisoflavonoids from the Bark of Dalbergia Nitidula Welw. ex Bak" Journal of the Chemical Society., Perkin Transactions 1, 2:137-145 (1978).
Yenesew et al. "The antiplasmodial and radical scavenging activities of flavonoids of Erythrina burttii" Acta Tropica 123(2):123-127 (2012).
Yenesew et al. "Three isoflav-3-enes and a 2-arylbenzofuran from the root bark of Erythrina burttii" Phytochemistry 59(3):337-341 (2002).
International Search Report of the International Searching Authority Corresponding to International Patent Application No. PCT/KR2017/010679, dated Jan. 8, 2018. (7 pages with English translation).
Yenesew et al. "Three isoflav-3-enes and a 2-arylbenzofuran from the root bark of Erythrina burttii" Phytochemistry 59(3):337-341 (2002). Abstract Only.
Yenesew et al. "The antiplasmodial and radical scavenging activities of flavonoids of Erythrina burttii" Acta Tropica 123(2):123-127 (2012). Abstract Only.
Van Heerden et al. "Structure and Synthesis of Some Complex Pyranoisoflavonoids from the Bark of Dalbergia Nitidula Welw. ex Bak" Journal of the Chemical Society., Perkin Transactions 1, 2:137-145 (1978). Abstract Only.

*Primary Examiner* — Zinna Northington Davis
(74) *Attorney, Agent, or Firm* — Myers Bigel, P.A.

(57) ABSTRACT

The present invention relates to a method for synthesizing a 3-phenyl-2,3,4,8,9,10-hexahydropyrano[2,3-f]chromene derivative and an optical isomer thereof, and an intermediate Compound which may be used for the synthesis method, and when the method and the intermediate Compound are used, the 3-phenyl-2,3,4,8,9,10-hexahydropyrano[2,3-f]chromene derivative and the optical isomer thereof may be effectively synthesized.

17 Claims, No Drawings

METHOD FOR SYNTHESIZING 3-PHENYL-2,3,4,8,9,10-HEXAHYDRO PYRANO[2.3-F]CHROMENE DERIVATIVE AND OPTICAL ISOMER OF THEREOF

CROSS REFERENCE TO RELATED APPLICATIONS

This application is a 35 U.S.C. § 371 national stage application of PCT International Application No. PCT/KR2017/010679, filed Sep. 27, 2017, which claims priority from Korean Patent Application No. 10-2016-0127805, filed Oct. 4, 2016, the contents of which are incorporated herein in their entireties by reference. The above-referenced PCT International Application was published in the Korean language as International Publication No. WO 2018/066872 A1 on Apr. 12, 2018.

TECHNICAL FIELD

The present invention relates to a method for synthesizing a 3-phenyl-2,3,4,8,9,10-hexahydropyrano[2,3-f]chromene derivative and an optical isomer thereof, and an intermediate Compound which may be used for the method.

BACKGROUND ART

About 20 billion or more adipocytes are present in the human body, and when much more energy is supplied to the human body than the need for energy, energy is stored as triglyceride in adipocytes in the human body, and when energy is used up, the triglyceride is decomposed into free fatty acid and glucose and thus is used as an energy source. Obesity, which about 30 to 40% of modern people suffer from, occurs when excessive energy is accumulated due to the imbalance of the procedure, and is shown as a phenomenon in which the size of adipocytes is increased or the number thereof is increased.

The metabolic syndrome conceptualizes a clustering phenomenon of risk factors of various cardiovascular diseases and type 2 diabetes as one disease group. The metabolic syndrome is a concept which may comprehensively explain various metabolic abnormalities and clinical aspects, and refers to a syndrome in which risk factors such as obesity, diabetes, fatty liver, and hypertriglyceridemia are together increased. Accordingly, in the case of a metabolic syndrome, the risk of incidence of a cardiovascular disease or type 2 diabetes is increased.

Insulin resistance refers to a phenomenon in which, even though insulin is normally secreted in the body, a supply of glucose into cells, which is performed by insulin, does not work properly. Since glucose in the blood cannot enter cells, hyperglycemia is exhibited, and cells cannot perform normal functions thereof due to a shortage of glucose, and as a result, metabolic syndrome symptoms are manifested.

The diabetic symptom thus manifested is called type 2 diabetes (non-insulin-dependent diabetes mellitus: NIDDM) which is differentiated from type 1 diabetes (insulin-dependent diabetes mellitus) resulting from a shortage of insulin. For this reason, the most preferable method of treating type 2 diabetes is to induce insulin to be capable of performing normal functions thereof by alleviating insulin resistance. Nevertheless, a therapeutic agent of alleviating insulin resistance has hardly been developed up until now.

Most of the type 2 diabetes therapeutic agents currently used or developed aim to increase the amount of insulin secreted in order to supplement the functions of insulin lost by insulin resistance. However, when the amount of insulin secreted is increased from our bodies, not only obesity and inflammation are caused, but also various side effects such as an increase in cancer incidence rate are accompanied, so that unless the insulin resistance problem is alleviated, it is possible to expect that blood sugar is temporarily normalized, but the health is negatively influenced even more. For this reason, there is a more desperate social need for a type 2 diabetes therapeutic agent capable of normalizing blood sugar by alleviating insulin resistance.

Meanwhile, Patent Document 1 discloses that a pyranochromenyl phenol derivative is effective for preventing and treating a metabolic syndrome including hyperlipidemia, fatty liver, sugar metabolic abnormality, diabetes, and obesity, and have effects such as anti-inflammatory action.

Therefore, even though a method for efficiently and economically synthesizing the pyranochromenyl phenol derivative is very useful, a method for synthesizing the pyranochromenyl phenol derivative has been little known up until now, except for a method established based on a method for synthesizing (±)-glabridin (Non-Patent Document 1) developed by the present inventor.

REFERENCES OF THE RELATED ART

Patent Documents

1. Korean Patent Application Laid-Open No. 10-2015-0075030

Non-Patent Documents

1. Sang-Ku Yoo, Keepyung Nahm; Bull. Korean Chem. Soc. 2007 (28) 481~484

DETAILED DESCRIPTION OF THE INVENTION

Technical Problem

An object of the present invention is to provide a method for synthesizing a 3-phenyl-2,3,4,8,9,10-hexahydropyrano[2,3-f]chromene derivative and an optical isomer thereof, and a 3-phenyl-2,8-dihydropyrano[2,3-f]chromene derivative which may be used for the method.

Technical Solution

In order to accomplish the object, an aspect of the present invention provides a method for synthesizing a 3-phenyl-2,3,4,8,9,10-hexahydropyrano[2,3-f]chromene derivative of Chemical Formula (I), the method including:

a) coupling a Compound represented by Chemical Formula 1 with a Compound represented by Chemical Formula 2 to form a Compound of Chemical Formula 3;

b) reducing the Compound of Chemical Formula 3 to form a Compound of Chemical Formula 4; and c) cyclizing the Compound of Chemical Formula 4 to form a Compound of Chemical Formula 5:

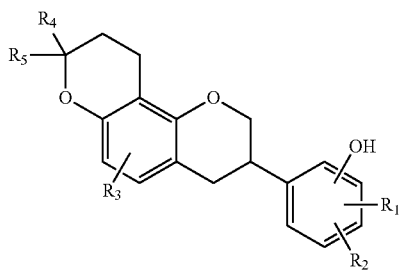

(I)

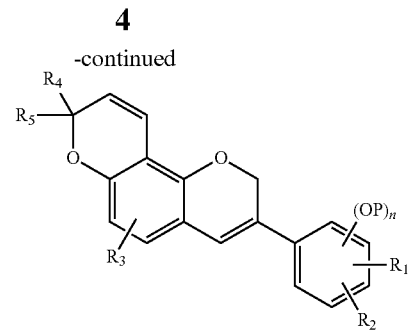

Chemical Formula 5

[Reaction Formula 1]

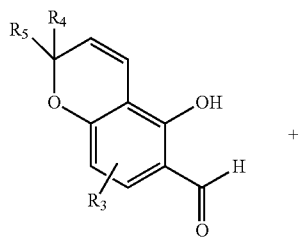

Chemical Formula 1

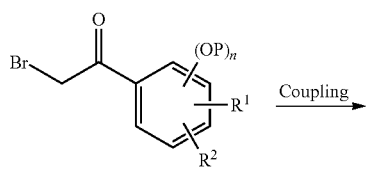

Chemical Formula 2

↓ Coupling

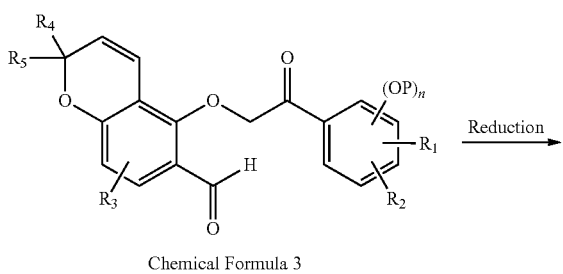

Chemical Formula 3

↓ Reduction

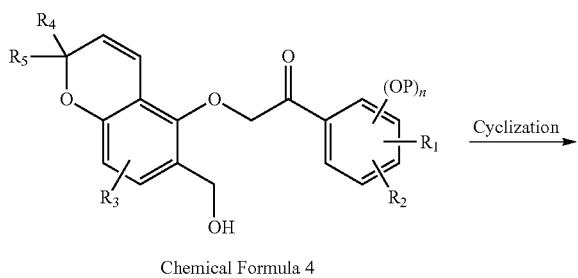

Chemical Formula 4

↓ Cyclization wherein, $R_1$ and $R_2$ are each independently hydrogen atom; hydroxy group; straight or branched $C_1$ to $C_6$ alkyl group unsubstituted or substituted with halogen atom, straight or branched $C_1$ to $C_5$ alkyl group, straight or branched $C_1$ to $C_5$ alkoxy group, or straight or branched $C_1$ to $C_3$ thioalkyl group; halogen atom; straight or branched $C_1$ to $C_6$ alkoxy group unsubstituted or substituted with halogen atom, straight or branched $C_1$ to $C_5$ alkyl group, straight or branched $C_1$ to $C_5$ alkoxy group, or straight or branched $C_1$ to $C_3$ thioalkyl group; straight or branched $C_1$ to $C_4$ thioalkyl group unsubstituted or substituted with halogen atom, straight or branched $C_1$ to $C_5$ alkyl group, straight or branched $C_1$ to $C_5$ alkoxy group, or straight or branched $C_1$ to $C_3$ thioalkyl group; allyloxy group unsubstituted or substituted with halogen atom, straight or branched $C_1$ to $C_5$ alkyl group, straight or branched $C_1$ to $C_5$ alkoxy group, or straight or branched $C_1$ to $C_3$ thioalkyl group; or aryloxy group unsubstituted or substituted with halogen atom, straight or branched $C_1$ to $C_5$ alkyl group, straight or branched $C_1$ to $C_5$ alkoxy group, or straight or branched $C_1$ to $C_3$ thioalkyl group;

$R_3$ is hydrogen atom or $C_1$ to $C_2$ alkyl group or $C_1$ to $C_2$ alkoxy group;

$R_4$ and $R_5$ are each independently hydrogen atom or $C_1$ to $C_6$ alkyl group;

P is a protecting group selected from straight or branched $C_1$ to $C_4$ alkyl group unsubstituted or substituted with halogen atom, straight or branched $C_1$ to $C_5$ alkyl group, straight or branched $C_1$ to $C_5$ alkoxy group, or straight or branched $C_1$ to $C_3$ thioalkyl group; benzyl group unsubstituted or substituted with halogen atom, straight or branched $C_1$ to $C_5$ alkyl group, straight or branched $C_1$ to $C_5$ alkoxy group, or straight or branched $C_1$ to $C_3$ thioalkyl group; allyl group unsubstituted or substituted with halogen atom, straight or branched $C_1$ to $C_5$ alkyl group, straight or branched $C_1$ to $C_5$ alkoxy group, or straight or branched $C_2$ to $C_3$ thioalkyl group; tert-butyldimethylsilyl group; tert-butyldiphenylsilyl group; methylphenylsilyl group; trimethylphenylsilyl group; $MeSO_2$ and $p\text{-}TsSO_2$;

n is 1 to 3; and two or more OPs are the same or different from each other.

Another aspect of the present invention provides a Compound represented by the following Chemical Formula 3 or a solvate thereof:

[Chemical Formula 3]

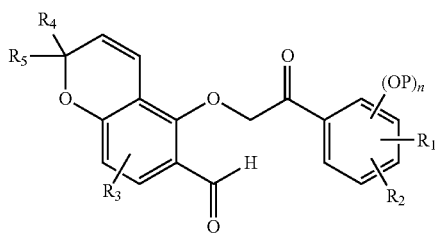

wherein, $R_1$ and $R_2$ are each independently hydrogen atom; hydroxy group; straight or branched $C_1$ to $C_6$ alkyl group unsubstituted or substituted with halogen atom, straight or branched $C_1$ to $C_5$ alkyl group, straight or branched $C_1$ to $C_5$ alkoxy group, or straight or branched $C_1$ to $C_3$ thioalkyl group; halogen atom; straight or branched $C_1$ to $C_6$ alkoxy group unsubstituted or substituted with halogen atom, straight or branched $C_1$ to $C_5$ alkyl group, straight or branched $C_1$ to $C_5$ alkoxy group, or straight or branched $C_1$ to $C_3$ thioalkyl group; straight or branched $C_1$ to $C_4$ thioalkyl group unsubstituted or substituted with halogen atom, straight or branched $C_1$ to $C_5$ alkyl group, straight or branched $C_1$ to $C_5$ alkoxy group, or straight or branched $C_1$ to $C_3$ thioalkyl group; allyloxy group unsubstituted or substituted with halogen atom, straight or branched $C_1$ to $C_5$ alkyl group, straight or branched $C_1$ to $C_5$ alkoxy group, or straight or branched $C_1$ to $C_3$ thioalkyl group; or aryloxy group unsubstituted or substituted with halogen atom, straight or branched $C_1$ to $C_5$ alkyl group, straight or branched $C_1$ to $C_5$ alkoxy group, or straight or branched $C_1$ to $C_3$ thioalkyl group;

$R_3$ is hydrogen atom or $C_1$ to $C_2$ alkyl group or $C_1$ to $C_2$ alkoxy group;

$R_4$ and $R_5$ are each independently hydrogen atom or $C_1$ to $C_6$ alkyl group;

P is a protecting group selected from straight or branched $C_1$ to $C_4$ alkyl group unsubstituted or substituted with halogen atom, straight or branched $C_1$ to $C_5$ alkyl group, straight or branched $C_1$ to $C_5$ alkoxy group, or straight or branched $C_1$ to $C_3$ thioalkyl group; benzyl group unsubstituted or substituted with halogen atom, straight or branched $C_1$ to $C_5$ alkyl group, straight or branched $C_1$ to $C_5$ alkoxy group, or straight or branched $C_1$ to $C_3$ thioalkyl group; allyl group unsubstituted or substituted with halogen atom, straight or branched $C_1$ to $C_5$ alkyl group, straight or branched $C_1$ to $C_5$ alkoxy group, or straight or branched $C_1$ to $C_3$ thioalkyl group; tert-butyldimethylsilyl group; tert-butyldiphenylsilyl group; methylphenylsilyl group; trimethylphenylsilyl group; $MeSO_2$ and $p$-$TsSO_2$;

n is 1 to 3; and two or more OPs are the same or different from each other.

Further, still another aspect of the present invention provides a Compound represented by the following Chemical Formula 4 or a solvate thereof:

[Chemical Formula 4]

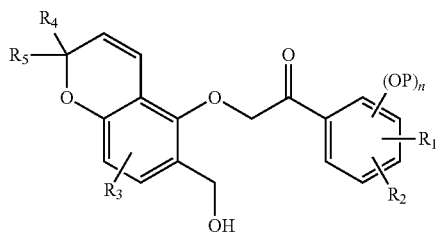

$R_1$ to $R_5$, P, and n in Chemical Formula 4 are the same as those defined in Chemical Formula 3.

Further, yet another aspect of the present invention provides a 3-phenyl-2,8-dihydropyrano[2,3-f]chromene Compound represented by the following Chemical Formula 5 or a solvate thereof:

[Chemical Formula 5]

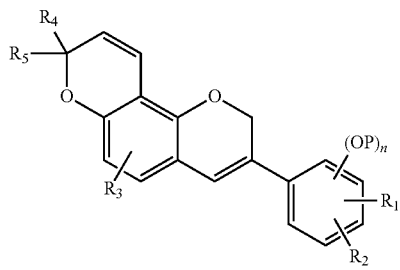

$R_1$ to $R_5$, P, and n in Chemical Formula 5 are the same as those defined in Chemical Formula 3.

In addition, still yet another aspect of the present invention provides a method for synthesizing an optical isomer of a 3-phenyl-2,3,4,8,9,10-hexahydropyrano[2,3-f]chromene derivative of Chemical Formula (I), the method including:

A) coupling a Compound represented by Chemical Formula 1 with a Compound represented by Chemical Formula 2 to form a Compound of Chemical Formula 3;

B) reducing the Compound of Chemical Formula 3 to form a Compound of Chemical Formula 4;

C) cyclizing the Compound of Chemical Formula 4 to form a Compound of Chemical Formula 5; and D) subjecting the Compound represented by Chemical Formula 5 to an asymmetric hydrogenation reaction to form an optical isomer Compound of Chemical Formula 6a (R-form) or 6b (S-form):

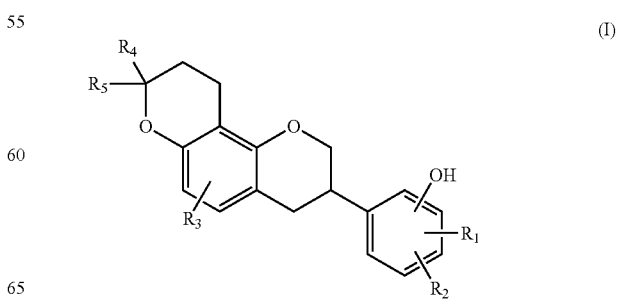

(I)

[Reaction Formula 2]

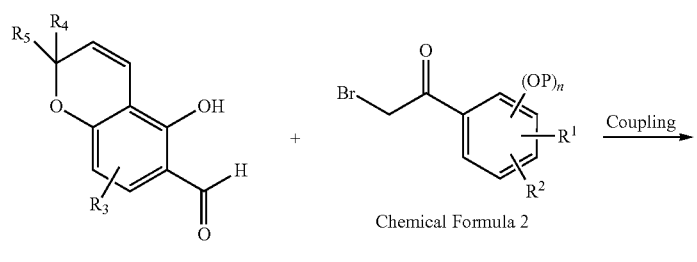

Chemical Formula 1    Chemical Formula 2

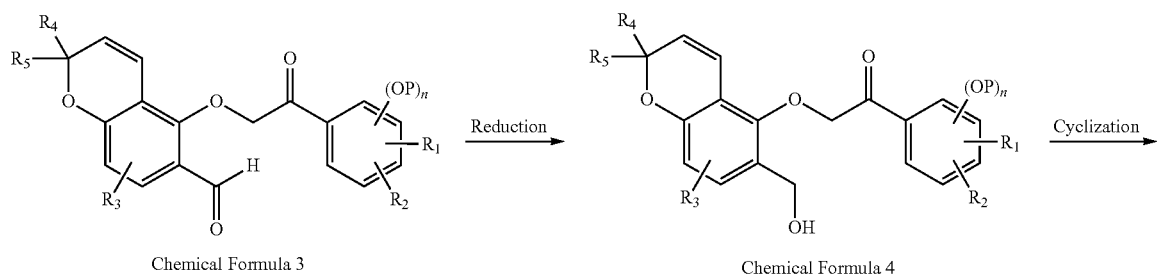

Chemical Formula 3    Chemical Formula 4

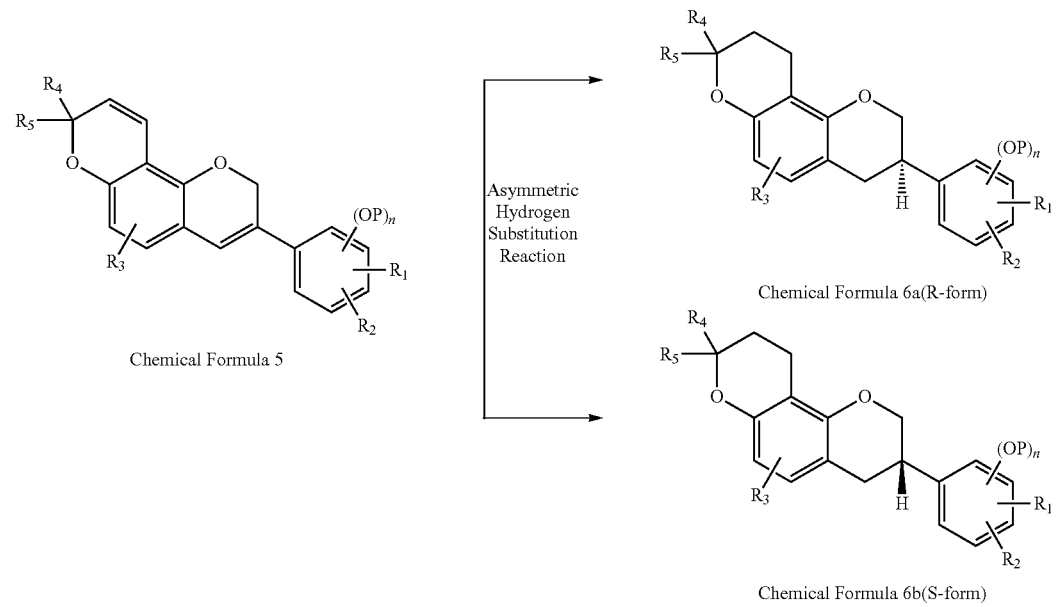

Chemical Formula 5

Chemical Formula 6a(R-form)

Chemical Formula 6b(S-form)

$R_1$ to $R_5$, P, and n in the chemical formulae are the same as those defined in Reaction Formula 1.

Furthermore, a further aspect of the present invention provides an optical isomer Compound represented by the following Chemical Formula 6a (R-form) or 6b (S-form) or a solvate thereof:

[Chemical Formula 6a]

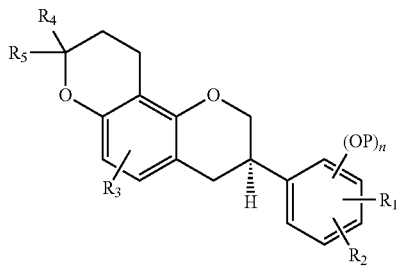

[Chemical Formula 6b]

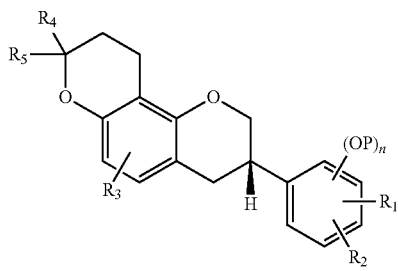

$R_1$ to $R_5$, P, and n in Chemical Formula 6a or 6b are the same as those defined in Chemical Formula 3.

Advantageous Effects

According to a synthesizing method of the present invention, it is possible to effectively synthesize a 3-phenyl-2,3,4,8,9,10-hexahydropyrano[2,3-f]chromene derivative and an optical isomer thereof by using the 3-phenyl-2,8-dihydropyrano[2,3-f]chromene derivative.

MODE FOR INVENTION

Hereinafter, the present invention will be described in more detail.

All the technical terms used in the present invention are used in the same sense as those generally understood by the person skilled in the related art of the present invention, unless otherwise defined. Further, in the present specification, a preferred method or sample is described, but those similar or equivalent thereto also fall within the scope of the present invention. The contents of all the publications described as a reference document in the present specification are incorporated into the present specification by reference.

An aspect of the present invention provides a method for synthesizing a 3-phenyl-2,3,4,8,9,10-hexahydropyrano[2,3-f]chromene derivative of Chemical Formula (I), the method including:

a) coupling a Compound represented by Chemical Formula 1 with a Compound represented by Chemical Formula 2 to form a Compound of Chemical Formula 3;

b) reducing the Compound of Chemical Formula 3 to form a Compound of Chemical Formula 4; and c) cyclizing the Compound of Chemical Formula 4 to form a Compound of Chemical Formula 5:

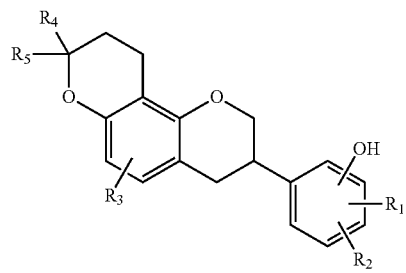

(I)

[Reaction Formula 1]

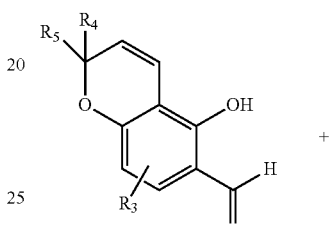

Chemical Formula 1

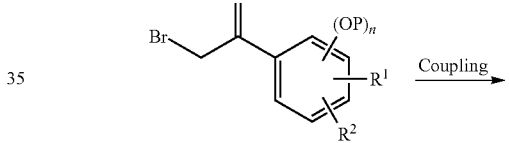

Chemical Formula 2

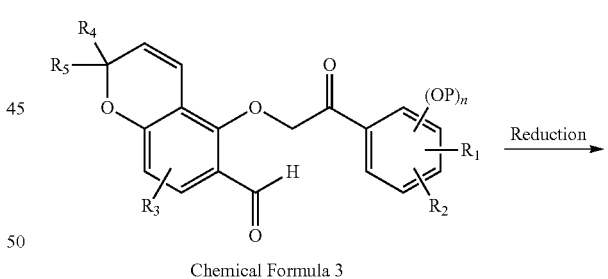

Chemical Formula 3

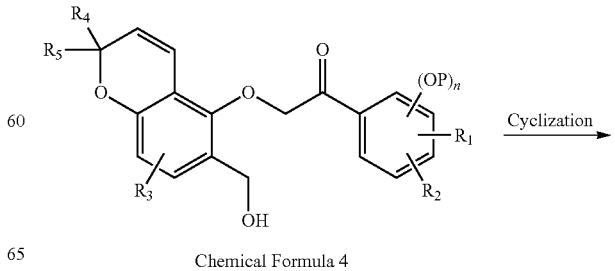

Chemical Formula 4

-continued

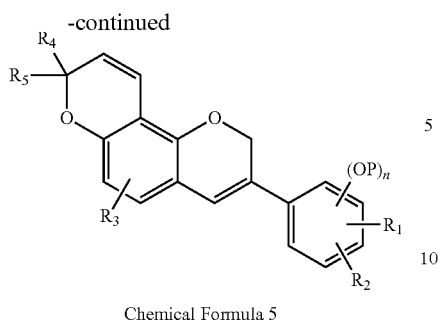

Chemical Formula 5 wherein,

R₁ and R₂ are each independently hydrogen atom; hydroxy group; straight or branched $C_1$ to $C_6$ alkyl group unsubstituted or substituted with halogen atom, straight or branched $C_1$ to $C_5$ alkyl group, straight or branched $C_1$ to $C_5$ alkoxy group, or straight or branched $C_1$ to $C_3$ thioalkyl group; halogen atom; straight or branched $C_1$ to $C_6$ alkoxy group unsubstituted or substituted with halogen atom, straight or branched $C_1$ to $C_5$ alkyl group, straight or branched $C_1$ to $C_5$ alkoxy group, or straight or branched $C_1$ to $C_3$ thioalkyl group; straight or branched $C_1$ to $C_4$ thioalkyl group unsubstituted or substituted with halogen atom, straight or branched $C_1$ to $C_5$ alkyl group, straight or branched $C_1$ to $C_5$ alkoxy group, or straight or branched $C_1$ to $C_3$ thioalkyl group; allyloxy group unsubstituted or substituted with halogen atom, straight or branched $C_1$ to $C_5$ alkyl group, straight or branched $C_1$ to $C_5$ alkoxy group, or straight or branched $C_1$ to $C_3$ thioalkyl group; or aryloxy group unsubstituted or substituted with halogen atom, straight or branched $C_1$ to $C_5$ alkyl group, straight or branched $C_1$ to $C_5$ alkoxy group, or straight or branched $C_1$ to $C_3$ thioalkyl group;

R₃ is hydrogen atom or $C_1$ to $C_2$ alkyl group or $C_1$ to $C_2$ alkoxy group;

R₄ and R₅ are each independently hydrogen atom or $C_1$ to $C_6$ alkyl group;

P is a protecting group selected from straight or branched $C_1$ to $C_4$ alkyl group unsubstituted or substituted with halogen atom, straight or branched $C_1$ to $C_5$ alkyl group, straight or branched $C_1$ to $C_5$ alkoxy group, or straight or branched $C_1$ to $C_3$ thioalkyl group; benzyl group unsubstituted or substituted with halogen atom, straight or branched $C_1$ to $C_5$ alkyl group, straight or branched $C_1$ to $C_5$ alkoxy group, or straight or branched $C_1$ to $C_3$ thioalkyl group; allyl group unsubstituted or substituted with halogen atom, straight or branched $C_1$ to $C_5$ alkyl group, straight or branched $C_1$ to $C_5$ alkoxy group, or straight or branched $C_1$ to $C_3$ thioalkyl group; tert-butyldimethylsilyl group; tert-butyldiphenylsilyl group; methylphenylsilyl group; trimethylphenylsilyl group; $MeSO_2$ and p-$TsSO_2$;

n is 1 to 3; and two or more OPs are the same or different from each other.

According to an exemplary embodiment of the present invention, the method for synthesizing a 3-phenyl-2,3,4,8,9,10-hexahydropyrano[2,3-f]chromene derivative of Chemical Formula (I) may further include a process of reducing the Compound of Chemical Formula 5. Specifically, through two hydrogen addition reactions and one de-protecting group process, it is possible to effectively synthesize a 3-phenyl-2,3,4,8,9,10-hexahydropyrano[2,3-f]chromene derivative of Chemical Formula (I), which is a pyranochromenyl phenol derivative having excellent anti-obese, anti-diabetic, and anti-inflammatory efficacies.

Examples of the 3-phenyl-2,3,4,8,9,10-hexahydropyrano[2,3-f]chromene derivative of Chemical Formula (I) include the following Compounds:

<Compound I-1>

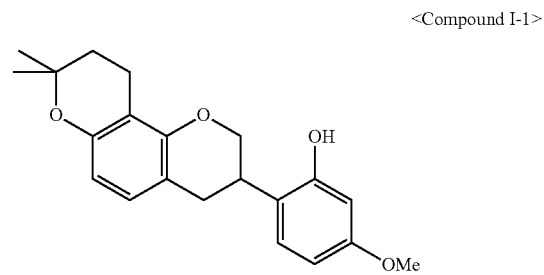

<Compound I-2>

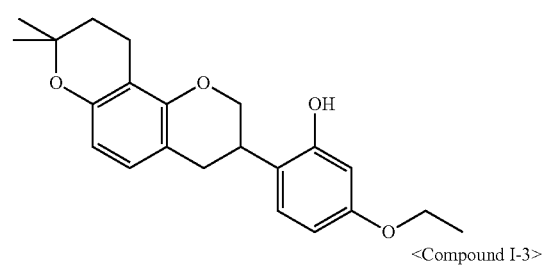

<Compound I-3>

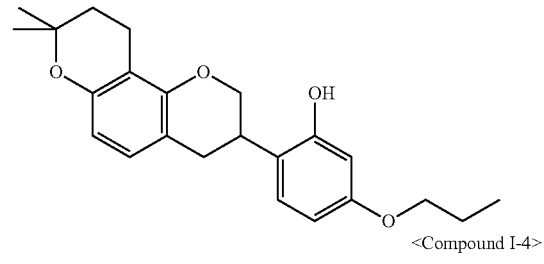

<Compound I-4>

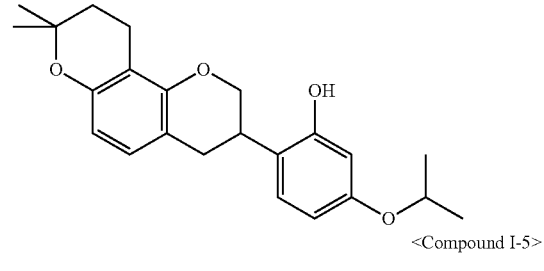

<Compound I-5>

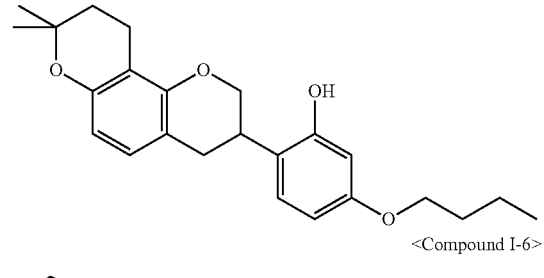

<Compound I-6>

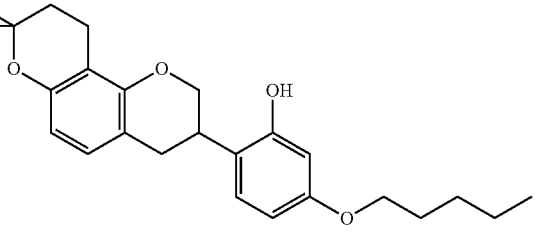

<Compound I-7>
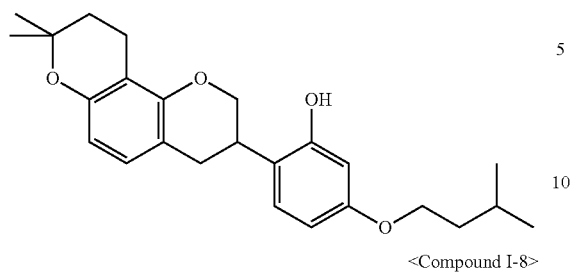
<Compound I-8>
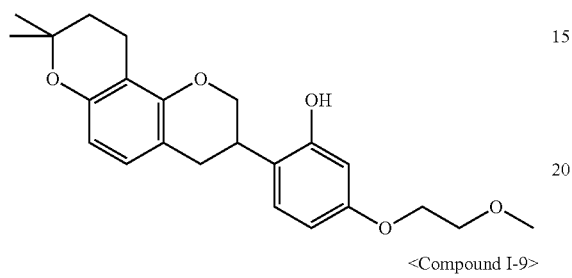
<Compound I-9>
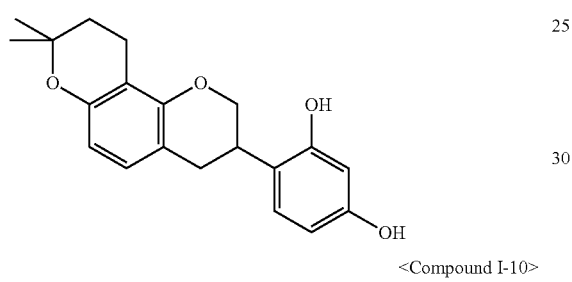
<Compound I-10>
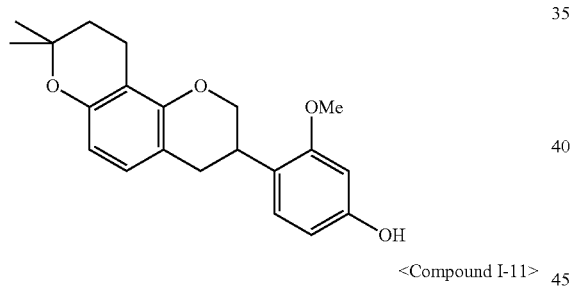
<Compound I-11>
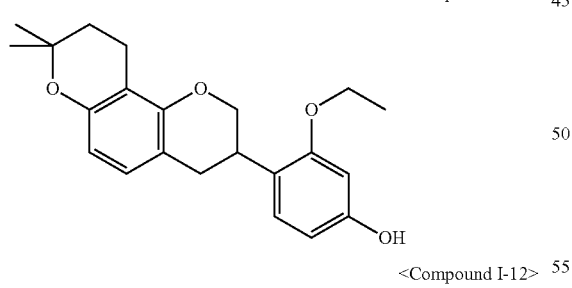
<Compound I-12>
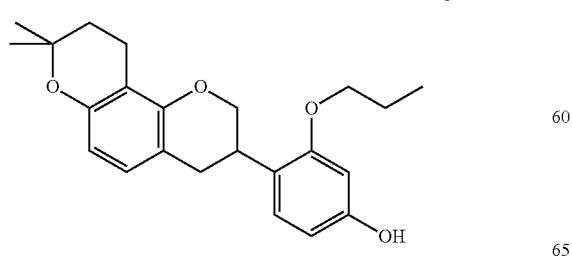
<Compound I-13>
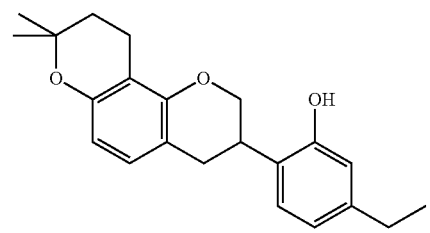
<Compound I-14>
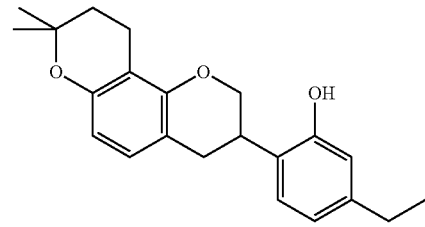
<Compound I-15>
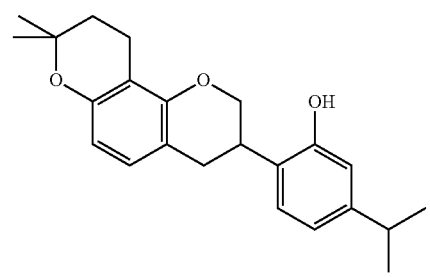
<Compound I-16>
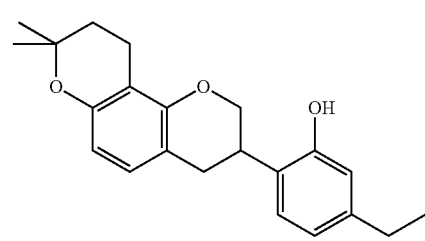
<Compound I-17>
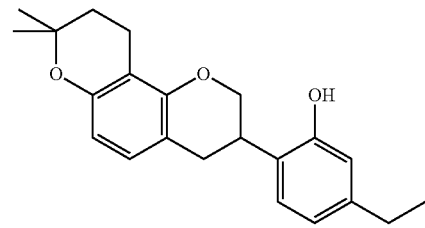
<Compound I-18>

<Compound I-19>
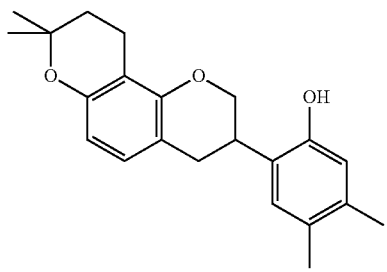
<Compound I-20>
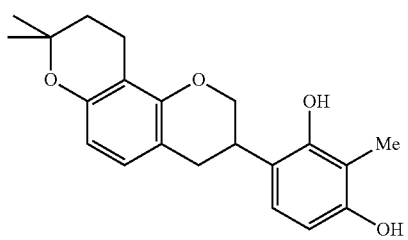
<Compound I-21>
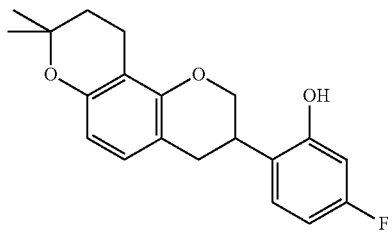
<Compound I-22>
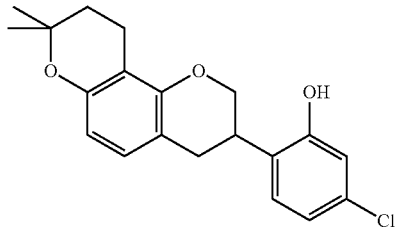
<Compound I-23>
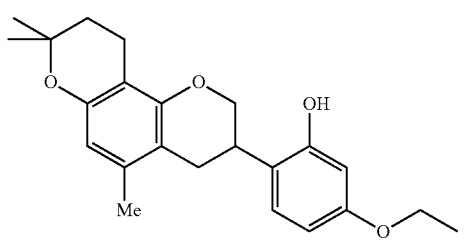
<Compound I-24>
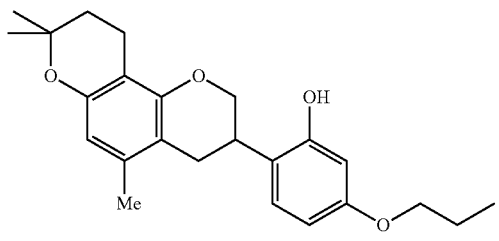
<Compound I-25>
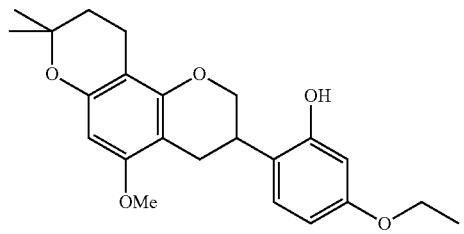
<Compound I-26>
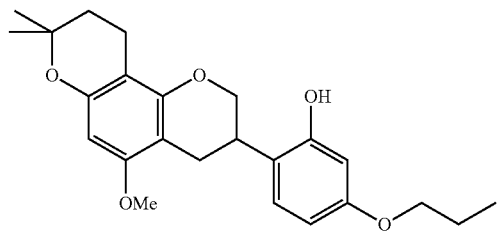
<Compound I-27>
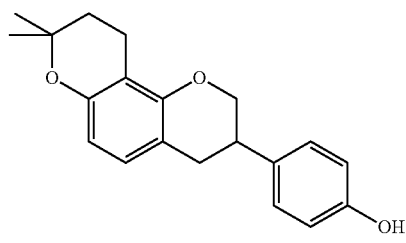
<Compound I-28>
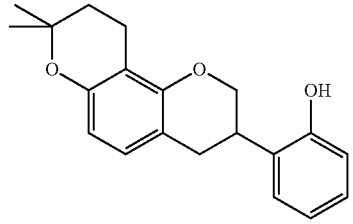
<Compound I-29>
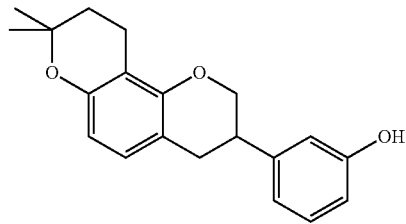
<Compound I-30>
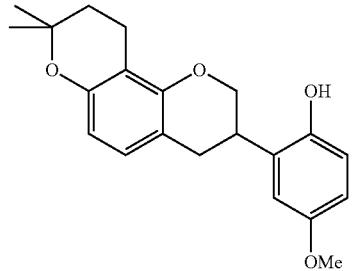

-continued
<Compound I-31>
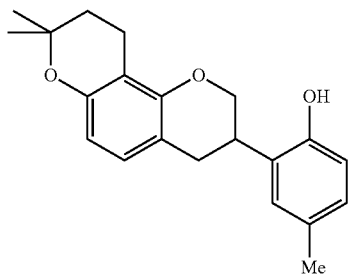
<Compound I-32>
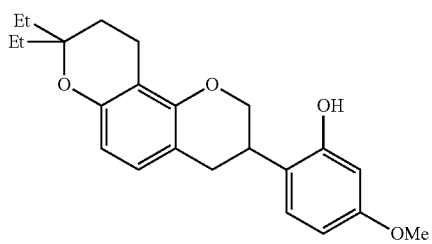
<Compound I-33>
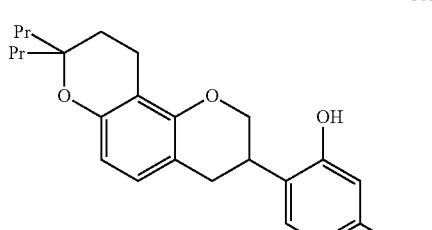
<Compound I-34>
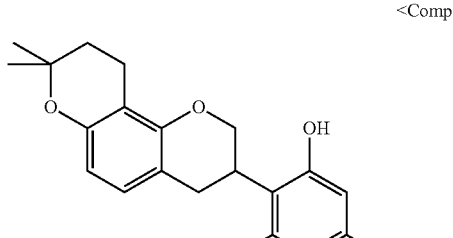
<Compound I-35>
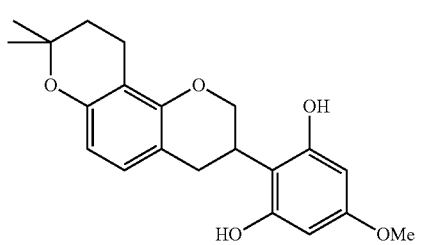
<Compound I-36>
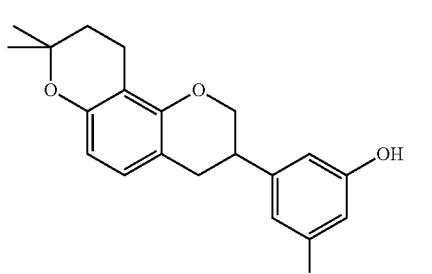
-continued
<Compound I-37>
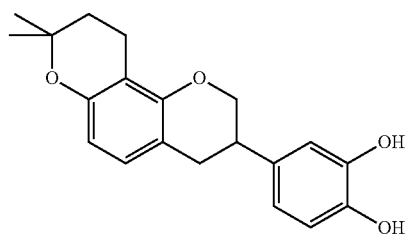
<Compound I-38>
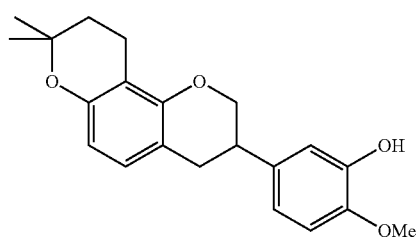
<Compound I-39>
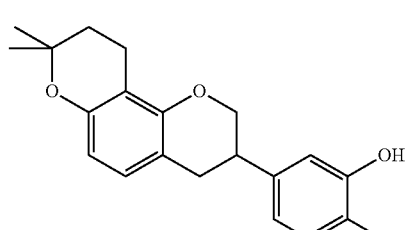
<Compound I-40>
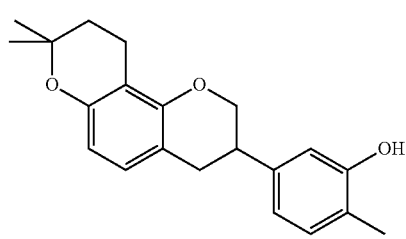
<Compound I-41>
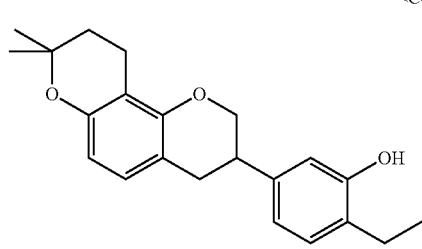
<Compound I-42>
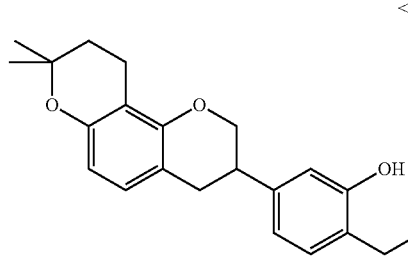

<Compound I-43>

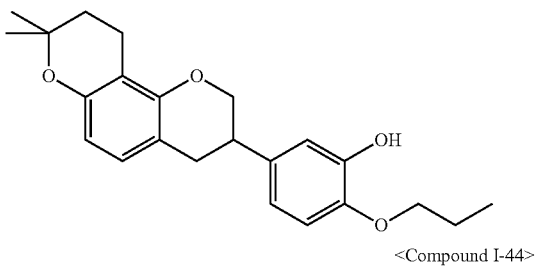

<Compound I-49>

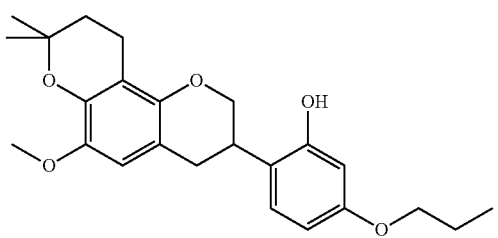

<Compound I-44>

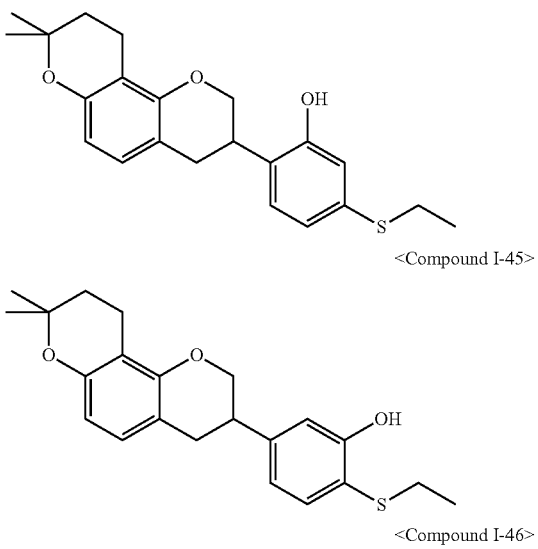

<Compound I-45>

<Compound I-46>

<Compound I-47>

<Compound I-48>

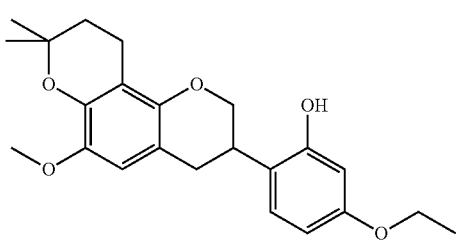

According to an exemplary embodiment, it is preferred that the coupling of the Compound of Chemical Formula 1 with the Compound of Chemical Formula 2 in step a) is performed under basic conditions, and it is further preferred that the coupling of the Compound of Chemical Formula 1 with the Compound of Chemical Formula 2 is performed by using a weak basic Compound as a catalyst. In this case, a synthesis of an undesired Compound by intramolecular aldol condensation reaction may be prevented. Further, according to an exemplary embodiment, the weak basic Compound may be one or more selected from a group consisting of sodium carbonate ($Na_2CO_3$), lithium carbonate ($Li_2CO_3$), potassium carbonate ($K_2CO_3$), sodium hydrogen carbonate ($NaHCO_3$), potassium hydrogen carbonate ($KHCO_3$), triethylamine, and pyridine, and is preferably potassium carbonate or sodium carbonate.

According to an exemplary embodiment, the reducing of the Compound of Chemical Formula 3 in step b) is a step of preparing the Compound of Chemical Formula 4 by selectively reducing only a formyl group (—COH) in a state where a carbonyl group (—CO—) of ketone is safely maintained. The selective reduction may be carried out by adding any one or more reducing agents selected from a group consisting of L-selectride $\{Li[CH(CH_3)CH_2CH_3]_3BH\}$, N-selectride $\{NaB[CH(CH_3)C_2H_5]_3H\}$, K-selectride $\{K[CH(CH_3)CH_2CH_3]_3BH\}$, and LS-selectride $\{LiB[CH(CH_3)CH(CH_3)_2]_3H\}$. The reducing is carried out preferably at −10° C. or less, more preferably at −60° C. or less, and most preferably at −78° C. or less.

According to an exemplary embodiment, the cyclizing in step c) is an intramolecular cyclization reaction, may be started with a step of dissolving the Compound of Chemical Formula 4 in acetonitrile ($CH_3CN$) and adding triphenylphosphonium bromide ($Ph_3P\cdot HBr$), and may be composed of a step of concentrating the resulting product and a step of dissolving the concentrate obtained and adding sodium ethoxide (NaOEt).

[Reaction Formula 3]

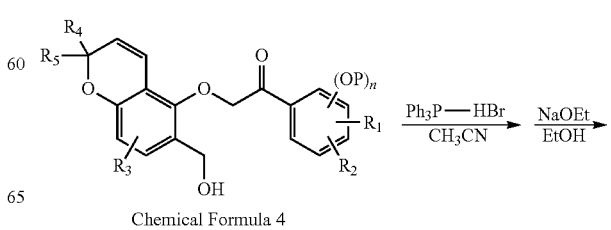

Chemical Formula 4

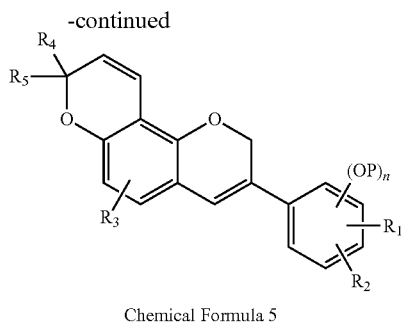

Chemical Formula 5

According to an exemplary embodiment, it is preferred that the concentrating of the resulting product or the dissolving of the concentrate obtained uses ethanol.

According to an exemplary embodiment, when a benzyl group or an analogue thereof is used as a protecting group (P) of the Compound of Chemical Formula 5 in Reaction Formula 1 or 3, a Compound of Chemical Formula (I) may be obtained by simultaneously carrying out a reduction process of a double bond through a hydrogen addition reaction, which uses Pd/C (palladium on carbon) as a catalyst, and a de-protecting group process. If necessary, a pyranochromenyl phenol derivative in a state of having a protecting group may be synthesized, and the protecting group may be removed at an arbitrary time.

Further, another aspect of the present invention provides a Compound represented by the following Chemical Formula 3 or a solvate thereof:

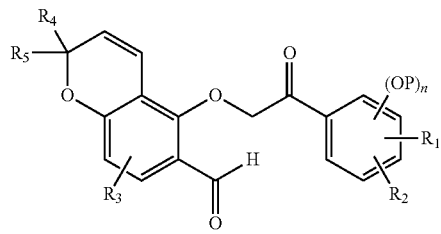

wherein, $R_1$ and $R_2$ are each independently hydrogen atom; hydroxy group; straight or branched $C_1$ to $C_6$ alkyl group unsubstituted or substituted with halogen atom, straight or branched $C_1$ to $C_5$ alkyl group, straight or branched $C_1$ to $C_5$ alkoxy group, or straight or branched $C_1$ to $C_3$ thioalkyl group; halogen atom; straight or branched $C_1$ to $C_6$ alkoxy group unsubstituted or substituted with halogen atom, straight or branched $C_1$ to $C_5$ alkyl group, straight or branched $C_1$ to $C_5$ alkoxy group, or straight or branched $C_1$ to $C_3$ thioalkyl group; straight or branched $C_1$ to $C_4$ thioalkyl group unsubstituted or substituted with halogen atom, straight or branched $C_1$ to $C_5$ alkyl group, straight or branched $C_1$ to $C_5$ alkoxy group, or straight or branched $C_1$ to $C_3$ thioalkyl group; allyloxy group unsubstituted or substituted with halogen atom, straight or branched $C_1$ to $C_5$ alkyl group, straight or branched $C_1$ to $C_5$ alkoxy group, or straight or branched $C_1$ to $C_3$ thioalkyl group; or aryloxy group unsubstituted or substituted with halogen atom, straight or branched $C_1$ to $C_5$ alkyl group, straight or branched $C_1$ to $C_5$ alkoxy group, or straight or branched $C_1$ to $C_3$ thioalkyl group;

$R_3$ is hydrogen atom or $C_1$ to $C_2$ alkyl group or $C_1$ to $C_2$ alkoxy group;

$R_4$ and $R_5$ are each independently hydrogen atom or $C_1$ to $C_6$ alkyl group;

P is a protecting group selected from straight or branched $C_1$ to $C_4$ alkyl group unsubstituted or substituted with halogen atom, straight or branched $C_1$ to $C_5$ alkyl group, straight or branched $C_1$ to $C_5$ alkoxy group, or straight or branched $C_1$ to $C_3$ thioalkyl group; benzyl group unsubstituted or substituted with halogen atom, straight or branched $C_1$ to $C_5$ alkyl group, straight or branched $C_1$ to $C_5$ alkoxy group, or straight or branched $C_1$ to $C_3$ thioalkyl group; allyl group unsubstituted or substituted with halogen atom, straight or branched $C_1$ to $C_5$ alkyl group, straight or branched $C_1$ to $C_5$ alkoxy group, or straight or branched $C_1$ to $C_3$ thioalkyl group; tert-butyldimethylsilyl group; tert-butyldiphenylsilyl group; methylphenylsilyl group; trimethylphenylsilyl group; $MeSO_2$ and $p\text{-}TsSO_2$;

n is 1 to 3; and two or more OPs are the same or different from each other.

According to an exemplary embodiment of the present invention, a 3-phenyl-2,3,4,8,9,10-hexahydropyrano[2,3-f]chromene derivative of Chemical Formula (I) may be prepared by using the Compound of Chemical Formula 3. Specifically, the Compound of Chemical Formula (I) may be synthesized by a method including a step of synthesizing the Compound of Chemical Formula 4 by reducing the Compound of Chemical Formula 3 of the present invention and a step of cyclizing the Compound of Chemical Formula 4. In this case, the Compound of Chemical Formula 3 may use a Compound synthesized by coupling the Compound of Chemical Formula 1 with the Compound of Chemical Formula 2, or a Compound prepared by another method.

In addition, still another aspect of the present invention provides a Compound represented by the following Chemical Formula 4 or a solvate thereof:

[Chemical Formula 4]

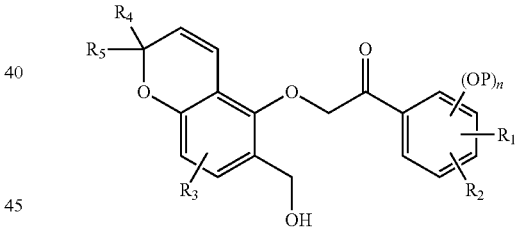

$R_1$ to $R_5$, P, and n in Chemical Formula 4 are the same as those defined in Chemical Formula 3.

According to an exemplary embodiment of the present invention, a 3-phenyl-2,3,4,8,9,10-hexahydropyrano[2,3-f]chromene derivative of Chemical Formula (I) may be prepared by using the Compound of Chemical Formula 4. Specifically, the Compound of Chemical Formula (I) may be synthesized by a method including cyclizing the Compound of Chemical Formula 4. In this case, the Compound of Chemical Formula 4 may use a Compound synthesized by reducing the Compound of Chemical Formula 3 or a Compound prepared by another method.

The Compound of Chemical Formula 3 or 4 according to the present invention may include all the solvates including all the salts and hydrates, which may be prepared by typical methods.

Further, yet another aspect of the present invention provides a 3-phenyl-2,8-dihydropyrano[2,3-f]chromene Compound represented by the following Chemical Formula 5 or a solvate thereof:

[Chemical Formula 5]

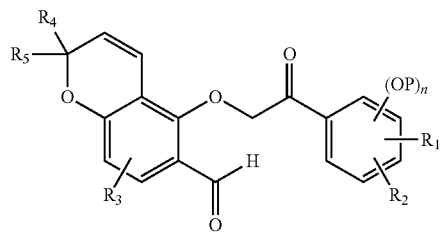

$R_1$ to $R_5$, P, and n in Chemical Formula 5 are the same as those defined in Chemical Formula 3.

According to an exemplary embodiment, the 3-phenyl-2,8-dihydropyrano[2,3-f]chromene Compound of Chemical Formula 5 may be one or more of the following Compounds:

<Compound 5-1>

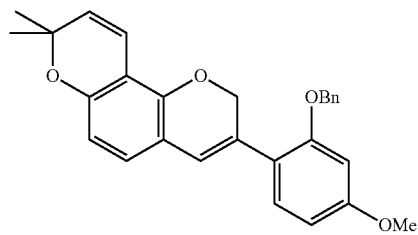

<Compound 5-2>

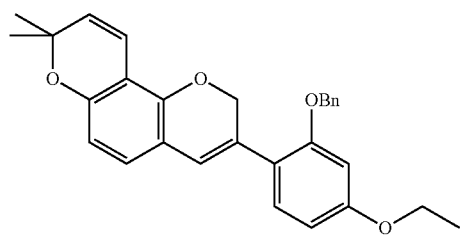

<Compound 5-3>

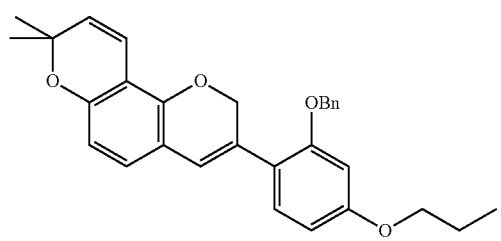

<Compoound 5-4>

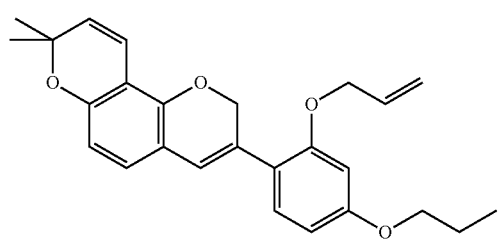

<Compound 5-5>

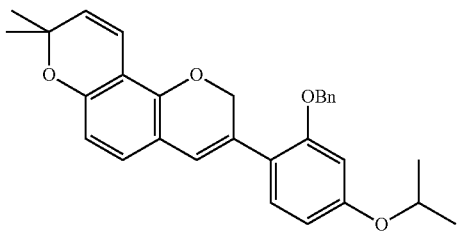

<Compound 5-6>

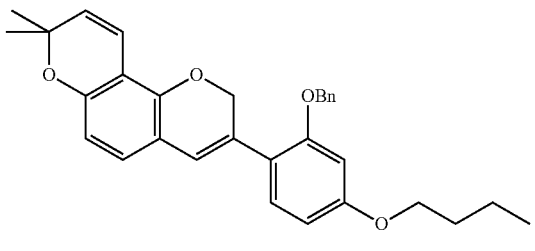

<Compound 5-7>

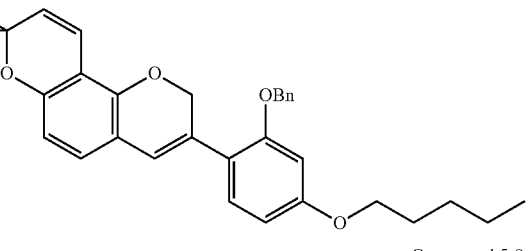

<Compound 5-8>

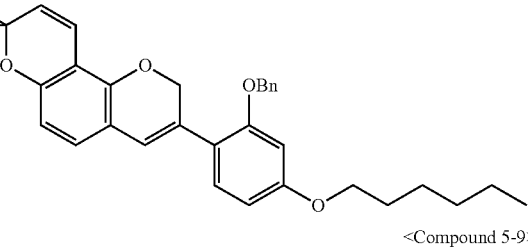

<Compound 5-9>

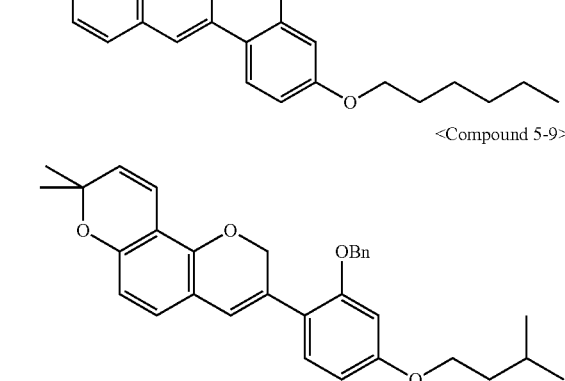

<Compound 5-10>

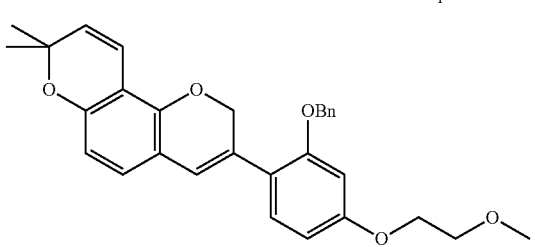

<Compound 5-11>
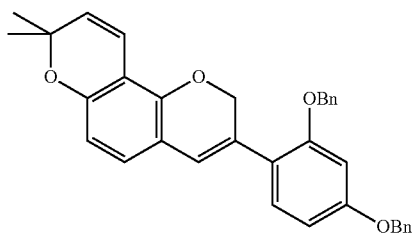
<Compound 5-12>
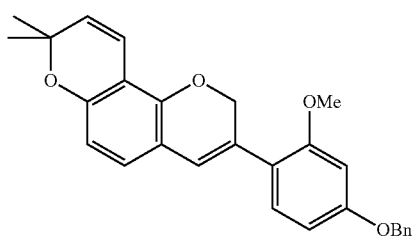
<Compound 5-13>
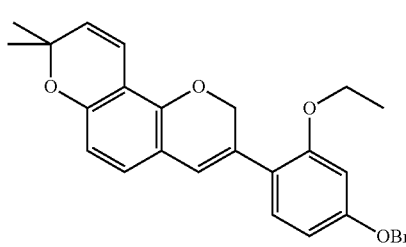
<Compound 5-14>
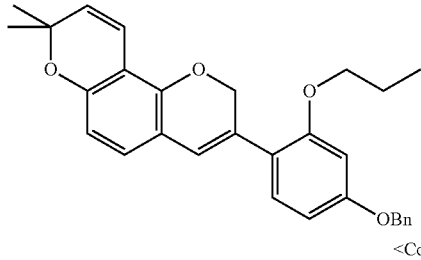
<Compound 5-15>
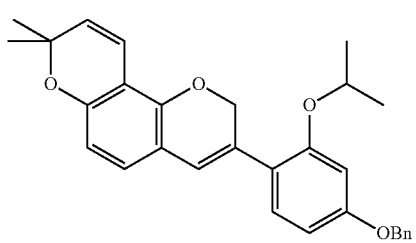
<Compound 5-16>
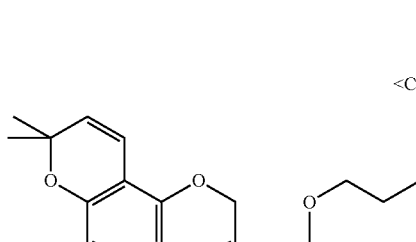
<Compound 5-17>
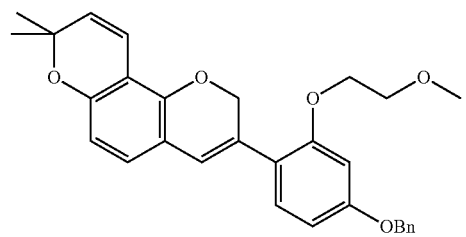
<Compound 5-18>
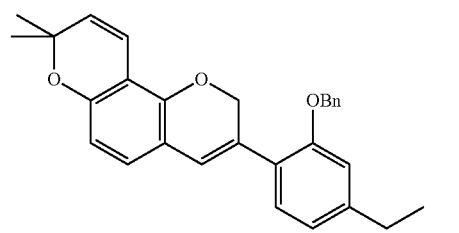
<Compound 5-19>
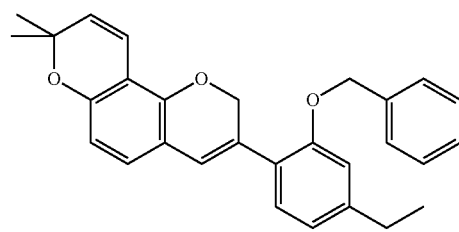
<Compound 5-20>
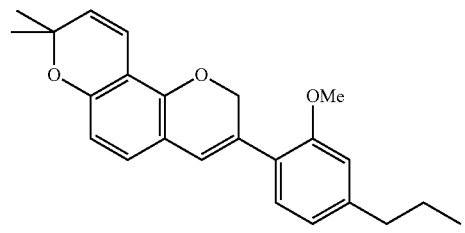
<Compound 5-21>
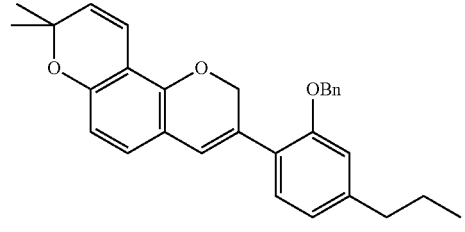
<Compound 5-22>
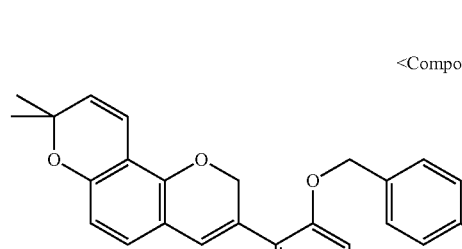

<Compound 5-23>
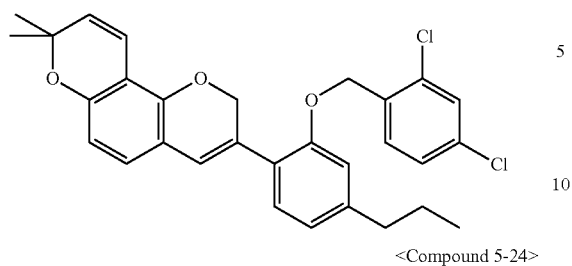
<Compound 5-24>
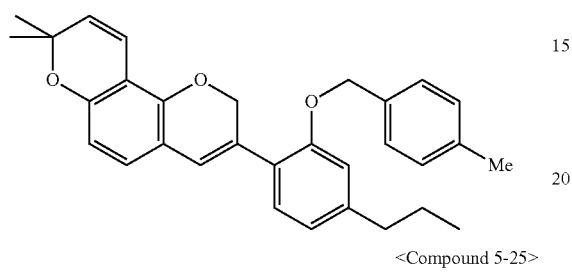
<Compound 5-25>
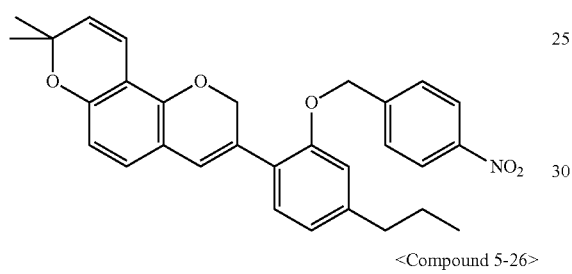
<Compound 5-26>
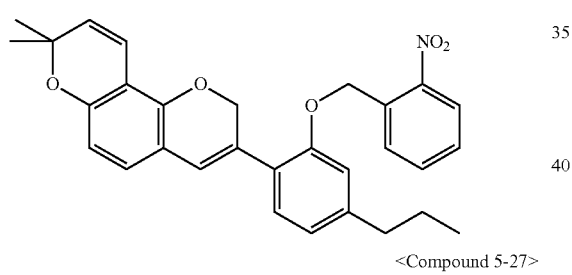
<Compound 5-27>
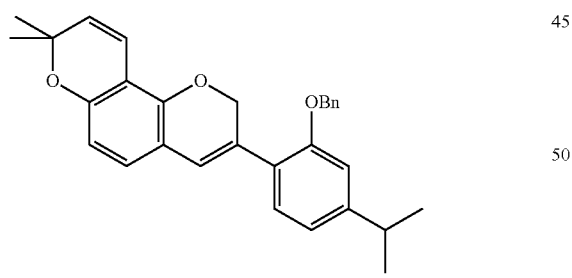
<Compound 5-28>
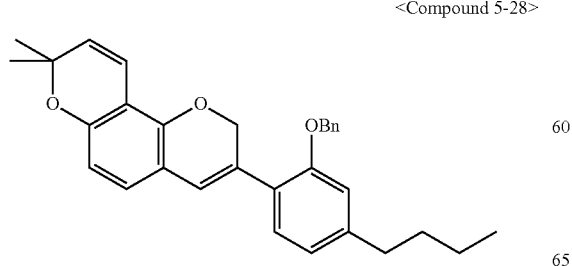
<Compound 5-29>
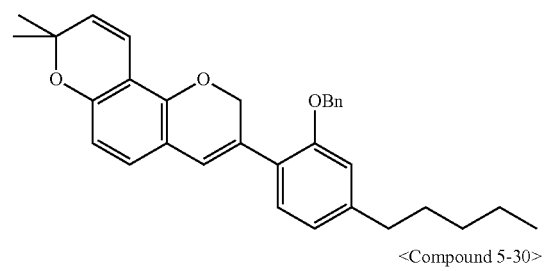
<Compound 5-30>
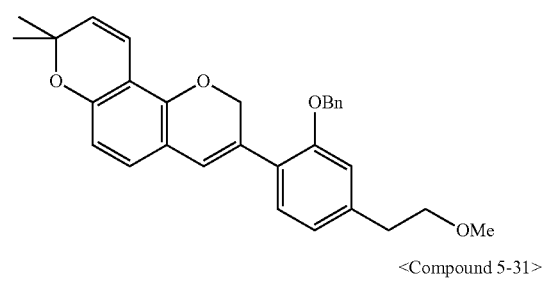
<Compound 5-31>
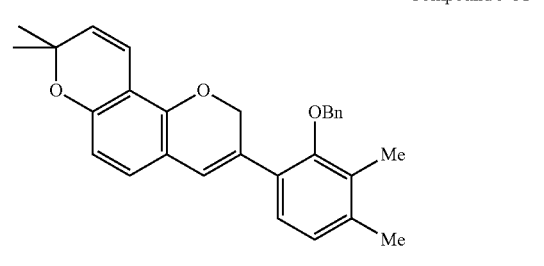
<Compound 5-32>
<Compound 5-33>
<Compound 5-34>

<Compound 5-35>
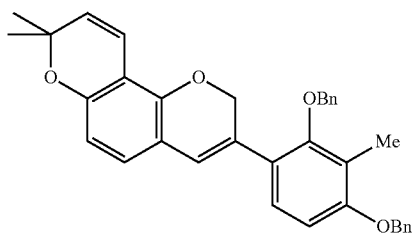
<Compound 5-36>
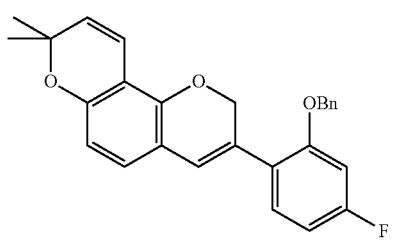
<Compound 5-37>
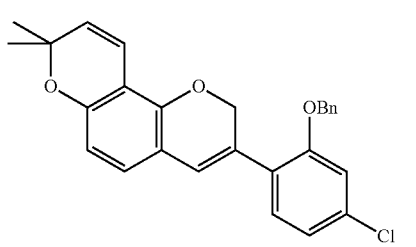
<Compound 5-38>
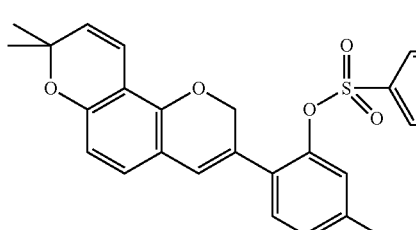
<Compound 5-39>
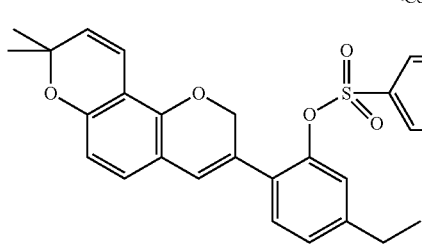
<Compound 5-40>
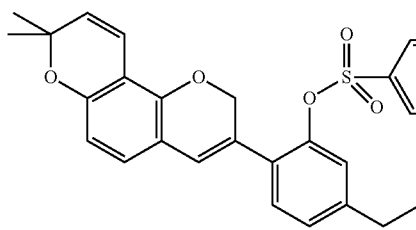
<Compound 5-41>
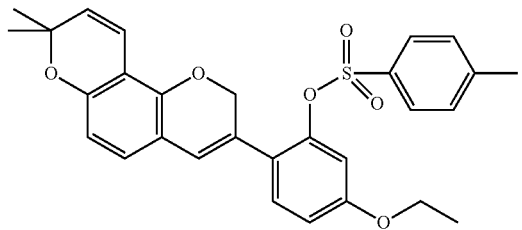
<Compound 5-42>
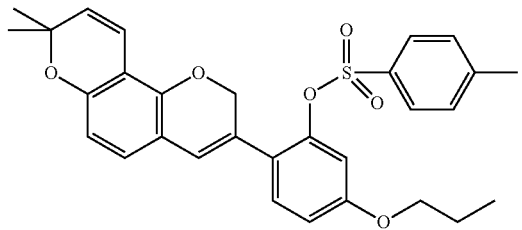
<Compound 5-43>
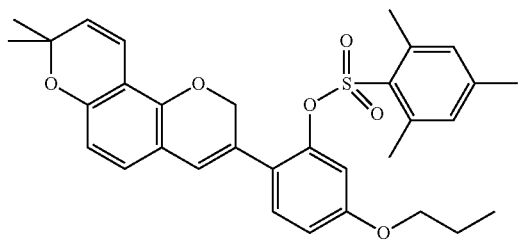
<Compound 5-44>
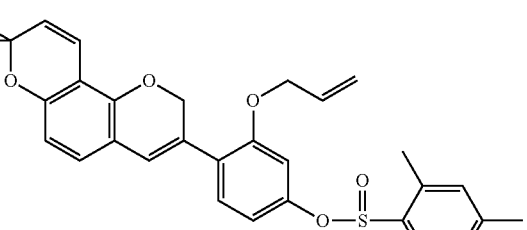
<Compound 5-45>
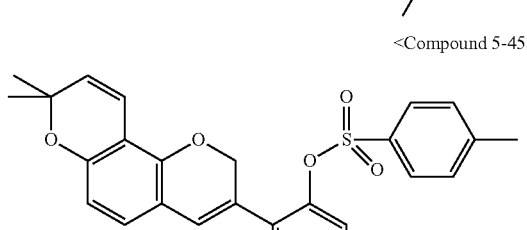
<Compound 5-46>
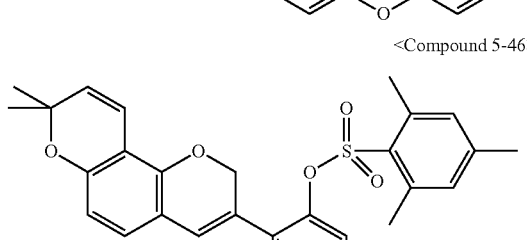

<Compound 5-47>
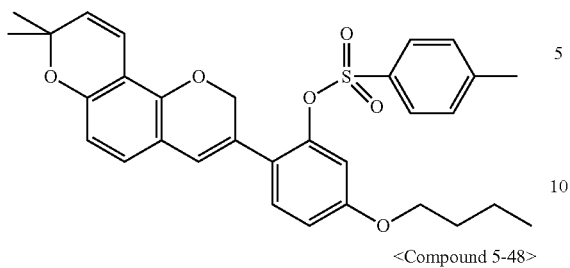
<Compound 5-48>
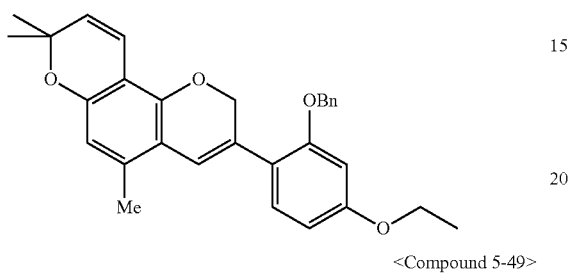
<Compound 5-49>
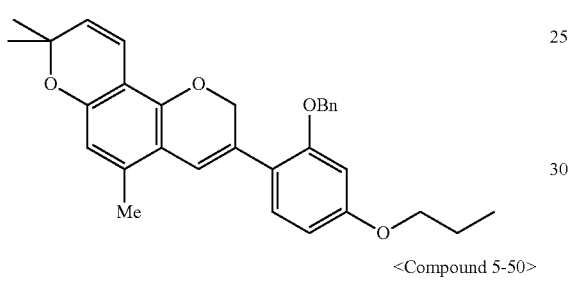
<Compound 5-50>
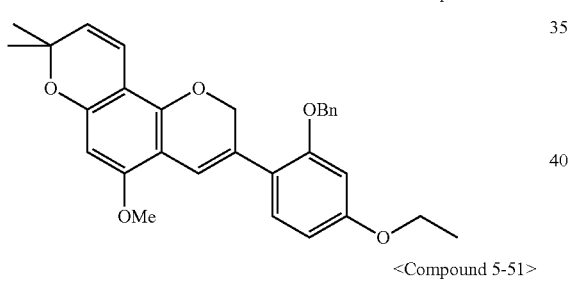
<Compound 5-51>
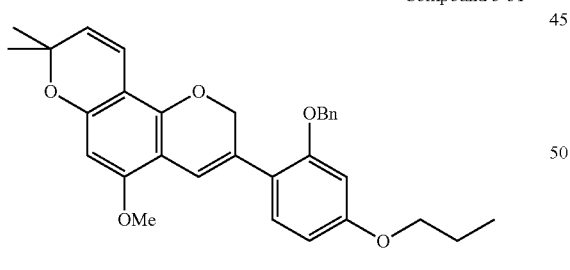
<Compound 5-52>
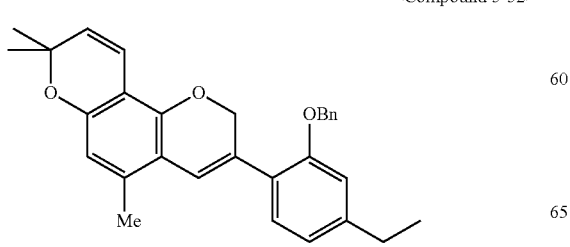
<Compound 5-53>
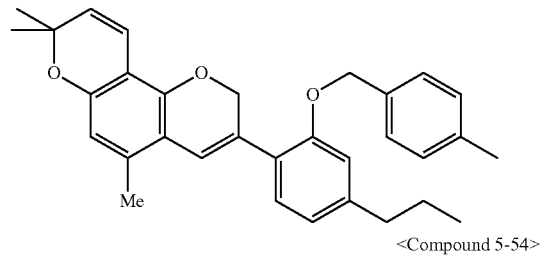
<Compound 5-54>
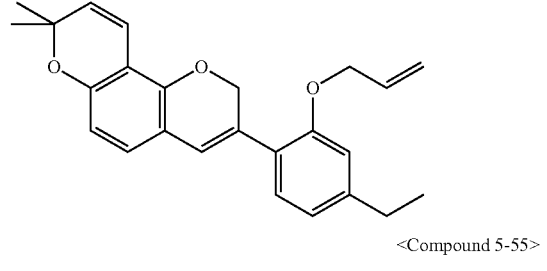
<Compound 5-55>
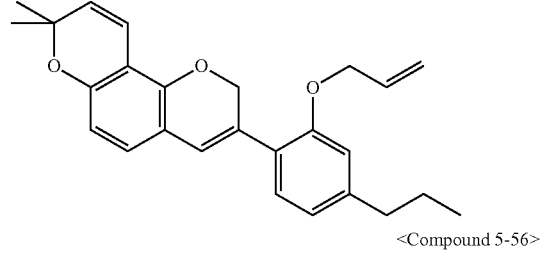
<Compound 5-56>
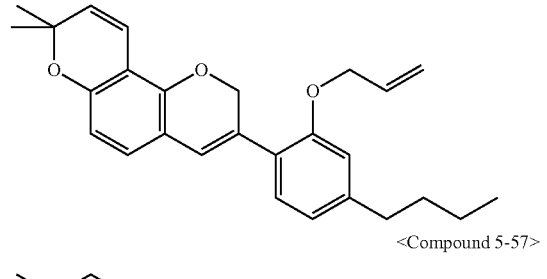
<Compound 5-57>
<Compound 5-58>
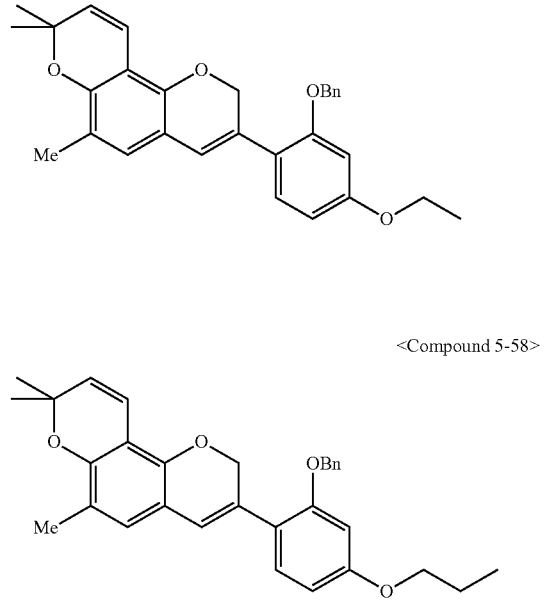

-continued

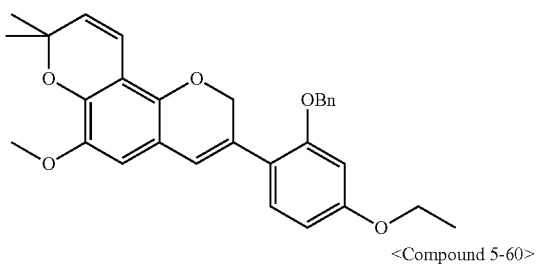
<Compound 5-59>

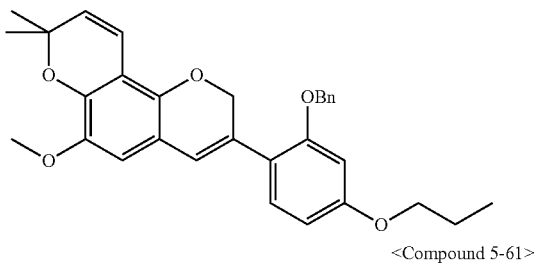
<Compound 5-60>

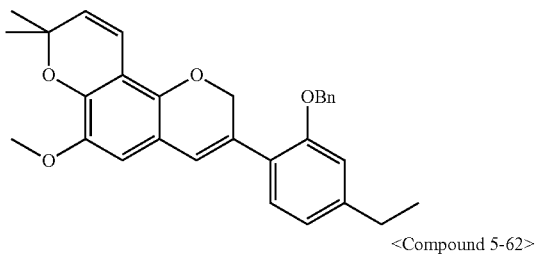
<Compound 5-61>

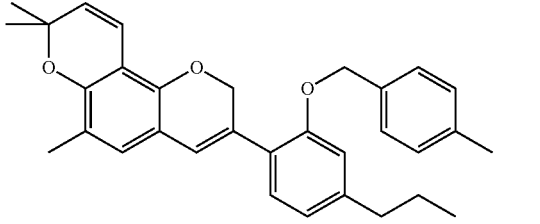
<Compound 5-62>

According to an exemplary embodiment of the present invention, a 3-phenyl-2,3,4,8,9,10-hexahydropyrano[2,3-f] chromene derivative of Chemical Formula (I) may be prepared by using the Compound of Chemical Formula 5. Specifically, the Compound of Chemical Formula (I) may be synthesized by reducing the double bond and removing the protecting group in the Compound of Chemical Formula 5. In this case, the Compound of Chemical Formula 5 may use a Compound synthesized by the method of Reaction Formula 1 or a Compound prepared by another method.

The 3-phenyl-2,8-dihydropyrano[2,3-f]chromene Compound of Chemical Formula 5 according to the present invention may include all the solvates including all the salts and hydrates, which may be prepared by typical methods.

In addition, still yet another aspect of the present invention provides a method for synthesizing an optical isomer of a 3-phenyl-2,3,4,8,9,10-hexahydropyrano[2,3-f]chromene derivative of Chemical Formula (I), the method including:

A) coupling a Compound represented by Chemical Formula 1 with a Compound represented by Chemical Formula 2 to form a Compound of Chemical Formula 3;

B) reducing the Compound of Chemical Formula 3 to form a Compound of Chemical Formula 4;

C) cyclizing the Compound of Chemical Formula 4 to form a Compound of Chemical Formula 5; and D) subjecting the Compound represented by Chemical Formula 5 to an asymmetric hydrogenation reaction to form an optical isomer Compound of Chemical Formula 6a (R-form) or 6b (S-form):

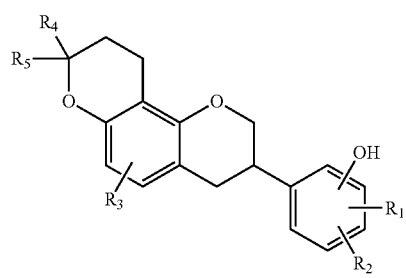

(I)

[Reaction Formula 2]

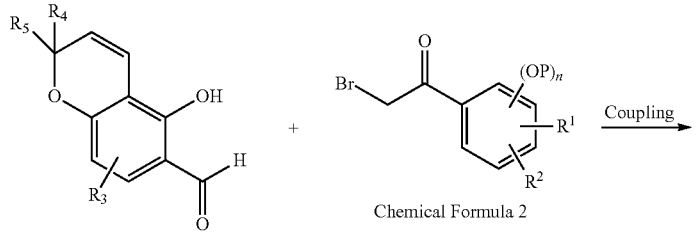

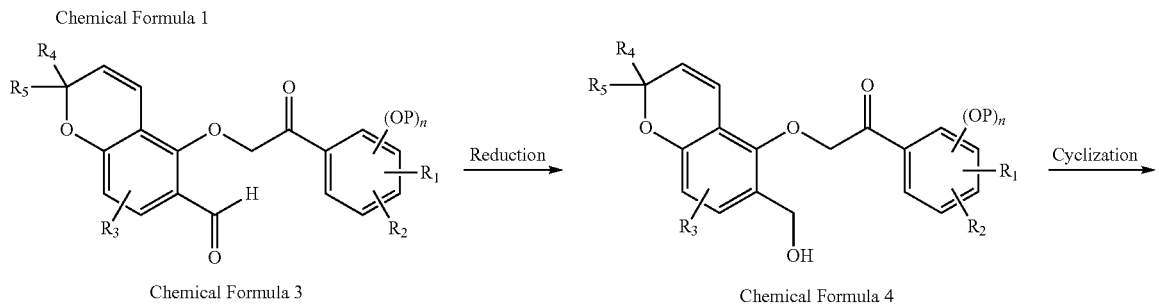

-continued

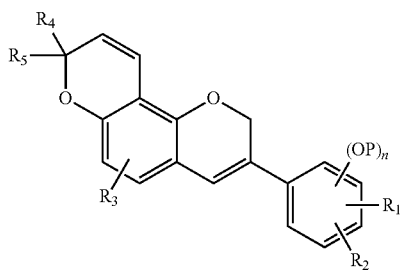

Chemical Formula 5

Asymmetric Hydrogen Substitution Reaction

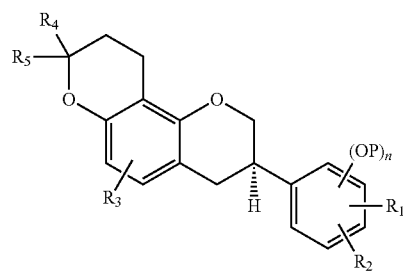

Chemical Formula 6a(R-form)

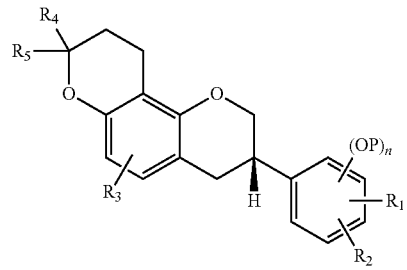

Chemical Formula 6b(S-form)

$R_1$ to $R_5$, P, and n in the chemical formulae are the same as those defined in Reaction Formula 1.

According to an exemplary embodiment of the present invention, the method for synthesizing the optical isomer of the 3-phenyl-2,3,4,8,9,10-hexahydropyrano[2,3-f]chromene derivative of Chemical Formula (I) may further include a process of removing a protecting group from the Compound of Chemical Formula 6a or 6b. Specifically, through one de-protecting group process, the optical isomer of the 3-phenyl-2,3,4,8,9,10-hexahydropyrano[2,3-f]chromene derivative of Chemical Formula (I) may be effectively synthesized from the optical isomer Compound of Chemical Formula 6a or 6b.

Examples of the optical isomer of the 3-phenyl-2,3,4,8,9,10-hexahydropyrano[2,3-f]chromene derivative of Chemical Formula (I) include the following Compounds:

<Compound I-2a>

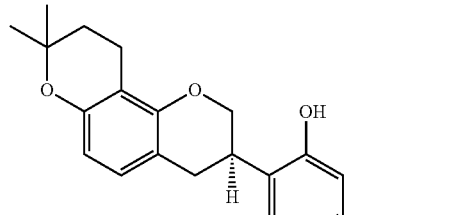

<Compound I-2b>

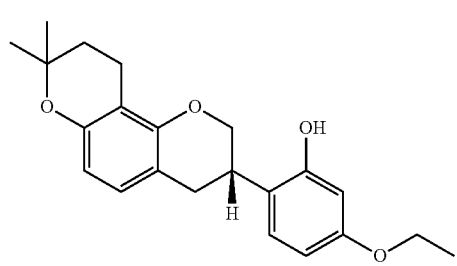

<Compound I-3a>

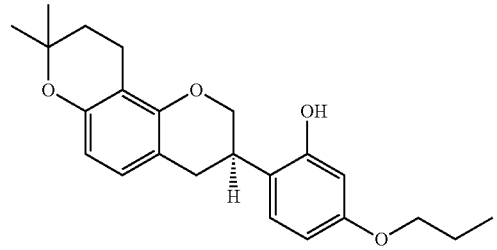

<Compound I-3b>

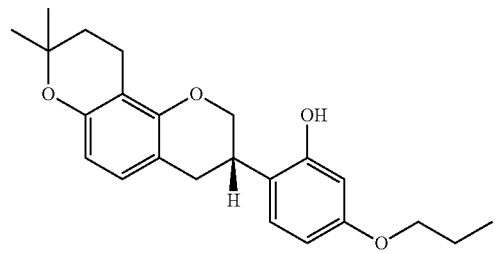

<Compound 5a>

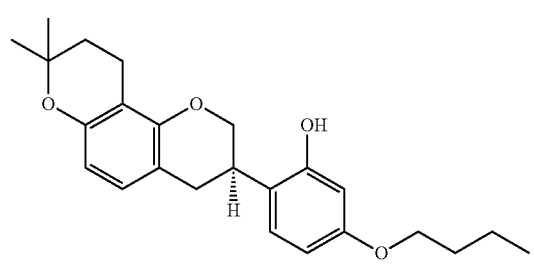

<Compound I-5b>

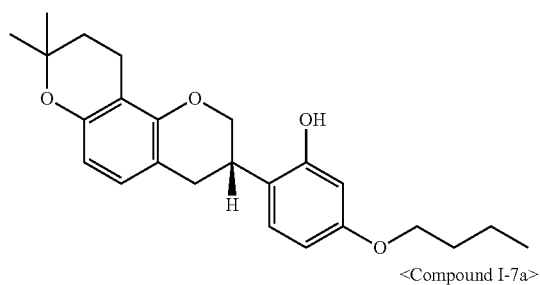

<Compound I-7a>

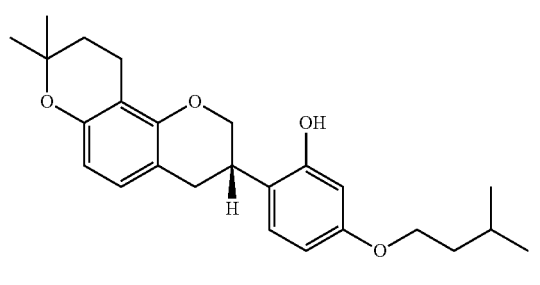

<Compound I-7b>

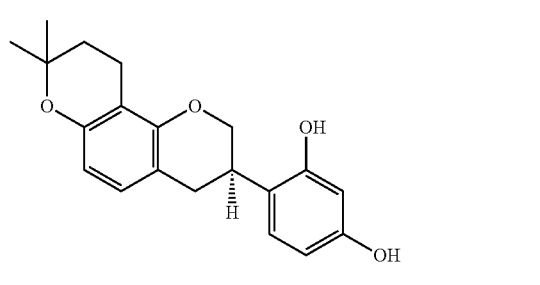

<Compound I-9a>

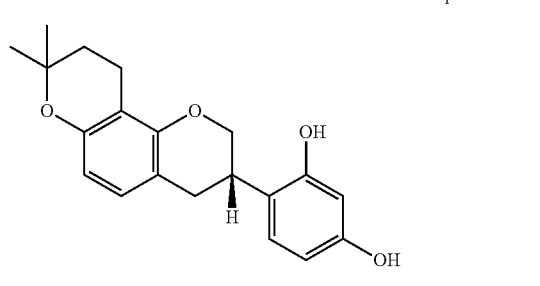

<Compound I-9b>

<Compound I-13a>

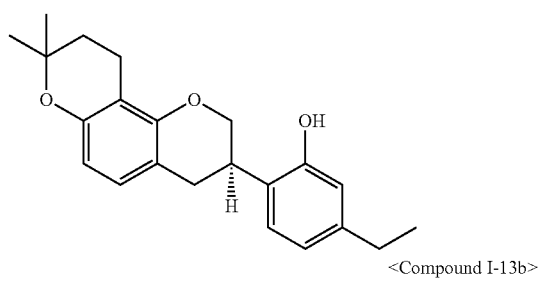

<Compound I-13b>

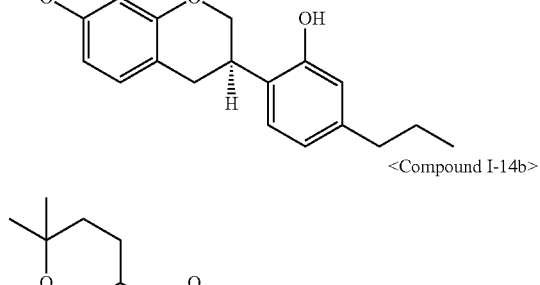

<Compound I-14a>

<Compound I-14b>

According to an exemplary embodiment of the present invention, the reactions in Steps A) to C) are the same as Steps a) to c) in Reaction Formula 1, that is, in the process of synthesizing the 3-phenyl-2,3,4,8,9,10-hexahydropyrano[2,3-f]chromene derivative of Chemical Formula (I).

According to an exemplary embodiment of the present invention, the asymmetric hydrogenation reaction in Step D) uses a chiral ligand which serves as a catalyst, and the asymmetric hydrogenation reaction may be carried out because the reaction position is specified due to a stereoscopic factor or an electronic factor between the chiral ligand and the Compound of Chemical Formula 5.

The chiral ligand is preferably selected from a group consisting of a phospholane ligand, a SimplePHOX ligand, a PHOX ligand, and UbaPHOX, and is most preferably UbaPHOX.

It is preferred that the UbaPHOX uses [((4S,5S)-Cy2-UbaPHOX)Ir(COD)]BARF, that is, 1,5-cyclooctadiene{[dibenzyl((4S,5S)-5-methyl-2-phenyl-4,5-dihydro-4-oxazolyl)methyl]dicyclohexylphosphinite κN:κP}iridium(I) tetrakis(3,5-bis(trifluoromethyl)phenyl)borate when an R isomer of the Compound of Chemical Formula (I) is synthesized. Further, it is preferred that the UbaPHOX uses [(((4R,5R)-Cy2-UbaPHOX)Ir(COD)]BARF, that is, 1,5-cyclooctadiene{[dibenzyl((4R,5R)-5-methyl-2-phenyl-4,5-dihydro-4-oxazolyl)methyl]dicyclohexylphosphinite κN:κP}iridium(I) tetrakis(3,5-bis(trifluoromethyl)phenyl)borate when an S isomer of the Compound of Chemical Formula (I) is synthesized.

According to an exemplary embodiment, when a benzyl group or an analogue thereof is used as a protecting group (P) of the optical isomer Compound of Chemical Formula 6a or 6b in Reaction Formula 2, the protecting group may be removed by using Pd/C (palladium on carbon) as a catalyst.

Furthermore, a further aspect of the present invention provides an optical isomer Compound represented by the following Chemical Formula 6a or 6b, or a solvate thereof:

[Chemical Formula 6a]

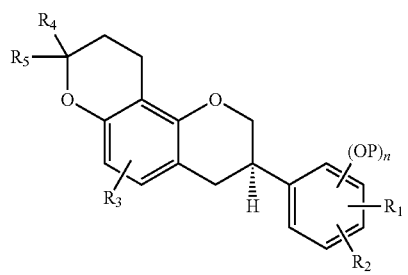

[Chemical Formula 6b]

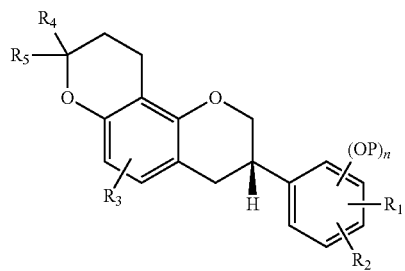

$R_1$ to $R_5$, P, and n in Chemical Formula 6a or 6b are the same as those defined in Chemical Formula 3.

According to an exemplary embodiment of the present invention, the optical isomer Compound of Chemical Formula 6a or 6b may be one or more from the following Compounds:

<Compound 6-2a>

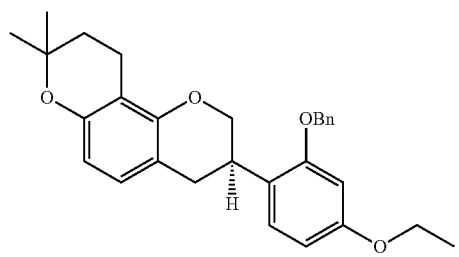

<Compound 6-2b>

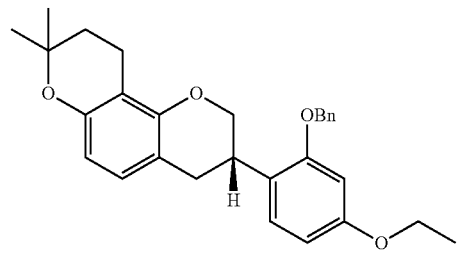

<Compound 6-3a>

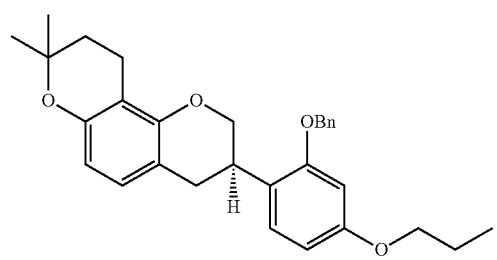

<Compound 6-3b>

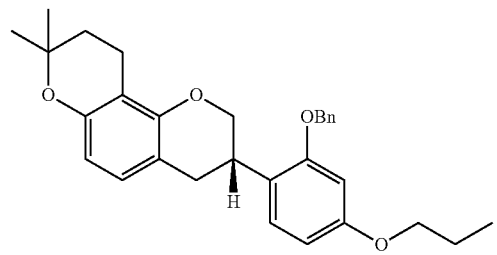

<Compound 6-5a>

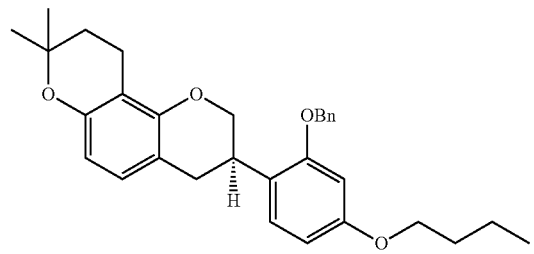

<Compound 6-5b>

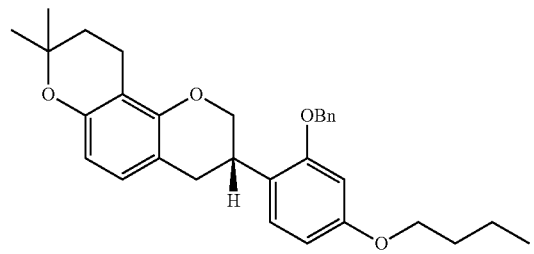

<Compound 6-7a>

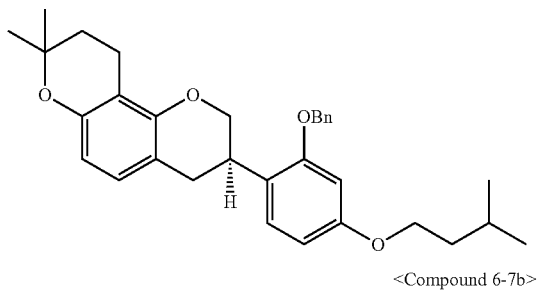

<Compound 6-7b>

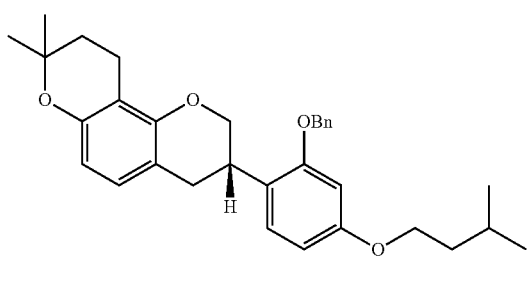

<Compound 6-9a>

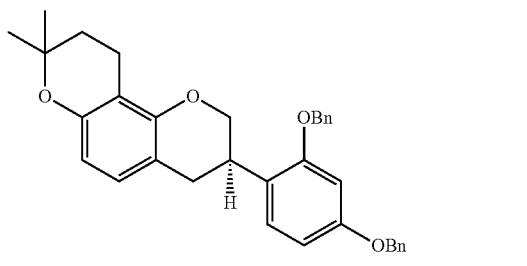

<Compound 6-9b>

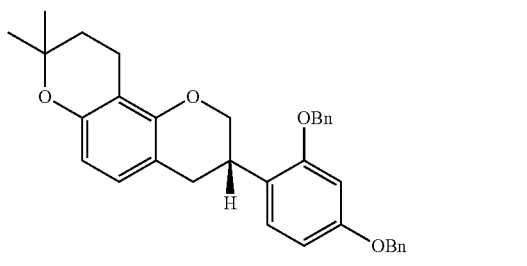

<Compound 6-13a>

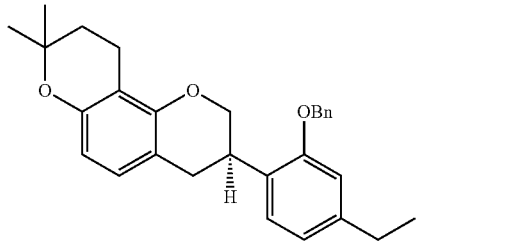

<Compound 6-13b>

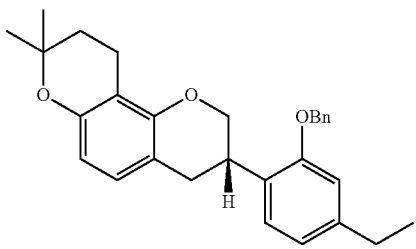

<Compound 6-14a>

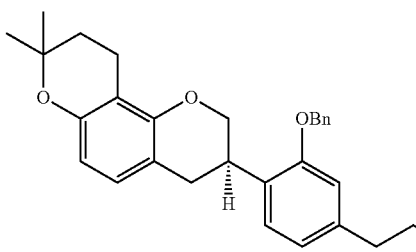

<Compound 6-14b>

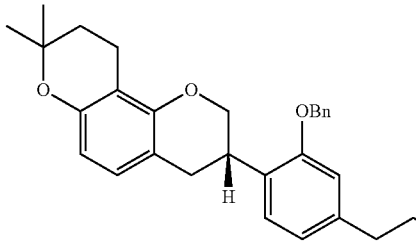

According to an exemplary embodiment of the present invention, an optical isomer of a 3-phenyl-2,3,4,8,9,10-hexahydropyrano[2,3-f]chromene derivative of Chemical Formula (I) may be prepared by using the Compound of Chemical Formula 6a or 6b. Specifically, the optical isomer Compound of Chemical Formula (I) may be synthesized by removing the protecting group from the Compound of Chemical Formula 6a or 6b. In this case, the Compound of Chemical Formula 6a or 6b may use a Compound synthesized by the method of Reaction Formula 2 or a Compound prepared by another method.

The optical isomer Compound of Chemical Formula 6a or 6b according to the present invention may include all the solvates including all the salts and hydrates, which may be prepared by typical methods.

Hereinafter, one or more specific examples will be described in more detail through Preparation Examples and Examples. However, these Preparation Examples and Examples are provided only for exemplarily explaining one or more specific examples, and the scope of the present invention is not limited by these Preparation Examples and Examples.

As the reagents used in the following Preparation Examples and Examples, those purchased from Sigma-Aldrich, Inc. (USA) were used unless otherwise specifically indicated.

Preparation Example 1: Synthesis of 3-(2-(benzyloxy)-4-methoxyphenyl)-8,8-dimethyl-2,8-dihydropyrano[2,3-f]chromene (Compound 5-1)

1-1: Preparation of 5-(2-(2-benzyloxy-4-methoxyphenyl)-2-oxoethoxy)-2,2-dimethyl-2H-chromene-6-carbaldehyde 4.08 g (20.0 mmol) of 5-hydroxy-2,2-dimethyl-2H-chromene-6-carbaldehyde and 6.70 g (20.0 mmol) of 1-(2-(benzyloxy)-4-methoxyphenyl)-2-bromoethanone were dissolved in 20 ml of acetone ($CH_3COCH_3$), 2.76 g (20.0 mmol) of potassium carbonate ($K_2CO_3$) was added to the solution, and then the resulting mixture was vigorously stirred at room temperature for 12 hours. Solid components were removed by filtering the reaction mixture, the resulting mixture was concentrated, the concentrate obtained was dissolved again in 20 ml of ethyl acetate ($CH_3COOC_2H_5$), the resulting solution was washed with saturated brine, and the organic solution layer was separated, and then dried over magnesium sulfate ($MgSO_4$). Thereafter, magnesium sulfate was removed by filtering the organic solution layer, and then the solution was concentrated and recrystallized with isopropyl alcohol (IPA), thereby obtaining 7.46 g (16.3 mmol) of 5-(2-(2-benzyloxy-4-methoxyphenyl)-2-oxoethoxy)-2,2-dimethyl-2H-chromene-6-carbaldehyde (Yield: 81.4%). $^1$H-NMR and $^{13}$C-NMR results for the obtained Compound are as follows.

$^1$H-NMR (CDCl3): 10.152 (s, 1H), 8.066 (d, 1H, J=8.8 Hz), 7.618 (d, 1H, J=8.4 Hz), 7.280 (m, 5H), 6.629 (d, 1H, J=8.8 Hz), 6.582 (dd, 1H, J=8.8, 2.4 Hz), 6.562 (d, 1H, J=10.0 Hz), 6.500 (d, 1H, J=2.4 Hz), 5.567 (d, 1H, J=10.0 Hz), 5.084 (s, 2H), 5.070 (s, 2H), 3.846 (s, 3H), 1.406 (s, 6H).

$^{13}$C-NMR (CDCl3): 192.083, 188.584, 165.281, 160.344, 159.600, 158.640, 135.146, 133.140, 130.319, 129.751, 128.704, 128.574, 127.759, 122.578, 117.958, 116.116, 114.234, 113.234, 106.271, 99.133, 82.035, 77.319, 71.020, 55.632, 28.108.

1-2: Preparation of 1-(2-(benzyloxy)-4-methoxyphenyl)-2-((6-hydroxymethyl-2,2-dimethyl-2H-chromen-5-yl)oxy)ethanone 4.61 g (10.0 mmol) of 5-(2-(2-benzyloxy-4-methoxyphenyl)-2-oxoethoxy)-2,2-dimethyl-2H-chromene-6-carbaldehyde obtained in Preparation Example 1-1 was dissolved in 50 ml of tetrahydrofuran (THF) under a nitrogen atmosphere, and then the solution was cooled to −78° C. The cooled reaction solution was vigorously stirred, and 10 ml of a 1.0 M solution of L-Selectride®-THF was slowly added thereto for 30 minutes in a state where the reaction temperature was maintained at −78° C. The reaction solution was additionally stirred at −78° C. for 30 minutes, and then additionally vigorously stirred for 30 minutes in a state where the reaction solution was slowly heated to room temperature. Thereafter, the reaction was terminated by slowly adding 20 ml of concentrated brine in a state where the reaction solution was cooled to 0° C., the organic solution layer was separated, and then the aqueous layer was extracted once more by using 20 ml of ethyl acetate, and mixed with the organic solution layer. The organic solution layer was concentrated by removing moisture over magnesium sulfate, and then performing distillation under reduced pressure. The concentrate obtained was cleanly separated by silica gel, thereby obtaining 3.43 g (7.45 mmol) of 1-(2-benzyloxy-4-methoxyphenyl)-2-((6-hydroxymethyl-2H-chromene-5-yl)oxy)ethanone (Yield: 74.5%). $^1$H-NMR and $^{13}$C-NMR results for the obtained Compound are as follows.

$^1$H-NMR (CDCl3): 8.074 (d, 1H, J=8.8 Hz), 7.32-7.39 (b, 5H), 7.010 (d, 1H, J=8.0 Hz), 6.599 (d, 1H, J=8.8, 2.0 Hz), 6.533 (d, 1H, J=8.0 Hz), 6.506 (d, 1H, J=2.0 Hz), 6.384 (d, 1H, J=10.0 Hz) 5.467 (d, 1H, J=10.0 Hz), 5.132 (s, 2H), 5.097 (s, 2H), 4.523 (d, 2H, J=6.4 Hz), 3.844 (s, 3H), 3.520 (t, 1H, J=6.4 Hz), 1.368 (s, 6H).

$^{13}$C-NMR (CDCl3): 194.139, 165.340, 160.469, 154.230, 153.719, 135.322, 133.295, 130.284, 129.700, 128.760, 128.571, 127.896, 126.099, 117.908, 117.245, 114.330, 112.064, 106.223, 99.169, 80.718, 75.488, 70.941, 61.432, 55.627, 27.528.

1-3: Preparation of {3-(2-(benzyloxy)-4-methoxyphenyl)-8,8-dimethyl-2,8-dihydropyrano[2,3-f] chromene 3.43 g (7.45 mmol) of 1-(2-benzyloxy-4-methoxyphenyl)-2-((6-hydroxymethyl-2,2-dimethyl-2H-chromene-5-yl)oxy)ethanone obtained in Preparation Example 1-2 was dissolved in 25 ml of acetonitrile ($CH_3CN$), and 2.81 g (8.20 mmol) of triphenylphosphonium bromide ($Ph_3P \cdot HBr$) was gradually added thereto while vigorously stirring the resulting solution at room temperature. The prepared reaction solution was vigorously stirred at room temperature for 10 hours, and then concentrated by performing distillation under reduced pressure, and the concentrate obtained was dissolved by adding 20 ml of ethanol to the concentrate. Thereafter, the solution was concentrated again by performing distillation under reduced pressure, and the concentrate obtained was dissolved by adding 20 ml of ethanol to the concentrate.

Next, 0.24 g (35 mmol) of sodium ethoxide (NaOEt) was added thereto at room temperature while vigorously stirring the reaction solution, and then a solid was precipitated by stirring the resulting solution overnight in a state where the solution was heated to 35° C. The precipitated solid was filtered, and then 20 ml of ethanol was added again thereto, and the resulting mixture was refluxed for 1 hour while being vigorously stirred, and additionally stirred for 1 hour in a state where the mixture was cooled to room temperature. The produced solid was filtered, and the filtered solid was washed with iced ethanol at 0° C.

The solid was thoroughly dried in vacuum, thereby obtaining 2.34 g (5.47 mmol) of 3-(2-benzyloxy-4-methoxyphenyl)-8,8-dimethyl-2,8-dihydropyrano[2,3-f]chromene (Yield: 73.5%). $^1$H-NMR and $^{13}$C-NMR results for the obtained Compound are as follows.

$^1$H-NMR (CDCl3): 7.25~7.43 (m, 5H), 7.248 (d, 2H, J=8.8 Hz), 6.807 (d, 1H, J=8.0 Hz), 6.625 (d, 1H, J=10.0 Hz), 6.521 (s, 1H), 6.520 (d, 1H, J=2.4 Hz), 6.512 (dd, J=8.8, 2.4 Hz), 6.364 (d, 1H, J=8.0 Hz), 5.573 (d, 1H, J=10.0 Hz), 5.043 (s, 2H), 4.991 (s, 2H), 3.789 (s, 3H), 1.415 (s, 6H).

$^{13}$C-NMR (CDCl3): 160.484, 157.297, 153.356, 149.196, 136.496, 129.335, 129.254, 128.603, 128.559, 127.994, 127.410, 126.520, 121.591, 121.314, 116.947, 116.641, 109.521, 109.211, 105.064, 99.963, 76.038, 70.414, 68.490, 55.402, 27.826.

Preparation Example 2: Synthesis of 3-(2-(benzyloxy)-4-ethoxyphenyl)-8,8-dimethyl-2,8-dihydropyrano[2,3-f]chromene (Compound 5-2)

2-1: Preparation of 5-(2-(2-(benzyloxy)-4-ethoxyphenyl)-2-oxoethoxy)-2,2-dimethyl-2H-chromene-6-carbaldehyde 5-hydroxy-2,2-dimethyl-2H-6-carbaldehyde and 1-(2-(benzyloxy)-4-ethoxyphenyl)-2-bromoethanone were reacted by using the same method as in Preparation Example 1-1, thereby obtaining 5-(2-(2-(benzyloxy)-4-ethoxyphenyl)-2-oxoethoxy)-2,2-dimethyl-2H-chromene-6-carbaldehyde. $^1$H-NMR and $^{13}$C-NMR results for the obtained Compound are as follows.

$^1$H-NMR (CDCl3): 10.151 (s, 1H), 8.053 (d, 1H, J=8.8 Hz), 7.617 (d, 1H, J=8.8 Hz), 7.30 (m, 5H), 6.627 (d, 1H, J=8.8 Hz), 6.585 (dd, 1H, J=8.8, 2.4 Hz), 6.562 (d, 1H, J=10.0 Hz), 6.495 (d, 1H, J=2.4 Hz), 6.556 (d, 1H, J=10.0 Hz), 5.566 (d, 1H, J=10.0 Hz), 5.082 (s, 2H), 5.062 (s, 2H), 4.077 (q, 2H, J=7.2 Hz), 1.421 (t, 3H, J=7.2 Hz), 1.404 (s, 6H).

$^{13}$C-NMR (CDCl3): 192.036, 188.581, 164.708, 160.366, 159.592, 158.671, 135.191, 133.108, 130.304, 129.706, 128.690, 128.550, 127.742, 122.585, 117.759, 116.122, 114.235, 113.226, 106.728, 99.482, 82.060, 77.320, 70.986, 63.973, 28.105, 14.578.

2-2: Preparation of 1-(2-(benzyloxy)-4-ethoxyphenyl)-2-((6-hydroxymethyl-2,2-dimethyl-2H-chromen-5-yl)oxy)ethanone 5-(2-(2-(benzyloxy)-4-ethoxyphenyl)-2-oxoethoxy)-2,2-dimethyl-2H-chromene-6-carbaldehyde obtained in Preparation Example 2-1 was reacted by using the same method as in Preparation Example 1-2, thereby obtaining 1-(2-benzyloxy-4-ethoxyphenyl)-2-((6-hydroxymethyl-2,2-dimethyl-2H-chromene-5-yl)oxy)ethanone. $^1$H-NMR and $^{13}$C-NMR results for the obtained Compound are as follows.

$^1$H-NMR (CDCl3): 8.063 (d, 1H, J=8.8 Hz), 7.28~7.42 (b, 5H), 7.008 (d, 1H, J=8.0 Hz), 6.586 (d, 1H, J=8.8, 2.0 Hz), 6.532 (d, 1H, J=8.0 Hz), 6.503 (d, 1H, J=2.0 Hz), 6.383 (d, 1H, J=10.0 Hz) 5.464 (d, 1H, J=10.0 Hz), 5.130 (s, 2H), 5.092 (s, 2H), 4.522 (s, 2H), 4.078 (q, 2H, J=6.8 Hz), 3.502 (b, 1H), 1.424 (t, 3H, J=6.8 Hz), 1.367 (s, 6H).

$^{13}$C-NMR (CDCl3): 194.136, 164.785, 160.506, 154.276, 153.734, 135.384, 133.298, 130.280, 129.713, 128.772, 128.570, 127.905, 126.120, 117.735, 117.273, 114.343, 112.067, 106.684, 99.536, 80.734, 75.497, 70.927, 63.988, 61.479, 27.543, 14.594.

2-3: Preparation of 3-(2-(benzyloxy)-4-ethoxyphenyl)-8,8-dimethyl-2,8-dihydropyrano[2,3-f]chromene 1-(2-benzyloxy-4-ethoxyphenyl)-2((6-hydroxymethyl-2,2-dimethyl-2H-chromene-5-yl)oxy)ethanone obtained in Preparation Example 2-2 was reacted by using the same method as in Preparation Example 1-3, thereby obtaining 3-(2-benzyloxy-4-ethoxyphenyl)-8,8-dimethyl-2,8-dihydropyrano[2,3-f]chromene. $^1$H-NMR and $^{13}$C-NMR results for the obtained Compound are as follows.

$^1$H-NMR (CDCl3): 7.25~7.43 (m, 5H), 7.236 (d, 1H, J=8.8 Hz), 6.807 (d, 1H, J=8.0 Hz), 6.625 (d, 1H, J=10.0 Hz), 6.48-6.55 (m, 3H), 6.363 (d, 1H, J=8.0 Hz), 5.575 (d, 1H, J=10.0 Hz), 5.045 (s, 2H), 4.990 (s, 2H), 4.023 (q, 2H, J=6.8 Hz), 1.417 (s, 6H), 1.408 (t, 3H, J=6.8 Hz).

$^{13}$C-NMR (CDCl3): 159.850, 157.304, 153.334, 149.196, 136.543, 129.306, 129.250, 128.615, 128.602, 127.980, 127.406, 126.503, 121.516, 121.140, 116.980, 116.655, 109.523, 109.199, 105.670, 100.370, 76.037, 70.391, 68.508, 63.596, 27.829, 14.790.

Hereinafter, various 3-phenyl-2,8-dihydropyrano[2,3-f]chromene derivatives as in the following Table 1 were synthesized by using the same method as in Preparation Example 1.

TABLE 1

| Number of Preparation Example | Chemical structure | $^1$H-NMR, $^{13}$C-NMR (CDCl$_3$, δ) |
|---|---|---|
| 1 | 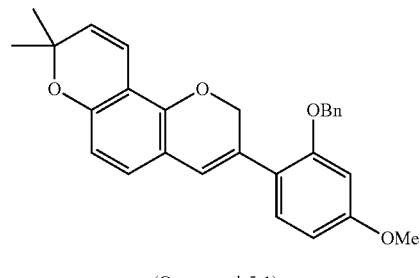<br>(Compound 5-1) | 7.25~7.43 (m, 5H), 7.248 (d, 1H, J = 8.8 Hz), 6.807 (d, 1H, J = 8.0 Hz), 6.625 (d, 1H, J = 10.0 Hz), 6.521 (s, 1H), 6.520 (d, 1H, J = 2.4 Hz), 6.512 (dd, 1H, J = 8.8, 2.4 Hz), 6.364 (d, 1H, J = 8.0 Hz), 5.573 (d, 1H, J = 10.0 Hz), 5.043 (s, 2H), 4.991 (s, 2H), 3.789 (s, 3H), 1.415 (s, 6H). 160.484, 157.297, 153.356, 149.196, 136.496, 129.335, 129.254, 128.603, 128.559, 127.994, 127.410, 126.520, 121.591, 121.314, 116.947, 116.641, 109.521, 109.211, 105.064, 99.963, 76.038, 70.414, 68.490, 55.402, 27.826. |

TABLE 1-continued

| Number of Preparation Example | Chemical structure | $^1$H-NMR, $^{13}$C-NMR (CDCl$_3$, δ) |
|---|---|---|
| 2 | 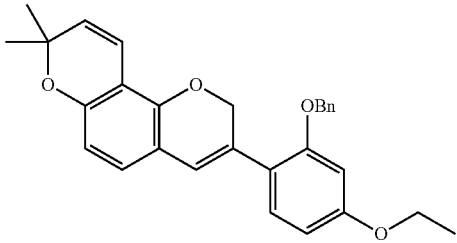 [SMILES: CCOc1ccc(C2=Cc3ccc4c(c3OC2)C=CC(C)(C)O4)c(OCc2ccccc2)c1]<br>(Compound 5-2) | 7.25~7.43 (m, 5H), 7.236 (d, 1H, J = 8.8 Hz), 6.807 (d, 1H, J = 8.0 Hz), 6.625 (d, 1H, J = 10.0 Hz), 6.48~6.55 (m, 3H), 6.363 (d, 1H, J = 8.0 Hz), 5.575 (d, 1H, J = 10.0 Hz), 5.045 (s, 2H), 4.990 (s, 2H), 4.023 (q, 2H, J = 6.8 Hz), 1.417 (s, 6H), 1.408 (t, 3H, J = 6.8 Hz). 159.850, 157.304, 153.334, 149.196, 136.543, 129.306, 129.250, 128.615, 128.602, 127.980, 127.406, 126.503, 121.516, 121.140, 116.980, 116.655, 109.523, 109.199, 105.670, 100.370, 76.037, 70.391, 68.508, 63.596, 27.829, 14.790. |
| 3 | 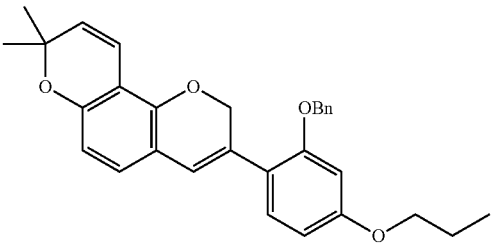 [SMILES: CCCOc1ccc(C2=Cc3ccc4c(c3OC2)C=CC(C)(C)O4)c(OCc2ccccc2)c1]<br>(Compound 5-3) | 7.25~7.43 (m, 5H), 7.233 (d, 1H, J = 8.8 Hz), 6.805 (d, 1H, J = 8.0 Hz), 6.624 (d, 1H, J = 10.0 Hz), 6.523 (d, 1H, J = 2.4 Hz), 6.516 (s, 1H), 6.505 (dd, 1H, J = 8.0, 2.4 Hz), 6.362 (d, 1H, J = 8.0 Hz), 5.573 (d, 1H, J = 10.0 Hz), 5.043 (s, 2H), 4.987 (s, 2H), 3.908 (t, 2H, J = 6.4 Hz), 1.798 (m, 2H), 1.415 (s, 6H), 1.032 (t, 3H, J = 7.2 Hz). 160.064, 157.309, 153.326, 149.193, 136.551, 129.292, 129.241, 128.629, 128.593, 127.975, 127.427, 126.500, 121.489, 121.085, 116.984, 116.658, 109.518, 109.194, 105.749, 100.360, 76.032, 70.407, 69.656, 68.517, 27.829, 22.535, 10.512. |
| 4 | 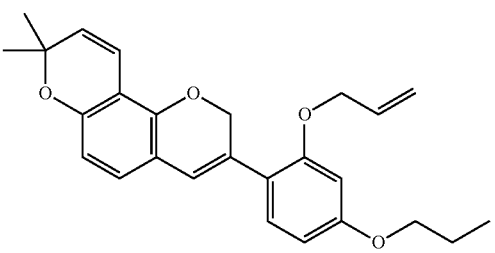 [SMILES: C=CCOc1cc(OCCC)ccc1C1=Cc2ccc3c(c2OC1)C=CC(C)(C)O3]<br>(Compound 5-4) | 7.216 (d, 1H, J = 8.0 Hz), 6.825 (d, 1H, J = 8.0 Hz), 6.653 (d, 1H, J = 10.0 Hz), 6.498 (s, 1H), 6.486 (dd, 1H, J = 8.0, 2.4 Hz), 6.453 (d, 1H, J = 2.4 Hz), 6.372 (d, 1H, J = 8.0 Hz), 6.026 (m, 1H), 5.589 (d, 1H, J = 10.0 Hz), 5.395 (m, 1H, J = 17.2 Hz, 1.6 Hz), 5.272 (m, 1H, J = 14.8, 1.6 Hz), 5.028 (s, 2H), 4.523 (m, 2H, J = 5.2, 1.6 Hz), 3.918 (t, 2H, J = 6.4 Hz), 1.810 (m, 2H), 1.425 (s, 6H), 1.040 (t, 3H, J = 7.2 Hz). 160.051, 157.161, 153.327, 149.178, 132.919, 129.275, 128.859, 126.494, 121.412, 120.975, 117.754, 116.993, 116.680, 109.562, 109.212, 105.663, 100.250, 76.029, 69.644, 69.184, 68.492, 27.813, 22.557, 10.514. |

TABLE 1-continued

| Number of Preparation Example | Chemical structure | $^1$H-NMR, $^{13}$C-NMR (CDCl$_3$, δ) |
|---|---|---|
| 5 | 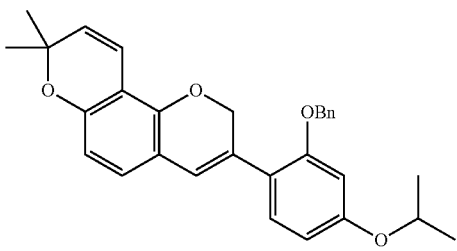 [SMILES: CC(C)Oc1ccc(C2=Cc3ccc4c(c3OC2)C=CC(C)(C)O4)c(OCc2ccccc2)c1]<br>(Compound 5-5) | 7.25~7.43 (m, 5H), 7.227 (d, 1H, J = 8.8 Hz), 6.805 (d, 1H, J = 8.0 Hz), 6.626 (d, 1H, J = 10.0 Hz), 6.519 (d, 1H, J = 2.4 Hz), 6.509 (s, 1H), 6.500 (dd, 1H, J = 8.8, 2.4 Hz), 6.362 (d, 1H, J = 8.0 Hz), 5.573 (d, 1H, J = 10.0 Hz), 5.035 (s, 2H), 4.991 (s, 2H), 4.526 (m, 1H, J = 6.0 Hz), 1.415 (s, 6H), 1.327 (d, 6H, J = 6.0 Hz).<br>158.785, 157.373, 153.323, 149.193, 136.580, 129.256, 129.229, 128.632, 128.585, 127.957, 127.399, 126.492, 121.475, 120.365, 116.986, 116.661, 109.513, 109.184, 106.974, 101.569, 76.025, 70.400, 69.997, 27.826, 22.021. |
| 6 | 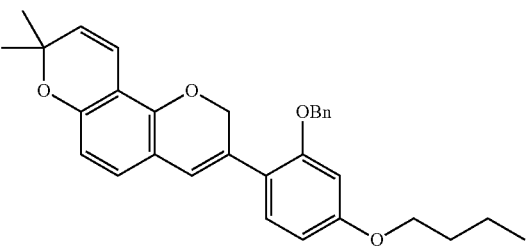 [SMILES: CCCCOc1ccc(C2=Cc3ccc4c(c3OC2)C=CC(C)(C)O4)c(OCc2ccccc2)c1]<br>(Compound 5-6) | 7.25~7.43 (m, 5H), 7.231 (d, 1H, J = 8.8 Hz), 6.803 (d, 1H, J = 8.0 Hz), 6.627 (d, 1H, J = 10.0 Hz), 6.520 (d, 1H, J = 2.4 Hz), 6.514 (s, 1H), 6.510 (dd, 1H, J = 8.8, 2.4 Hz), 6.361 (d, 1H, J = 8.0 Hz), 5.570 (d, 1H, J = 10.0 Hz), 5.040 (s, 2H), 4.985 (s, 2H), 3.947 (t, 2H, J = 8.4 Hz), 1.744 (m, 2H), 1.483 (m, 2H), 1.435 (s, 6H), 0.973 (t, 3H, J = 7.4 Hz).<br>160.078, 157.305, 153.323, 149.192, 136.552, 129.290, 129.245, 128.638, 128.596, 127.977, 127.429, 126.499, 121.486, 121.074, 116.988, 116.659, 109.520, 109.197, 105.728, 100.344, 76.036, 70.401, 68.518, 67.837, 31.261, 27.830, 19.224, 13.841. |
| 7 | 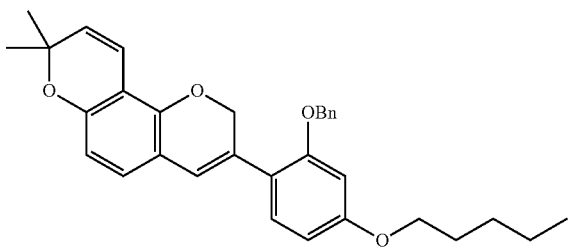 [SMILES: CCCCCOc1ccc(C2=Cc3ccc4c(c3OC2)C=CC(C)(C)O4)c(OCc2ccccc2)c1]<br>(Compound 5-7) | 7.25~7.43 (m, 5H), 7.246 (d, 1H, J = 8.8 Hz), 6.819 (d, 1H, J = 8.0 Hz), 6.638 (d, 1H, J = 10.0 Hz), 6.535 (d, 1H, J = 2.4 Hz), 6.529 (s, 1H), 6.518 (dd, 1H, J = 8.8, 2.4 Hz), 6.377 (d, 1H, J = 8.0 Hz), 5.586 (d, 1H, J = 10.0 Hz), 5.058 (s, 2H), 5.002 (s, 2H), 3.955 (t, 2H, J = 8.4 Hz), 1.790 (m, 2H), 1.37~1.44 (m, 4H), 1.430 (s, 6H), 0.949 (t, 3H, J = 7.4 Hz).<br>160.062, 157.296, 153.316, 149.183, 136.544, 129.276, 129.225, 128.616, 128.578, 127.961, 127.412, 126.491, 121.472, 121.052, 116.976, 116.651, 109.505, 109.184, 105.732, 100.346, 76.018, 70.393, 68.506, 68.133, 28.906, 28.156, 27.819, 22.430, 14.008. |

TABLE 1-continued

| Number of Preparation Example | Chemical structure | $^1$H-NMR, $^{13}$C-NMR (CDCl$_3$, δ) |
|---|---|---|
| 8 | 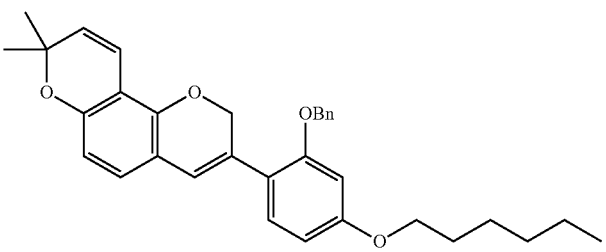 [SMILES: CCCCCCOc1ccc(C2=Cc3ccc4c(c3OC2)C=CC(C)(C)O4)c(OCc2ccccc2)c1]<br>(Compound 5-8) | 7.25~7.43 (m, 5H), 7.231 (d, 1H, J = 8.8 Hz), 6.803 (d, 1H, J = 8.0 Hz), 6.623 (d, 1H, J = 10.0 Hz), 6.520 (d, 1H, J = 2.4 Hz), 6.514 (s, 1H), 6.503 (dd, 1H, J = 8.8, 2.4 Hz), 6.361 (d, 1H, J = 8.0 Hz), 5.561 (d, 1H, J = 10.0 Hz), 5.041 (s, 2H), 4.986 (s, 2H), 3.939 (t, 2H, J = 8.4 Hz), 1.766 (m, 2H), 1.37~1.50 (m, 2H), 1.415 (s, 6H), 1.30~1.40 (m, 4H), 0.910 (t, 3H, J = 7.4 Hz).<br>160.062, 157.296, 153.316, 149.183, 136.544, 129.276, 129.225, 128.616, 128.578, 127.961, 127.412, 126.491, 121.472, 121.052, 116.976, 116.651, 109.505, 109.184, 105.732, 100.346, 76.018, 70.393, 68.506, 68.133, 28.906, 28.156, 27.819, 22.430, 14.008. |
| 9 | 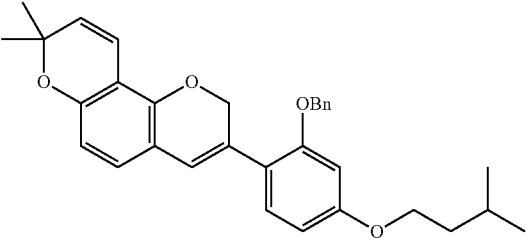 [SMILES: CC(C)CCOc1ccc(C2=Cc3ccc4c(c3OC2)C=CC(C)(C)O4)c(OCc2ccccc2)c1]<br>(Compound 5-9) | 7.25~7.43 (m, 5H), 7.231 (d, 1H, J = 8.4 Hz), 6.802 (d, 1H, J = 8.0 Hz), 6.623 (d, 1H, J = 10.0 Hz), 6.45~6.53 (m, 3H), 6.361 (d, 1H, J = 8.0 Hz), 5.578 (d, 1H, J = 10.0 Hz), 5.040 (s, 2H), 4.987 (s, 2H), 3.971 (t, 2H, J = 6.4 Hz), 1.828 (m, 1H), 1.663 (m, 2H), 1.414 (s, 6H), 0.959 (d, 6H, J = 6.8 Hz).<br>160.067, 157.311, 153.338, 149.202, 136.560, 129.287, 129.224, 128.620, 128.589, 127.972, 127.427, 126.504, 121.497, 121.088, 116.982, 116.666, 109.517, 109.195, 105.751, 100.389, 76.024, 70.416, 68.518, 66.509, 37.928, 27.834, 25.010, 22.565. |
| 10 | 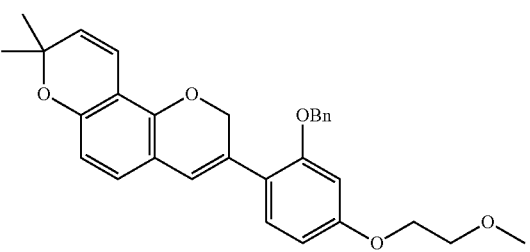<br>(Compound 5-10) | 7.25~7.43 (m, 5H), 7.235 (d, 1H, J = 8.4 Hz), 6.806 (d, 1H, J = 8.0 Hz), 6.627 (d, 1H, J = 10.0 Hz), 6.587 (d, 1H, J = 2.4 Hz), 6.520 (s, 1H), 6.517 (dd, 1H, J = 8.4, 2.4 Hz), 6.362 (d, 1H, J = 8.0 Hz), 5.578 (d, 1H, J = 10.0 Hz), 5.036 (s, 2H), 4.986 (s, 2H), 4.108 (t, 2H, J = 4.4 Hz), 3.740 (t, 2H, J = 4.4 Hz), 3.447 (s, 3H), 1.416 (s, 6H).<br>159.651, 157.280, 153.364, 149.209, 136.493, 129.249, 128.595, 128.520, 127.982, 127.387, 126.524, 121.640, 121.522, 116.945, 116.640, 109.516, 109.205, 105.609, 100.711, 76.041, 70.941, 70.405, 68.477, 67.356, 59.200, 27.830. |

TABLE 1-continued

| Number of Preparation Example | Chemical structure | $^1$H-NMR, $^{13}$C-NMR (CDCl$_3$, δ) |
|---|---|---|
| 11 | 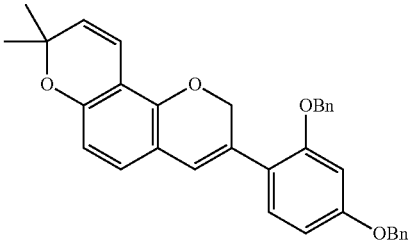<br>(Compound 5-11) | 7.28~7.43 (m, 10H), 7.241 (d, 1H, J = 8.0 Hz), 6.805 (d, 1H, J = 8.0 Hz), 6.628 (d, 1H, J = 10.0 Hz), 6.600 (d, 1H, J = 2.0 Hz), 6.585 (dd, 1H, J = 8.0, 2.0 Hz), 6.518 (s, 1H), 6.364 (d, 1H, J = 8.0 Hz), 5.573 (d, 1H, J = 10.0 Hz), 5.046 (s, 2H), 5.027 (s, 2H), 4.988 (s, 2H), 1.416 (s, 6H).<br>159.666, 157.308, 153.382, 149.212, 136.727, 136.473, 129.318, 129.262, 128.625, 128.615, 128.518, 128.071, 128.000, 127.519, 127.409, 126.537, 121.678, 121.555, 116.941, 116.647, 109.531, 109.221, 106.077, 100.760, 76.051, 70.421, 70.203, 68.481, 27.836. |
| 12 | 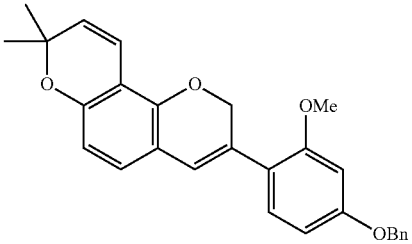 [SMILES: COc1cc(OCc2ccccc2)ccc1C1=Cc2ccc3c(c2OC1)C=CC(C)(C)O3]<br>(Compound 5-12) | 7.30~7.45 (m, 5H), 7.205 (d, 2H, J = 8.4 Hz), 6.817 (d, 1H, J = 8.4 Hz), 6.649 (d, 1H, J = 10.0 Hz), 6.551 (dd, 1H, J = 8.4, 2.4 Hz), 6.542 (d, 1H, J = 2.4 Hz), 6.485 (s, 1H), 6.370 (d, 1H, J = 8.4 Hz), 5.587 (d, 1H, J = 10.0 Hz), 5.065 (s, 3H), 5.004 (s, 3H), 3.781 (s, 3H), 1.420 (s, 6H).<br>159.793, 158.233, 153.368, 149.135, 136.749, 129.302, 129.223, 128.786, 128.618, 128.064, 127.530, 126.532, 121.573, 121.047, 116.894, 116.659, 109.584, 109.236, 105.488, 99.537, 76.032, 70.185, 68.353, 55.374, 27.786. |
| 13 | 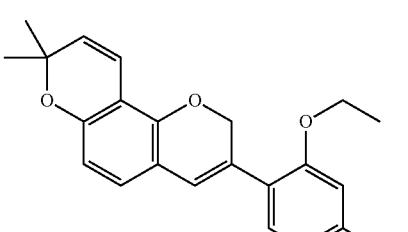<br>(Compound 5-13) | 7.30~7.45 (m, 5H), 7.215 (d, 2H, J = 8.4 Hz), 6.822 (d, 1H, J = 8.4 Hz), 6.652 (d, 1H, J = 10.0 Hz), 6.547 (dd, 1H, J = 8.4, 2.4 Hz), 6.512 (d, 1H, J = 2.4 Hz), 6.490 (s, 1H), 6.373 (d, 1H, J = 8.4 Hz), 5.587 (d, 1H, J = 10.0 Hz), 5.053 (s, 3H), 5.029 (s, H), 3.987 (q, 2H, J = 6.8 Hz), 1.423 (s, 6H), 1.391 (t, 3H, J = 6.8 Hz).<br>159.723, 157.565, 153.336, 149.196, 136.787, 129.292, 129.108, 128.970, 128.606, 128.039, 127.517, 126.519, 121.350, 121.326, 116.998, 116.667, 109.553, 109.223, 105.537, 100.155, 76.031, 70.158, 68.443, 63.757, 27.809, 14.730. |
| 14 | 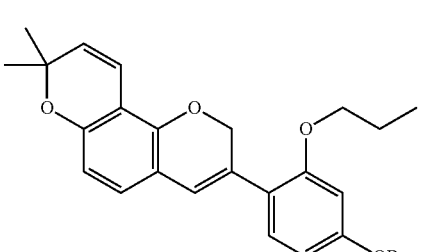<br>(Compound 5-14) | 7.30~7.45 (m, 5H), 7.222 (d, 2H, J = 8.4 Hz), 6.823 (d, 1H, J = 8.4 Hz), 6.659 (d, 1H, J = 10.0 Hz), 6.546 (dd, 1H, J = 8.4, 2.4 Hz), 6.522 (d, 1H, J = 2.4 Hz), 6.498 (s, 1H), 6.375 (d, 1H, J = 8.4 Hz), 5.589 (d, 1H, J = 10.0 Hz), 5.058 (s, 3H), 5.026 (s, 3H), 3.885 (t, 2H, J = 6.4 Hz), 1.794 (m, 2H), 1.425 (s, 6H), 1.024 (t, 3H, J = 7.2 Hz).<br>159.732, 157.763, 153.337, 149.218, 136.812, 129.281, 129.105, 128.897, 128.612, 128.043, 127.521, 126.521, 121.357, 121.261, 117.026, 116.683, 109.553, 109.219, 105.449, 100.108, 76.044, 70.167, 69.824, 68.513, 27.832, 22.517, 10.802. |

TABLE 1-continued

| Number of Preparation Example | Chemical structure | $^1$H-NMR, $^{13}$C-NMR (CDCl$_3$, δ) |
|---|---|---|
| 15 | 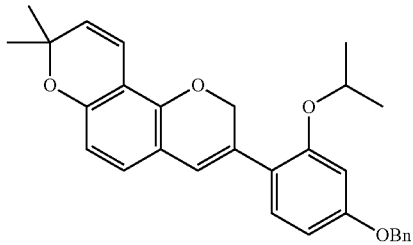 [SMILES: CC(C)Oc1cc(OCc2ccccc2)ccc1C1=Cc2ccc3c(c2OC1)C=CC(C)(C)O3]<br>(Compound 5-15) | 7.30~7.45 (m, 5H), 7.219 (d, 2H, J = 8.4 Hz), 6.824 (d, 1H, J = 8.4 Hz), 6.657 (d, 1H, J = 10.0 Hz), 6.547 (dd, 1H, J = 8.4, 2.4 Hz), 6.511 (d, 1H, J = 2.4 Hz), 6.467 (s, 1H), 6.374 (d, 1H, J = 8.4 Hz), 5.588 (d, 1H, J = 10.0 Hz), 5.053 (s, 3H), 5.013 (s, 3H), 4.501 (m, 1H, J = 6.0 Hz), 1.423 (s, 6H), 1.307 (d, 6H, J = 6.0 Hz).<br>159.646, 156.361, 153.301, 149.208, 136.818, 129.350, 129.296, 129.262, 128.618, 128.042, 127.522, 126.478, 122.274, 121.161, 117.059, 116.673, 109.558, 109.213, 105.618, 101.356, 76.025, 70.234, 70.192, 68.537, 27.815, 21.983. |
| 16 | 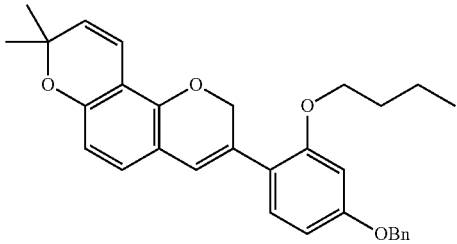 [SMILES: CCCCOc1cc(OCc2ccccc2)ccc1C1=Cc2ccc3c(c2OC1)C=CC(C)(C)O3]<br>(Compound 5-16) | 7.30~7.45 (m, 5H), 7.219 (d, 2H, J = 8.4 Hz), 6.823 (d, 1H, J = 8.4 Hz), 6.664 (d, 1H, J = 10.0 Hz), 6.540 (dd, 1H, J = 8.4, 2.4 Hz), 6.527 (d, 1H, J = 2.4 Hz), 6.496 (s, 1H), 6.375 (d, 1H, J = 8.4 Hz), 5.589 (d, 1H, J = 10.0 Hz), 5.056 (s, 3H), 5.016 (s, 3H), 3.921 (t, 2H, J = 6.4 Hz), 1.751 (m, 2H), 1.467 (m, 2H), 1.426 (s, 6H), 9.55 (t, 3H, J = 7.2 Hz).<br>159.721, 157.763, 153.329, 149.217, 136.806, 129.263, 129.088, 128.853, 128.598, 128.029, 127.512, 126.517, 121.339, 121.254, 117.018, 116.678, 109.536, 109.211, 105.409, 100.094, 76.034, 70.158, 68.488, 67.934, 31.204, 27.830, 19.359, 13.808. |
| 17 | 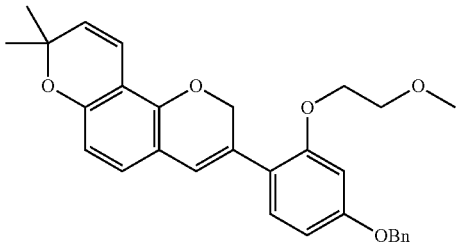<br>(Compound 5-17) | 7.30~7.45 (m, 5H), 7.222 (d, 2H, J = 8.4 Hz), 6.820 (d, 1H, J = 8.4 Hz), 6.662 (d, 1H, J = 10.0 Hz), 6.571 (dd, 1H, J = 8.4, 2.4 Hz), 6.534 (d, 1H, J = 2.4 Hz), 6.516 (s, 1H), 6.372 (d, 1H, J = 8.4 Hz), 5.588 (d, 1H, J = 10.0 Hz), 5.057 (s, 3H), 5.030 (s, 3H), 4.075 (t, 2H, J = 4.8 Hz), 3.716 (t, 2H, J = 4.8 Hz), 3.417 (s, 6H), 1.426 (s, 6H).<br>159.631, 157.399, 153.348, 149.248, 136.737, 129.240, 129.175, 128.634, 128.613, 128.053, 127.506, 126.530, 121.569 121.476, 117.000, 116.693, 109.534, 109.191, 106.098, 100.507, 76.037, 70.856, 70.180, 68.405, 67.595, 59.105, 27.827. |

TABLE 1-continued

| Number of Preparation Example | Chemical structure | $^1$H-NMR, $^{13}$C-NMR (CDCl$_3$, δ) |
|---|---|---|
| 18 | 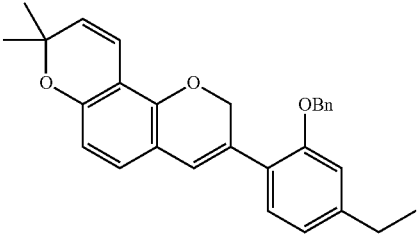 [SMILES: CCc1ccc(C2=Cc3ccc4c(c3OC2)C=CC(C)(C)O4)c(OCc2ccccc2)c1]<br>(Compound 5-18) | 7.30~7.45 (m, 5H), 7.269 (d, 2H, J = 7.2 Hz), 6.848 (d, 1H, J = 7.2 Hz), 6.831 (d, 1H, J = 8.0 Hz), 6.821 (s, 1H), 6.647 (d, 1H, J = 10.0 Hz), 6.582 (s, 1H), 6.385 (d, 1H, J = 8.0 Hz), 5.591 (d, 1H, J = 10.0 Hz), 5.091 (s, 2H), 5.029 (s, 2H), 2.661 (q, 2H, J = 7.6 Hz), 1.437 (s, 6H), 1.258 (t, 3H, J = 7.6 Hz). 156.345, 153.498, 149.352, 145.527, 136.824, 129.242, 128.850, 128.721, 128.572, 127.924, 127.459, 126.647, 125.831, 122.230, 120.671, 116.927, 116.664, 112.085, 109.547, 109.230, 76.069, 70.449, 68.484, 28.892, 27.856, 15.468. |
| 19 | 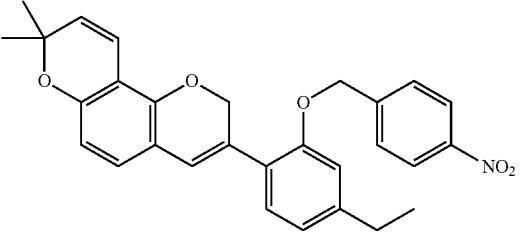 [SMILES: CCc1ccc(C2=Cc3ccc4c(c3OC2)C=CC(C)(C)O4)c(OCc2ccc([N+](=O)[O-])cc2)c1]<br>(Compound 5-19) | 8.241 (d, 2H, J = 8.8 Hz), 7.794 (d, 2H, J = 8.8 Hz), 7.268 (d, 1H, J = 8.0 Hz), 6.882 (d, 1H, J = 8.0 Hz), 6.837 (d, 1H, J = 8.0 Hz), 6.763 (s, 1H), 6.635 (d, 1H, J = 10.0 Hz), 6.571 (s, 1H), 6.395 (d, 1H, J = 8.0 Hz), 5.605 (d, 1H, J = 10.0 Hz), 5.190 (s, 2H), 5.010 (s, 2H), 2.650 (q, 2H, J = 7.6 Hz), 1.436 (s, 6H), 1.243 (t, 3H, J = 7.6 Hz). 155.619, 153.656, 149.223, 147.562, 145.681, 144.206, 129.448, 129.089, 128.357, 127.662, 126.670, 125.875, 123.867, 122.720, 121.343, 116.696, 116.482, 112.132, 109.596, 109.411, 76.156, 69.267, 68.325, 28.849, 27.860, 15.464. |
| 20 | 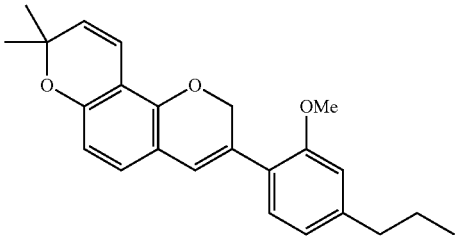<br>(Compound 5-20) | 7.203 (d, 1H, J = 7.6 Hz), 6.827 (d, 1H, J = 8.4 Hz), 6.784 (dd, 1H, J = 7.6, 1.2 Hz), 6.703 (d, 1H, J = 1.2 Hz), 6.653 (d, 1H, J = 10.0 Hz), 6.528 (s, 1H), 6.372 (d, 1H, J = 8.4 Hz), 5.588 (d, 1H, J = 10.0 Hz), 5.027 (s, 2H), 3.815 (s, 3H), 2.588 (t, 2H, J = 7.6 Hz), 1.660 (m, 2H, J = 7.6 Hz), 1.422 (s, 6H), 0.965 (t, 3H, J = 7.6 Hz). 157.051, 153.435, 149.241, 144.030, 129.276, 129.163, 128.480, 126.617, 125.217, 122.038, 120.889, 116.882, 116.666, 111.117, 109.585, 109.230, 76.031, 68.337, 55.302, 38.117, 27.784, 24.503, 13.887. |
| 21 | 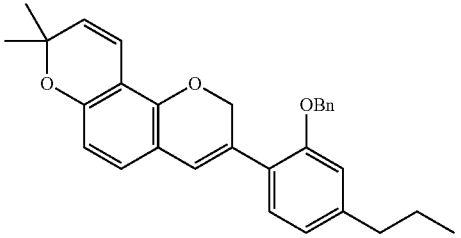 [SMILES: CCCc1ccc(C2=Cc3ccc4c(c3OC2)C=CC(C)(C)O4)c(OCc2ccccc2)c1]<br>(Compound 5-21) | 7.30~7.45 (m, 5H), 7.252 (d, 1H, J = 7.2 Hz), 6.825 (d, 1H, J = 7.2 Hz), 6.820 (d, 1H, J = 8.0 Hz), 6.793 (s, 1H), 6.642 (d, 1H, J = 10.0 Hz), 6.580 (s, 1H), 6.370 (d, 1H, J = 8.0 Hz), 5.587 (d, 1H, J = 10.0 Hz), 5.082 (s, 2H), 5.025 (s, 2H), 2.589 (t, 2H, J = 7.6 Hz), 1.655 (m, 2H, J = 7.6 Hz), 1.433 (s, 6H), 0.958 (t, 3H, J = 7.6 Hz). 156.249, 153.492, 149.357, 143.970, 136.831, 129.235, 128.862, 128.593, 128.565, 127.914, 127.456, 126.642, 125.820, 122.222, 121.337, 116.936, 116.668, 112.668, 109.542, 109.224, 76.066, 70.449, 68.486, 38.060, 27.859, 24.436, 13.828. |

TABLE 1-continued

| Number of Preparation Example | Chemical structure | $^1$H-NMR, $^{13}$C-NMR (CDCl$_3$, δ) |
|---|---|---|
| 22 | (Compound 5-22) | 7.343 (s, 4H), 7.239 (d, 1H, J = 8.0 Hz), 6.819 (d, 2H, J = 8.0 Hz), 6.745 (s, 1H), 6.629 (d, 1H, J = 10.0 Hz), 6.550 (s, 1H), 6.374 (d, 1H, J = 8.0 Hz), 5.587 (d, 1H, J = 10.0 Hz), 5.031 (s, 2H), 4.981 (s, 2H), 2.574 (t, 2H, J = 7.2 Hz), 1.639 (m, 2H), 1.425 (s, 6H), 0.945 (t, 3H, J = 7.2 Hz). |
| 23 | (Compound 5-23) | 7.472 (d, 1H, J = 8.0 Hz), 7.421 (d, 1H, J = 2.0 Hz), 7.250 (dd, 1H, J = 8.0, 2.0 Hz), 7.238 (d, 1H, J = 8.0 Hz), 6.834 (d, 1H, J = 8.0 Hz), 6.828 (d, 1H, J = 8.0 Hz), 6.744 (s, 1H), 6.636 (d, 1H, J = 10.0 Hz), 6.557 (s, 1H), 6.381 (d, 1H, J = 8.0 Hz), 5.595 (d, 1H, J = 10.0 Hz), 5.123 (s, 2H), 5.000 (s, 2H), 2.582 (t, 2H, J = 7.2 Hz), 1.643 (m, 2H), 1.429 (s, 6H), 0.948 (t, 3H, J = 7.2 Hz). |
| 24 | (Compound 5-24) | 7.289 (d, 2H, J = 8.0 Hz), 7.234 (d, 1H, J = 8.4 Hz), 7.170 (d, 2H, J = 8.0 Hz), 6.809 (d, 1H, J = 8.4 Hz), 6.793 (dd, 1H, J = 8.4, 2.0 Hz), 6.778 (d, 1H, J = 2.0 Hz), 6.625 (d, 1H, J = 10.0 Hz), 6.548 (s, 1H), 6.362 (d, 1H, J = 8.4 Hz), 5.571 (d, 1H, J = 10.0 Hz), 5.012 (s, 2H), 4.993 (s, 2H), 2.572 (t, 2H, J = 7.6 Hz), 2.349 (s, 3H), 1.642 (m, 2H, J = 7.6 Hz), 1.415 (s, 6H), 0.946 (t, 3H, J = 7.2 Hz). 156.286, 153.417, 149.335, 143.948, 137.651, 133.719, 129.221, 128.974, 128.524, 127.591, 126.612, 125.784, 122.081, 121.208, 116.958, 116.667, 112.522, 109.514, 109.186, 76.040, 70.301, 68.478, 38.060, 27.829, 24.468, 13.854. |
| 25 | (Compound 5-25) | 8.231 (d, 2H, J = 8.8 Hz), 7.587 (d, 2H, J = 8.8 Hz), 7.250 (d, 1H, J = 8.0 Hz), 6.847 (d, 1H, J = 8.0 Hz), 6.820 (d, 1H, J = 8.0 Hz), 6.728 (s, 1H), 6.629 (d, 1H, J = 10.0 Hz), 6.566 (s, 1H), 6.387 (d, 1H, J = 8.0 Hz), 5.597 (d, 1H, J = 10.0 Hz), 5.176 (s, 2H), 5.003 (s, 2H), 2.572 (t, 2H, J = 7.2 Hz), 1.630 (m, 2H), 1.428 (s, 6H), 0.938 (t, 3H, J = 7.6 Hz). 155.522, 153.649, 149.224, 147.548, 144.214, 144.120, 129.433, 128.954, 128.364, 127.656, 126.663, 125.854, 123.850, 122.705, 121.992, 116.702, 116.485, 112.695, 109.588, 109.399, 76.144, 69.253, 68.321, 37.985, 27.860, 24.427, 13.791. |

TABLE 1-continued

| Number of Preparation Example | Chemical structure | $^1$H-NMR, $^{13}$C-NMR (CDCl$_3$, δ) |
|---|---|---|
| 26 | 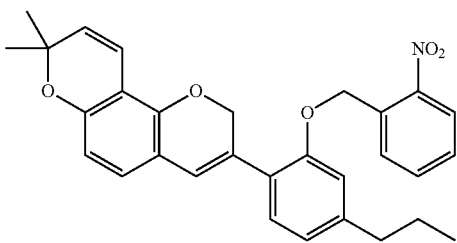 [SMILES: CCCc1ccc(C2=Cc3ccc4c(c3OC2)C=CC(C)(C)O4)c(OCc2ccccc2[N+](=O)[O-])c1]<br>(Compound 5-26) | 8.172 (d, 1H, J = 8.0 Hz), 7.895 (d, 1H, J = 8.0 Hz), 7.658 (t, 1H, J = 8.0 Hz), 7.478 (t, 1H, J = 8.0 Hz), 7.243 (d, 1H, J = 8.0 Hz), 6.848 (d, 2H, J = 8.0 Hz), 6.752 (s, 1H), 6.648 (d, 1H, J = 10.0 Hz), 6.586 (s, 1H), 6.392 (d, 1H, J = 8.0 Hz), 5.599 (d, 1H, J = 10.0 Hz), 5.510 (s, 2H), 5.042 (s, 2H), 2.569 (t, 2H, J = 7.2 Hz), 1.625 (m, 2H), 1.433 (s, 6H), 0.936 (t, 3H, J = 7.6 Hz). 155.504, 153.590, 149.288, 146.781, 144.288, 134.182, 133.766, 129.380, 128.983, 128.630, 128.479, 128.311, 126.677, 125.737, 124.973, 122.756, 121.887, 116.793, 116.543, 112.905, 109.587, 109.346, 76.121, 68.356, 67.312, 37.992, 27.872, 24.480, 13.801. |
| 27 | 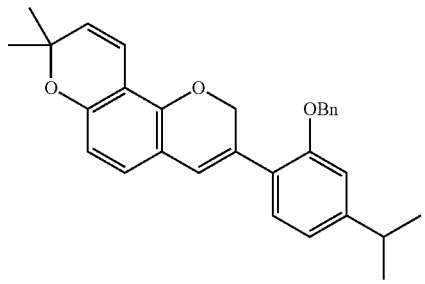 [SMILES: CC(C)c1ccc(C2=Cc3ccc4c(c3OC2)C=CC(C)(C)O4)c(OCc2ccccc2)c1]<br>(Compound 5-27) | 7.30~7.45 (m, 5H), 7.281 (d, 1H, J = 7.2 Hz), 6.877 (d, 1H, J = 7.2 Hz), 6.843 (s, 1H), 6.833 (d, 1H, J = 8.0 Hz), 6.646 (d, 1H, J = 10.0 Hz), 6.582 (s, 1H), 6.385 (d, 1H, J = 8.0 Hz), 5.593 (d, 1H, J = 10.0 Hz), 5.096 (s, 2H), 5.031 (s, 2H), 2.910 (m, 1H, J = 7.0 Hz), 1.436 (s, 6H), 1.267 (d, 6H, J = 7.0 Hz). 156.295, 153.471, 150.198, 149.340, 136.814, 129.240, 128.873, 128.691, 128.564, 127.924, 127.501, 126.636, 125.938, 122.224, 119.160, 116.925, 116.659, 110.754, 109.543, 109.216, 76.062, 70.446, 68.453, 34.166, 27.840, 23.914. |
| 28 | 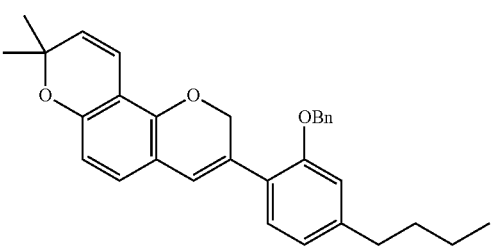 [SMILES: CCCCc1ccc(C2=Cc3ccc4c(c3OC2)C=CC(C)(C)O4)c(OCc2ccccc2)c1]<br>(Compound 5-28) | 7.30~7.45 (m, 5H), 7.264 (d, 1H, J = 7.2 Hz), 6.840 (d, 1H, J = 7.2 Hz), 6.832 (d, 1H, J = 8.0 Hz), 6.804 (s, 1H), 6.654 (d, 1H, J = 10.0 Hz), 6.590 (s, 1H), 6.394 (d, 1H, J = 8.0 Hz), 5.598 (d, 1H, J = 10.0 Hz), 5.091 (s, 2H), 5.036 (s, 2H), 2.622 (t, 2H, J = 7.6 Hz), 1.623 (m, 2H), 1.444 (s, 6H), 1.375 (m, 2H), 0.954 (t, 3H, J = 7.6 Hz). 156.212, 153.455, 149.331, 144.180, 136.791, 129.229, 128.867, 128.588, 128.553, 127.902, 127.449, 126.626, 125.728, 122.179, 121.252, 116.929, 116.652, 112.540, 109.529, 109.213, 76.054, 70.380, 68.463, 35.669, 33.512, 27.837, 22.345, 13.954. |

TABLE 1-continued

| Number of Preparation Example | Chemical structure | $^1$H-NMR, $^{13}$C-NMR (CDCl$_3$, δ) |
|---|---|---|
| 29 | 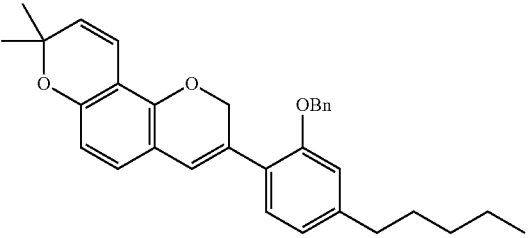 [SMILES: CCCCCc1ccc(C2=Cc3ccc4c(c3OC2)C=CC(C)(C)O4)c(OCc2ccccc2)c1]<br>(Compound 5-29) | 7.30~7.45 (m, 5H), 7.250 (d, 1H, J = 7.2 Hz), 6.825 (d, 1H, J = 7.2 Hz), 6.816 (d, 1H, J = 8.0 Hz), 6.787 (s, 1H), 6.635 (d, 1H, J = 10.0 Hz), 6.574 (s, 1H), 6.375 (d, 1H, J = 8.0 Hz), 5.585 (d, 1H, J = 10.0 Hz), 5.080 (s, 2H), 5.018 (s, 2H), 2.598 (t, 2H, J = 7.6 Hz), 1.618 (m, 2H), 1.428 (s, 6H), 1.325 (m, 4H), 0.906 (t, 3H, J = 6.8 Hz).<br>156.212, 153.449, 149.330, 144.237, 136.793, 129.239, 128.881, 128.595, 128.561, 127.912, 127.452, 126.627, 125.728, 122.179, 121.238, 116.934, 116.651, 112.504, 109.533, 109.215, 76.059, 70.372, 68.464, 35.956, 31.479, 31.068, 27.837, 22.538, 14.036. |
| 30 | 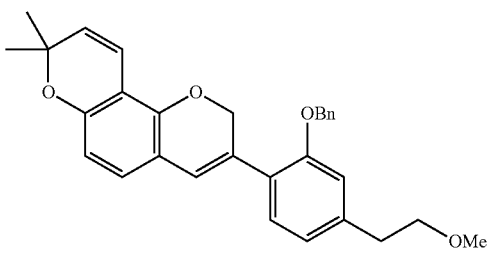 [SMILES: COCCc1ccc(C2=Cc3ccc4c(c3OC2)C=CC(C)(C)O4)c(OCc2ccccc2)c1]<br>(Compound 5-30) | 7.30~7.45 (m, 5H), 7.271 (d, 1H, J = 7.2 Hz), 6.860 (d, 1H, J = 7.2 Hz), 6.851 (s, 1H), 6.833 (d, 1H, J = 8.0 Hz), 6.638 (d, 1H, J = 10.0 Hz), 6.577 (s, 1H), 6.383 (d, 1H, J = 8.0 Hz), 5.592 (d, 1H, J = 10.0 Hz), 5.085 (s, 2H), 5.016 (s, 2H), 3.616 (t, 2H, J = 6.8 Hz), 3.368 (s, 3H), 2.887 (t, 2H, J = 6.8 Hz), 1.433 (s, 6H).<br>156.258, 153.509, 149.343, 140.209, 136.709, 129.253, 128.726, 128.566, 127.931, 127.447, 126.663, 126.362, 122.375, 121.594, 116.867, 116.621, 112.952, 109.534, 109.237, 76.068, 73.341, 70.385, 68.401, 58.694, 36.173, 27.835. |
| 31 | 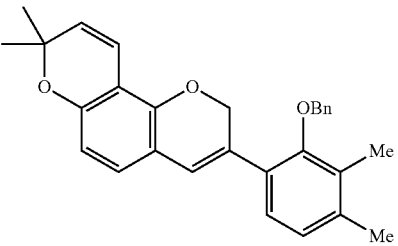 [SMILES: Cc1ccc(C2=Cc3ccc4c(c3OC2)C=CC(C)(C)O4)c(OCc2ccccc2)c1C]<br>(Compound 5-31) | 7.30~7.45 (m, 5H), 7.100 (d, 1H, J = 8.0 Hz), 6.981 (d, 1H, J = 8.0 Hz), 6.851 (d, 1H, J = 8.0 Hz), 6.672 (d, 1H, J = 10.0 Hz), 6.643 (s, 1H), 6.409 (d, 1H, J = 8.0 Hz), 5.613 (d, 1H, J = 10.0 Hz), 5.078 (s, 2H), 4.770 (s, 2H), 2.306 (s, 3H), 2.230 (s, 3H), 1.455 (s, 6H).<br>154.695, 153.636, 149.312, 138.313, 137.128, 129.312, 128.827, 128.679, 128.498, 128.425, 128.176, 127.986, 126.703, 126.018, 125.858, 122.605, 116.661, 116.609, 109.601, 109.266, 76.131, 74.894, 68.268, 27.878, 20.124, 12.428. |
| 32 | 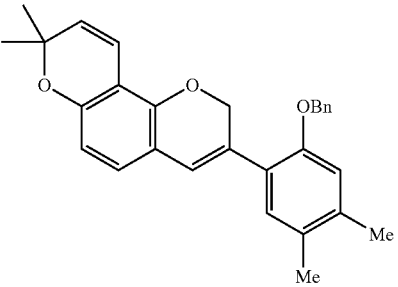 [SMILES: Cc1cc(OCc2ccccc2)c(C2=Cc3ccc4c(c3OC2)C=CC(C)(C)O4)cc1C]<br>(Compound 5-32) | 7.30~7.45 (m, 5H), 7.125 (s, 1H), 6.838 (d, 1H, J = 8.0 Hz), 6.780 (s, 1H), 6.652 (d, 1H, J = 10.0 Hz), 6.581 (s, 1H), 6.390 (d, 1H, J = 8.0 Hz), 5.597 (d, 1H, J = 10.0 Hz), 5.061 (s, 2H), 5.033 (s, 2H), 2.275 (s, 3H), 2.237 (s, 3H), 1.438 (s, 6H).<br>154.361, 153.428, 149.310, 137.257, 136.995, 129.915, 129.224, 129.077, 128.861, 128.541, 127.843, 127.370, 126.605, 125.653, 122.002, 116.932, 116.666, 114.121, 109.528, 109.200, 76.049, 70.647, 68.528, 27.838, 19.986, 18.803. |

TABLE 1-continued

| Number of Preparation Example | Chemical structure | $^1$H-NMR, $^{13}$C-NMR (CDCl$_3$, δ) |
|---|---|---|
| 33 | 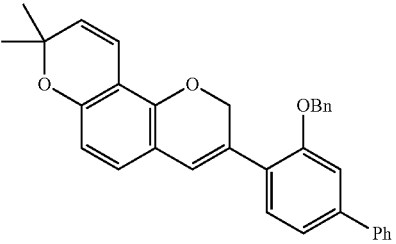 [SMILES: CC1(C)C=Cc2c(ccc3c2OCC(c2ccc(-c4ccccc4)cc2OCc2ccccc2)=C3)O1]<br>(Compound 5-33) | 7.598 (d, 2H, J = 7.2 Hz), 7.30~7.50 (m, 9H), 7.246 (d, 1H, J = 7.2 Hz), 7.202 (s, 1H), 6.875 (d, 1H, J = 7.2 Hz), 6.688 (s, 1H), 6.676 (d, 1H, J = 10.0 Hz), 6.422 (d, 1H, J = 8.0 Hz), 5.818 (d, 1H, J = 10.0 Hz), 5.176 (s, 2H), 5.091 (s, 2H), 1.461 (s, 6H). 156.596, 153.662, 149.427, 141.997, 140.685, 136.574, 129.294, 129.086, 128.793, 128.627, 128.339, 128.034, 127.496, 127.344, 127.004, 126.802, 122.871, 120.081, 116.828, 116.601, 111.175, 109.560, 109.334, 76.121, 70.551, 68.363, 27.860. |
| 34 | 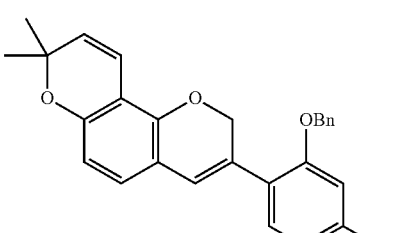<br>(Compound 5-34) | 7.30~7.45 (m, 5H), 7.273 (d, 1H, J = 7.2 Hz), 7.140 (t, 1H, J = 7.2 Hz), 7.030 (d, 2H, J = 7.2 Hz), 6.835 (d, 1H, J = 8.0 Hz), 6.659 (d, 1H, J = 2.4 Hz), 6.641 (d, 1H, J = 10.0 Hz), 6.587 (dd, 1H, J = 8.0, 2.4 Hz), 6.562 (s, 1H), 6.386 (d, 1H, J = 8.0 Hz), 5.595 (d, 1H, J = 10.0 Hz), 5.021 (s, 2H), 5.018 (s, 2H), 1.433 (s, 6H). 158.032, 157.286, 156.689, 153.527, 149.284, 136.226, 129.791, 129.487, 129.306, 128.620, 128.283, 128.044, 127.691, 127.471, 126.652, 123.538, 123.433, 122.286, 119.085, 116.823, 116.603, 110.737, 109.552, 109.291, 76.098, 70.450, 68.380, 27.846. |
| 35 | 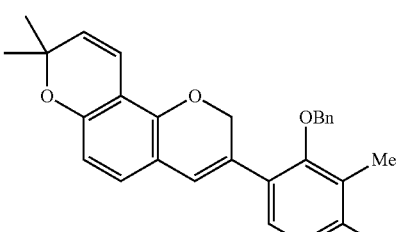<br>(Compound 5-35) | 7.30~7.45 (m, 10H), 7.133 (d, 2H, J = 8.4 Hz), 6.840 (d, 1H, J = 8.0 Hz), 6.750 (d, 1H, J = 8.4 Hz), 6.669 (d, 1H, 10.0 Hz), 6.605 (s, 1H), 6.405 (d, 1H, J = 8.0 Hz), 5.613 (d, 1H, J = 10.0 Hz), 5.115 (s, 2H), 5.062 (s, 2H), 4.796 (s, 2H), 2.247 (s, 3H), 1.426 (s, 6H). 157.621, 155.594, 153.525, 149.214, 137.161, 137.008, 129.322, 128.594, 128.539, 128.435, 128.255, 128.040, 127.844, 127.101, 126.590, 126.327, 125.439, 122.095, 120.918, 116.754, 116.618, 109.597, 109.244, 107.807, 76.116, 74.951, 70.207, 68.309, 27.873, 9.441. |
| 36 | 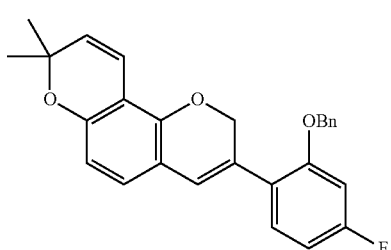<br>(Compound 5-36) | 7.30~7.42 (m, 5H), 7.267 (dd, 1H, J = 8.8, 6.8 Hz), 6.821 (d, 1H, J = 8.4 Hz), 6.65~6.71 (m, 2H), 6.619 (d, 1H, J = 10.0 Hz), 6.524 (s, 1H), 6.375 (d, 1H, J = 8.4 Hz), 5.581 (d, 1H, J = 10.0 Hz), 5.041 (s, 2H), 4.972 (s, 2H), 1.419 (s, 6H). 163.801, 162.400, 157.261, 153.659, 149.306, 135.951, 129.599, 129.346, 128.695, 128.191, 127.898, 127.405, 126.733, 124.477, 122.747, 116.650, 116.545, 109.455, 107.590, 100.416, 76.129, 70.638, 68.260, 27.729. |

TABLE 1-continued

| Number of Preparation Example | Chemical structure | $^1$H-NMR, $^{13}$C-NMR (CDCl$_3$, δ) |
|---|---|---|
| 37 | 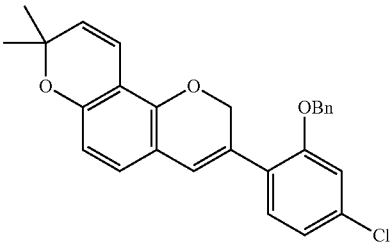 [SMILES: CC1(C)C=Cc2c(ccc3c2OCC(c2ccc(Cl)cc2OCc2ccccc2)=C3)O1]<br>(Compound 5-37) | 7.30~7.42 (m, 5H), 7.244 (d, 1H, J = 8.0 Hz), 6.961 (dd, 1H, J = 8.0, 2.0 Hz), 6.943 (d, 1H, J = 2.0 Hz), 6.822 (d, 1H, J = 8.4 Hz), 6.611 (d, 1H, J = 10.0 Hz), 6.564 (s, 1H), 6.372 (d, 1H, J = 8.4 Hz), 5.581 (d, J = 10.0 Hz), 5.050 (s, 2H), 4.962 (s, 2H), 1.419 (s, 6H). 156.753, 153.804, 149.400, 135.940, 134.044, 129.483, 129.371, 128.700, 128.225, 127.620, 127.483, 127.015, 126.856, 123.236, 121.313, 116.580, 116.509, 112.791, 109.567, 109.421, 76.177, 70.718, 68.140, 27.871. |
| 38 | 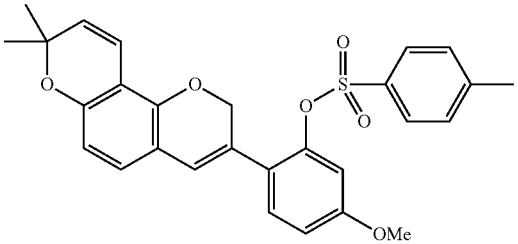<br>(Compound 5-38) | 7.556 (d, 2H, J = 8.0 Hz), 7.068 (d, 1H, J = 8.0 Hz), 7.029 (d, 2H, J = 8.0 Hz), 6.943 (d, 1H, J = 2.8 Hz), 6.805 (dd, 1H, J = 8.0, 2.8 Hz), 6.632 (d, 1H, J = 8.0 Hz), 6.602 (d, 1H, J = 10.0 Hz), 6.353 (d, 1H, J = 8.0 Hz), 5.954 (s, 1H), 5.612 (d, 1H, J = 10.0 Hz), 4.716 (s, 2H), 3.822 (s, 3H), 2.277 (s, 3H), 1.450 (s, 6H). 159.744, 153.799, 148.644, 147.537, 145.335, 132.181, 129.582, 129.482, 129.462, 128.463, 126.541, 125.429, 124.620, 123.330, 116.449, 116.134, 113.703, 109.478, 109.368, 109.202, 76.191, 67.578, 55.652, 27.851, 21.610. |
| 39 | 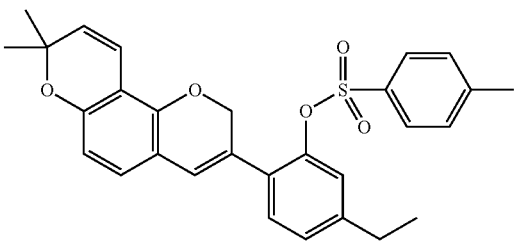<br>(Compound 5-39) | 7.544 (d, 2H, J = 8.0 Hz), 7.202 (s, 1H), 7.079 (s, 2H), 7.026 (d, 2H, J = 8.0 Hz), 6.644 (d, 1H, J = 8.0 Hz), 6.603 (d, 1H, J = 10.0 Hz), 6.356 (d, 1H, J = 8.0 Hz), 6.015 (s, 1H), 5.618 (d, 1H, J = 10.0 Hz), 4.743 (s, 2H), 2.669 (q, 2H, J = 7.6 Hz), 2.277 (s, 3H), 1.451 (s, 6H), 1.240 (t, 3H, J = 7.6 Hz). 153.897, 148.748, 146.776, 145.591, 145.213, 132.320, 129.511, 129.444, 128.889, 128.441, 126.962, 126.666, 125.673, 123.839, 123.339, 116.440, 116.090, 109.485, 109.223, 76.209, 67.526, 28.311, 27.853, 21.604, 15.134. |
| 40 | 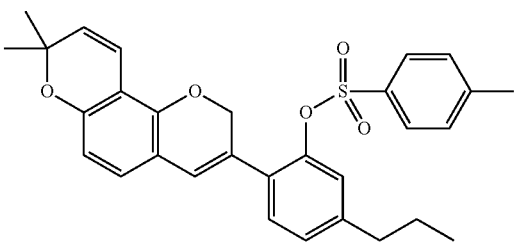<br>(Compound 5-40) | 7.535 (d, 2H, J = 8.0 Hz), 7.188 (s, 1H), 7.061 (s, 2H), 7.023 (d, 2H, J = 8.0 Hz), 6.644 (d, 1H, J = 8.0 Hz), 6.606 (d, 1H, J = 10.0 Hz), 6.357 (d, 1H, J = 8.0 Hz), 6.012 (s, 1H), 5.618 (d, 1H, J = 10.0 Hz), 4.746 (s, 2H), 2.601 (t, 2H, J = 7.6 Hz), 2.277 (s, 3H), 1.643 (m, 2H, J = 7.6 Hz), 1.451 (s, 6H), 0.948 (t, 3H, J = 7.6 Hz). 153.900, 148.761, 146.696, 145.202, 144.065, 132.281, 129.525, 129.439, 128.779, 128.446, 127.572, 126.667, 125.683, 123.889, 123.846, 116.445, 116.103, 109.489, 109.227, 76.217, 67.528, 37.349, 27.857, 24.165, 21.605, 13.654. |

TABLE 1-continued

| Number of Preparation Example | Chemical structure | $^{1}$H-NMR, $^{13}$C-NMR (CDCl$_3$, δ) |
|---|---|---|
| 41 | 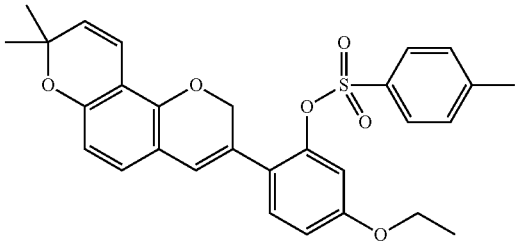(Compound 5-41) | 7.546 (d, 2H, J = 8.0 Hz), 7.042 (d, 1H, J = 8.0 Hz), 7.020 (d, 2H, J = 8.0 Hz), 6.943 (d, 1H, J = 2.4 Hz), 6.787 (dd, 1H, J = 8.0, 2.4 Hz), 6.625 (d, 1H, J = 8.0 Hz), 6.602 (d, 1H, J = 10.0 Hz), 6.351 (d, 1H, J = 8.0 Hz), 5.937 (s, 1H), 5.617 (d, 1H, J = 10.0 Hz), 4.707 (s, 2H), 4.042 (q, 2H, J = 6.8 Hz), 2.273 (s, 3H), 1.450 (s, 6H), 1.429 (t, 3H, J = 6.8 Hz). 159.115, 153.775, 148.633, 147.492, 145.304, 132.172, 129.524, 129.465, 128.455, 126.521, 125.478, 124.390, 123.236, 116.461, 116.161, 114.219, 109.834, 109.475, 109.187, 76.185, 67.579, 63.966, 27.849, 21.607, 14.617. |
| 42 | 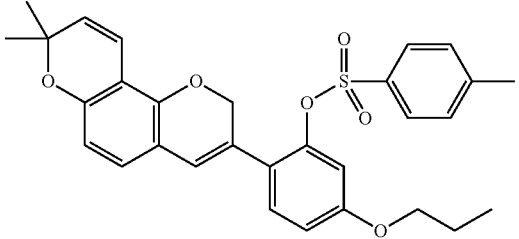(Compound 5-42) | 7.551 (d, 2H, J = 8.0 Hz), 7.042 (d, 1H, J = 8.0 Hz) , 7.022 (d, 2H, J = 8.0 Hz), 6.936 (d, 1H, J = 2.4 Hz), 6.794 (dd, 1H, J = 8.0, 2.4 Hz), 6.625 (d, 1H, J = 8.0 Hz), 6.602 (d, 1H, J = 10.0 Hz), 6.350 (d, 1H, J = 8.0 Hz), 5.941 (s, 1H), 5.616 (d, 1H, J = 10.0 Hz), 4.708 (s, 2H), 3.920 (t, 2H, J = 6.4 Hz), 2.272 (s, 3H), 1.819 (m, 2H), 1.449 (s, 6H), 1.046 (t, 3H, J = 7.6 Hz). 159.301, 153.744, 148.610, 147.462, 145.303, 132.136, 129.498, 129.456, 128.454, 126.507, 125.487, 124.322, 123.190, 116.452, 116.161, 114.236, 109.818, 109.464, 109.175, 76.176, 69.927, 67.570, 27.834, 22.387, 21.602, 10.442. |
| 43 | 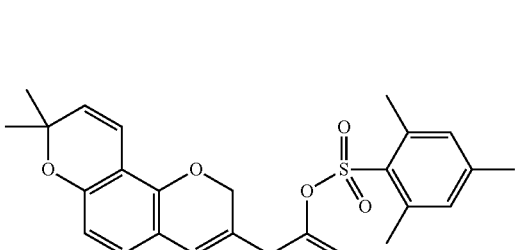(Compound 5-43) | 7.119 (d, 1H, J = 8.0 Hz), 6.787 (m, 1H), 6.785 (s, 2H), 6.63~6.68 (m, 2H), 6.587 (d, 1H, J = 10.0 Hz), 6.332 (d, 1H, J = 8.0 Hz), 6.180 (s, 1H), 5.602 (d, 1H, J = 10.0 Hz), 4.765 (s, 2H), 3.817 (t, 2H, J = 6.4 Hz), 2.447 (s, 6H), 2.180 (s, 3H), 1.758 (m, 2H), 1.442 (s, 6H), 1.006 (t, 3H, J = 7.2 Hz). 159.117, 153.685, 148.693, 147.612, 143.784, 140.248, 131.765, 131.454, 129.671, 129.324, 126.718, 125.536, 124.557, 123.119, 116.515, 115.959, 114.058, 109.507, 109.369, 109.032, 76.093, 69.855, 67.793, 27.823, 23.048, 22.325, 21.013, 10.367. |

TABLE 1-continued

| Number of Preparation Example | Chemical structure | $^1$H-NMR, $^{13}$C-NMR (CDCl$_3$, δ) |
|---|---|---|
| 44 | 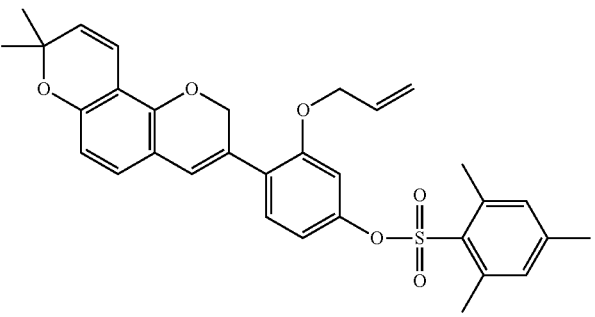(Compound 5-44) | 7.162 (d, 1H, J = 8.0 Hz), 6.989 (s, 2H), 6.818 (d, 1H, J = 8.0 Hz), 6.626 (d, 1H, J = 10.0 Hz), 6.528 (d, 1H, J = 2.0 Hz), 6.511 (s, 1H), 6.501 (dd, 1H, J = 8.0, 2.0 Hz), 6.371 (d, 1H, J = 8.0 Hz), 5.934 (m, 1H), 5.588 (d, 1H, J = 10.0 Hz), 5.327 (m, 1H, J = 17.2 Hz, 1.6 Hz), 5.253 (m, 1H, J = 14.8, 1.6 Hz), 4.969 (s, 2H), 4.381 (m, 2H, J = 5.2, 1.6 Hz), 2.580 (s, 6H), 2.329 (s, 3H), 1.420 (s, 6H).<br>156.543, 153.818, 149.550, 149.364, 143.871, 140.470, 132.189, 131.753, 130.643, 129.398, 129.020, 127.631, 127.065, 126.838, 123.321, 118.251, 116.521, 116.479, 114.280, 109.575, 109.422, 106.804, 76.165, 69.363, 68.043, 27.844, 22.755, 21.072. |
| 45 | 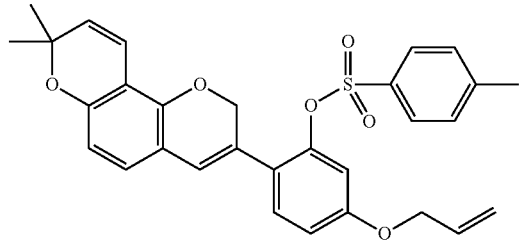(Compound 5-45) | 7.543 (d, 2H, J = 8.0 Hz), 7.052 (d, 1H, J = 8.0 Hz), 7.025 (d, 2H, J = 8.0 Hz), 6.963 (d, 1H, J = 2.4 Hz), 6.818 (dd, 1H, J = 8.0, 2.4 Hz), 6.630 (d, 1H, J = 8.0 Hz), 6.601 (d, 1H, J = 10.0 Hz), 6.353 (d, 1H, J = 8.0 Hz), 6.045 (m, 1H), 5.946 (s, 1H), 5.617 (d, 1H, J = 10.0 Hz), 5.434 (m, 1H, J = 17.2 Hz, 1.6 Hz), 5.376 (m, 1H, J = 14.8, 1.6 Hz), 4.713 (s, 2H), 4.544 (m, 2H, J = 5.2, 1.6 Hz), 2.276 (s, 3H), 1.449 (s, 6H).<br>158.672, 153.796, 148.639, 147.442, 145.329, 132.481, 132.124, 129.546, 129.474, 129.458, 128.454, 126.539, 125.393, 124.751, 123.351, 118.220, 116.441, 116.126, 114.418, 110.139, 109.475, 109.200, 76.191, 69.158, 67.551, 27.844, 21.609. |
| 46 | 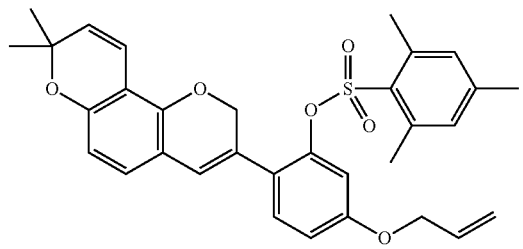(Compound 5-46) | 7.128 (d, 1H, J = 8.4 Hz), 6.812 (dd, 1H, J = 8.4, 2.4 Hz), 6.791 (s, 2H), 6.681 (d, 1H, J = 2.4 Hz), 6.662 (d, 1H, J = 8.4 Hz), 6.588 (d, 1H, J = 10.0 Hz), 6.333 (d, 1H, J = 8.4 Hz), 6.186 (s, 1H), 5.985 (m, 1H), 5.601 (s, 1H, J = 10.0 Hz), 5.368 (m, 1H, J = 17.2 Hz, 1.6 Hz), 5.287 (m, 1H, J = 14.8, 1.6 Hz), 4.771 (s, 2H), 4.448 (m, 1H, J = 2H, J = 5.2, 1.6 Hz), 2.444 (s, 6H), 2.185 (s, 3H), 1.442 (s, 6H).<br>158.518, 153.742, 148.727, 147.604, 143.833, 140.268, 132.498, 131.794, 131.426, 129.731, 129.348, 126.758, 125.455, 125.018, 123.273, 118.102, 116.513, 115.943, 114.200, 109.880, 109.392, 109.065, 76.122, 69.078, 67.777, 27.832, 23.048, 21.023. |

TABLE 1-continued

| Number of Preparation Example | Chemical structure | $^1$H-NMR, $^{13}$C-NMR (CDCl$_3$, δ) |
|---|---|---|
| 47 | 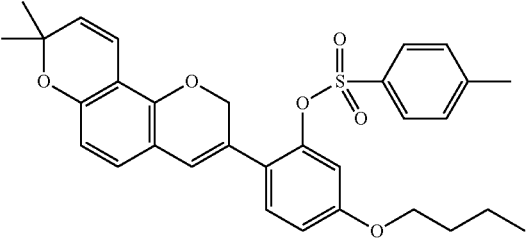 [SMILES: CCCCOc1ccc(C2=Cc3ccc4c(c3OC2)C=CC(C)(C)O4)c(OS(=O)(=O)c2ccc(C)cc2)c1]<br>(Compound 5-47) | 7.552 (d, 2H, J = 8.0 Hz), 7.042 (d, 1H, J = 8.0 Hz), 7.022 (d, 2H, J = 8.0 Hz), 6.931 (d, 1H, J = 2.4 Hz), 6.789 (dd, 1H, J = 8.0, 2.4 Hz), 6.625 (d, 1H, J = 8.0 Hz), 6.601 (d, 1H, J = 10.0 Hz), 6.349 (d, 1H, J = 8.0 Hz), 5.945 (s, 1H), 5.614 (d, 1H, J = 10.0 Hz), 4.709 (s, 2H), 3.959 (t, 2H, J = 6.4 Hz), 2.273 (s, 3H), 1.774 (m, 2H), 1.499 (m, 2H), 1.448 (s, 6H), 0.989 (t, 3H, J = 7.2 Hz).<br>159.334, 153.764, 148.632, 147.487, 145.299, 132.196, 129.504, 129.464, 128.470, 126.522, 125.508, 124.334, 123.219, 116.464, 116.170, 114.247, 109.824, 109.477, 109.185, 76.186, 68.179, 67.595, 31.094, 27.848, 21.603, 19.162, 13.817. |
| 48 | 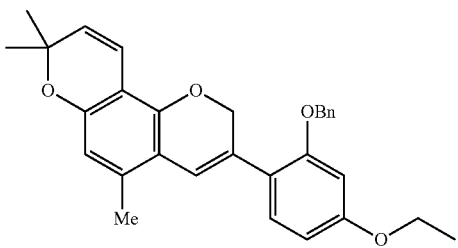 [SMILES: CCOc1ccc(C2=Cc3c(C)cc4c(c3OC2)C=CC(C)(C)O4)c(OCc2ccccc2)c1]<br>(Compound 5-48) | 7.29~7.45 (m, 5H), 7.251 (d, 1H, J = 8.4 Hz), 6.687 (d, 1H, J = 8.0 Hz), 6.598 (d, 1H, J = 10.0 Hz), 6.542 (d, 1H, J = 2.0 Hz), 6.509 (dd, 1H, J = 8.4, 2.0 Hz), 6.244 (s, 1H), 5.510 (d, 1H, J = 10.0 Hz), 5.035 (s, 2H), 4.926 (s, 2H), 4.025 (q, 2H, J = 6.8 Hz), 2.206 (s, 3H), 1.408 (t, 3H, J = 6.8 Hz), 1.402 (s, 6H).<br>159.787, 157.312, 152.757, 149.379, 136.481, 134.884, 129.198, 128.588, 128.214, 128.026, 128.003, 127.527, 121.428, 118.980, 116.758, 115.624, 110.796, 107.503, 105.609, 100.286, 76.000, 70.387, 68.069, 63.599, 27.859, 18.734, 14.787. |
| 49 | 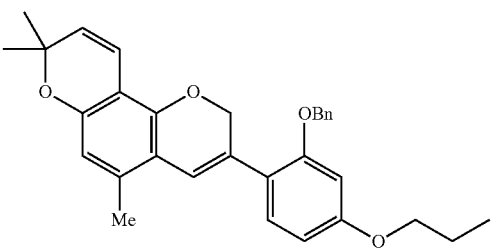 [SMILES: CCCOc1ccc(C2=Cc3c(C)cc4c(c3OC2)C=CC(C)(C)O4)c(OCc2ccccc2)c1]<br>(Compound 5-49) | 7.29~7.45 (m, 5H), 7.253 (d, 1H, J = 8.4 Hz), 6.685 (d, 1H, J = 8.0 Hz), 6.597 (d, 1H, J = 10.0 Hz), 6.540 (d, 1H, J = 2.0 Hz), 6.506 (dd, 1H, J = 8.4, 2.0 Hz), 6.245 (s, 1H), 5.511 (d, 1H, J = 10.0 Hz), 5.038 (s, 2H), 4.923 (s, 2H), 3.918 (t, 2H, J = 6.8 Hz), 2.207 (s, 3H), 1.804 (m, 2H, J = 6.8 Hz), 1.402 (s, 6H), 1.037 (t, 3H, J = 7.2 Hz).<br>160.015, 157.339, 152.768, 149.394, 136.516, 134.887, 129.196, 128.588, 128.212, 128.049, 128.005, 127.553, 121.404, 118.975, 116.775, 115.638, 110.803, 107.510, 105.733, 100.320, 76.005, 70.432, 68.093, 64.405, 27.873, 22.546, 18.726, 10.509. |

TABLE 1-continued
| Number of Preparation Example | Chemical structure | $^{1}$H-NMR, $^{13}$C-NMR (CDCl$_3$, δ) |
|---|---|---|
| 50 | 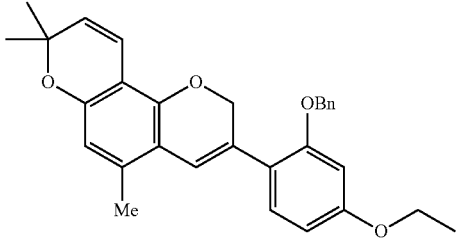 [SMILES: CCOc1ccc(C2=Cc3c(C)cc4c(c3OC2)C=CC(C)(C)O4)c(OCc2ccccc2)c1]<br>(Compound 5-50) | 7.29~7.48 (m, 5H), 7.269 (d, 1H, J = 8.4 Hz), 6.824 (s, 1H), 6.553 (d, 1H, J = 10.0 Hz), 6.513 (d, 1H, J = 2.0 Hz), 6.489 (dd, 1H, J = 8.4, 2.0 Hz), 6.011 (s, 1H), 5.431 (d, 1H, J = 10.0 Hz), 5.028 (s, 2H), 4.941 (s, 2H), 4.015 (q, 2H, J = 6.8 Hz), 3.776 (s, 3H), 1.415 (s, 6H), 1.401 (t, 3H, J = 6.8 Hz). 159.676, 157.284, 155.986, 154.098, 150.056, 136.637, 129.408, 128.549, 127.899, 127.423, 126.678, 126.154, 121.687, 116.663, 116.373, 106.515, 105.675, 103.168, 100.316, 92.899, 76.547, 70.380, 68.433, 63.576, 55.556, 27.880, 14.798. |
| 51 | 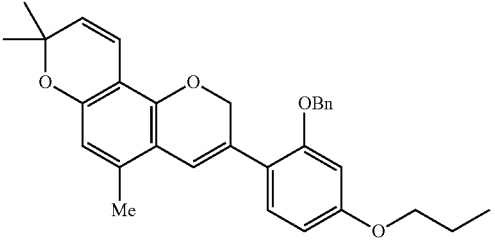 [SMILES: CCCOc1ccc(C2=Cc3c(C)cc4c(c3OC2)C=CC(C)(C)O4)c(OCc2ccccc2)c1]<br>(Compound 5-51) | 7.29~7.48 (m, 5H), 7.266 (d, 1H, J = 8.4 Hz), 6.825 (s, 1H), 6.553 (d, 1H, J = 10.0 Hz), 6.522 (d, 1H, J = 2.4 Hz), 6.496 (dd, 1H, J = 8.4, 2.4 Hz), 6.010 (s, 1H), 5.427 (d, 1H, J = 10.0 Hz), 5.025 (s, 2H), 4.940 (s, 2H), 3.900 (t, 2H, J = 6.8 Hz), 3.772 (s, 3H), 1.791 (m, 2H, J = 6.8 Hz), 1.413 (s, 6H), 1.046 (t, 3H, J = 6.8 Hz). 159.876, 157.271, 155.967, 154.077, 150.038, 136.626, 129.378, 128.527, 127.883, 127.430, 126.679, 126.134, 121.603, 116.654, 116.325, 106.506, 105.717, 103.151, 100.276, 92.880, 76.526, 70.367, 69.626, 68.428, 55.534, 27.863, 22.541, 10.502. |
| 52 | 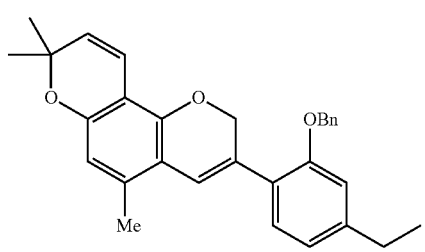 [SMILES: CCc1ccc(C2=Cc3c(C)cc4c(c3OC2)C=CC(C)(C)O4)c(OCc2ccccc2)c1]<br>(Compound 5-52) | 7.29~7.45 (m, 5H), 7.270 (d, 1H, J = 8.0 Hz), 6.838 (d, 1H, J = 8.0 Hz), 6.814 (s, 1H), 6.734 (s, 1H), 6.599 (d, 1H, J = 10.0 Hz), 6.247 (s, 1H), 5.509 (d, 1H, J = 10.0 Hz), 5.063 (s, 2H), 4.943 (s, 2H), 2.630 (q, 2H, J = 7.6 Hz), 2.207 (s, 3H), 1.402 (s, 6H), 1.244 (t, 3H, J = 7.6 Hz). 154.431, 153.000, 149.650, 145.470, 137.004, 135.040, 128.637, 128.579, 128.313, 128.239, 127.965, 127.583, 126.092, 120.617, 119.729, 116.775, 115.607, 111.892, 110.873, 107.544, 76.049, 70.396, 68.051, 28.925, 27.886, 18.744, 15.559. |

TABLE 1-continued

| Number of Preparation Example | Chemical structure | $^1$H-NMR, $^{13}$C-NMR (CDCl$_3$, δ) |
|---|---|---|
| 53 | 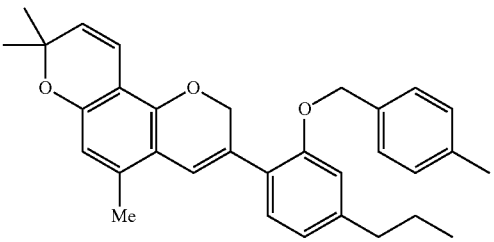<br>(Compound 5-53) | 7.294 (d, 2H, J = 8.0 Hz), 7.252 (d, 1H, J = 9.2 Hz), 7.169 (d, 2H, J = 8.0 Hz), 6.801 (d, 1H, J = 9.2 Hz), 6.794 (s, 1H), 6.599 (d, 1H, J = 10.0 Hz), 6.243 (s, 1H), 5.512 (d, 1H, J = 10.0 Hz), 5.011 (s, 2H), 4.928 (s, 2H), 2.584 (t, 2H, J = 7.6 Hz), 2.349 (s, 3H), 2.208 (s, 3H), 1.660 (m, 2H, J = 7.6 Hz), 1.403 (s, 6H), 0.954 (t, 3H, J = 7.6 Hz).<br>156.315, 152.861, 149.545, 143.872, 137.691, 135.012, 133.692, 129.223, 128.443, 128.414, 128.191, 127.707, 126.075, 121.169, 119.601, 116.785, 115.630, 112.406, 110.794, 107.510, 76.021, 70.292, 68.053, 38.082, 27.886, 24.504, 21.181, 18.726, 13.852. |
| 54 | 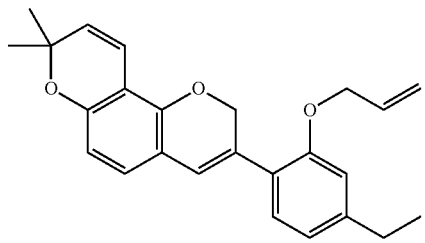 [SMILES: C=CCOc1cc(CC)ccc1C1=Cc2ccc3c(c2OC1)C=CC(C)(C)O3]<br>(Compound 5-54) | 7.231 (d, 1H, J = 8.0 Hz), 6.832 (d, 1H, J = 8.0 Hz), 6.811 (d, 1H, J = 8.0 Hz), 6.718 (s, 1H), 6.656 (d, 1H, J = 10.0 Hz), 6.542 (s, 1H), 6.375 (d, 1H, J = 8.0 Hz), 6.037 (m, 1H), 5.588 (d, 1H, J = 10.0 Hz), 5.395 (m, 1H, J = 17.6 Hz, 1.6 Hz), 5.266 (m, 1H, J = 9.2, 1.4 Hz), 5.050 (s, 2H), 4.552 (m, 2H), 2.639 (q, 2H, J = 7.6 Hz), 1.425 (s, 6H), 1.244 (t, 3H, J = 7.6 Hz).<br>156.148, 153.464, 149.310, 145.475, 133.165, 129.285, 129.091, 128.681, 126.627, 125.671, 122.101, 120.537, 117.621, 116.929, 116.669, 111.934, 109.581, 109.241, 76.060, 69.182, 68.441, 28.887, 27.822, 15.484. |
| 55 | 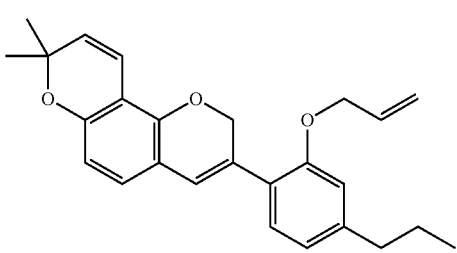 [SMILES: C=CCOc1cc(CCC)ccc1C1=Cc2ccc3c(c2OC1)C=CC(C)(C)O3]<br>(Compound 5-55) | 7.219 (d, 1H, J = 8.0 Hz), 6.830 (d, 1H, J = 8.0 Hz), 6.786 (d, 1H, J = 8.0, 1.2 Hz), 6.693 (d, 1H, J = 1.2 Hz), 6.655 (d, 1H, J = 10.0 Hz), 6.544 (s, 1H), 6.373 (d, 1H, J = 8.0 Hz), 6.038 (m, 1H), 5.588 (d, 1H, J = 10.0 Hz), 5.391 (m, 1H, J = 17.6 Hz, 1.6 Hz), 5.261 (m, 1H, J = 9.2, 1.4 Hz), 5.049 (s, 2H), 4.545 (m, 2H), 2.570 (t, 2H, J = 7.6 Hz), 1.645 (m, 2H), 1.424 (s, 6H), 0.955 (t, 3H, J = 7.6 Hz).<br>156.052, 153.450, 149.311, 143.924, 133.160, 129.277, 129.102, 128.548, 126.622, 125.646, 122.087, 121.192, 117.609, 116.940, 116.671, 112.491, 109.576, 109.233, 76.053, 69.170, 68.440, 38.062, 27.820, 24.473, 13.859. |

TABLE 1-continued

| Number of Preparation Example | Chemical structure | $^1$H-NMR, $^{13}$C-NMR (CDCl$_3$, δ) |
|---|---|---|
| 56 | 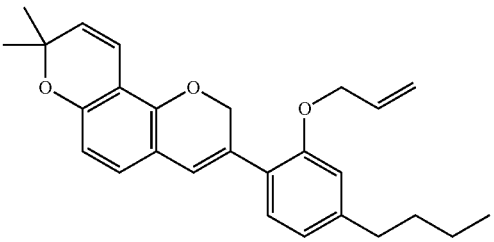 [SMILES: C=CCOc1cc(CCCC)ccc1C1=Cc2ccc3c(c2OC1)C=CC(C)(C)O3]<br>(Compound 5-56) | 7.212 (d, 1H, J = 8.0 Hz), 6.823 (d, 1H, J = 8.0 Hz), 6.782 (d, 1H, J = 8.0, 1.2 Hz), 6.691 (d, 1H, J = 1.2 Hz), 6.654 (d, 1H, J = 10.0 Hz), 6.540 (s, 1H), 6.371 (d, 1H, J = 8.0 Hz), 6.032 (m, 1H), 5.581 (d, 1H, J = 10.0 Hz), 5.387 (m, 1H, J = 17.6 Hz, 1.6 Hz), 5.255 (m, 1H, J = 9.2, 1.4 Hz), 5.047 (s, 2H), 4.533 (m, 2H), 2.588 (t, 2H, J = 7.6 Hz), 1.598 (m,2H), 1.419 (s, 6H), 1.372 (m, 2H), 0.932 (t, 3H, J = 7.6 Hz).<br>155.791, 153.435, 149.293, 144.111, 133.149, 129.238, 129.072, 128.529, 126.603, 125.586, 122.055, 121.128, 117.564, 116.922, 116.658, 112.450, 109.551, 109.213, 76.031, 69.156, 68.421, 35.653, 33.457, 27.799, 22.348, 13.836. |

Example 1: Preparation of 3-(2-hydroxy-4-methoxyphenyl)-8,8-dimethyl-2,3,4,8,9,10-hexahydropyrano[2,3-f]chromene (Compound I-1)

6.98 g (16.4 mmol) of 3-(2-benzyloxy-4-methoxyphenyl)-8,8-dimethyl-2,8-dihydropyrano[2,3-f]chromene (Compound 5-1) obtained in Preparation Example 1 was dissolved in 20 ml of THF, a high-pressure reactor was filled with the resulting solution, and 500 mg of 10% Pd/C (palladium on carbon) was added thereto. 5 atm of hydrogen was added thereto in a state where the temperature of the reactor was maintained at 50° C., and then the resulting mixture was vigorously stirred for 48 hours. Thereafter, hydrogen was removed from the high-pressure reactor, the reactor was replaced with a nitrogen atmosphere, and then the Pd/C catalyst was removed by filtering the reaction solution with a celite pad. The filtered solution was thoroughly concentrated by performing distillation under reduced pressure, and then recrystallized with IPA, thereby obtaining 5.27 g (15.5 mol) of a white powder 3-(2-hydroxy-4-methoxyphenyl)-8,8-dimethyl-2,3,4,8,9,10-hexahydropyrano[2,3-f]chromene (Yield: 94.5%).

$^1$H-NMR (CDCl3): 7.022 (d, 1H, J=8.8 Hz), 6.838 (d, 1H, J=8.4 Hz), 6.488 (dd, 1H, J=8.4, 2.4 Hz), 6.388 (d, 1H, J=8.8 Hz), 6.364 (d, 1H, J=2.4 Hz), 5.059 (s, 1H), 4.392 (m, 1H, J=10.4, 2.4, 0.8 Hz), 4.024 (t, 1H, J=10.4 Hz), 3.768 (s, 1H), 3.488 (m, 1H), 3.017 (dd, 1H, J=15.6, 10.4 Hz), 2.875 (ddd, 1H, J=15.6, 5.2, 2.4 Hz), 2.646 (m, 2H), 1.778 (t, 2H, J=5.8 Hz), 1.335 (s, 3H), 1.321 (s, 3H).

$^{13}$C-NMR (CDCl3): 159.257, 154.516, 152.772, 152.160, 128.184, 127.546, 120.182, 112.994, 109.394, 109.340, 105.957, 102.118, 73.917, 70.069, 55.340, 32.391, 31.811, 30.671, 26.833, 26.459, 17.187.

Example 2: Preparation of 3-(2-hydroxy-4-ethoxyphenyl)-8,8-dimethyl-2,3,4,8,9,10-hexahydropyrano[2,3-f]chromene (Compound I-2)

3-(2-benzyloxy-4-ethoxyphenyl)-8,8-dimethyl-2,8-dihydropyrano[2,3-f]chromene (Compound 5-2) obtained in Preparation Example 2 was used by the same method as in Example 1, thereby obtaining 3-(2-hydroxy-4-ethoxyphenyl)-8,8-dimethyl-2,3,4,8,9,10-hexahydropyrano[2,3-f]chromene.

$^1$H-NMR (CDCl3): 7.029 (d, 1H, J=8.0 Hz), 6.834 (d, 1H, J=8.0 Hz), 6.766 (dd, 1H, J=8.0, 1.2 Hz), 6.596 (d, 1H, J=1.2 Hz), 6.389 (d, 1H, J=8.0 Hz), 4.909 (s, 1H), 4.415 (m, 1H, J=10.4, 3.2, 2.0 Hz), 4.041 (t, 1H, J=10.4 Hz), 3.542 (m, 1H), 3.034 (dd, 1H, J=15.6, 10.4 Hz), 2.875 (ddd, 1H, J=15.6, 5.2, 2.0 Hz), 2.647 (m, 2H), 2.574 (q, 2H, J=7.6 Hz), 1.774 (t, 2H, J=6.8 Hz), 1.332 (s, 3H), 1.318 (s, 3H), 1.208 (t, 3H, J=7.6 Hz).

$^{13}$C-NMR (CDCl3): 153.373, 152.716, 152.102, 144.205, 127.472, 127.415, 124.773, 120.499, 114.963, 112.898, 109.310, 109.248, 73.795, 69.897, 32.308, 32.054, 30.532, 28.276, 26.784, 26.374, 17.120, 15.308.

3-phenyl-8,8-dimethyl-2,3,4,8,9,10-hexahydropyrano[2,3-f]chromene derivatives shown in the following Table 2 were synthesized by using 3-phenyl-2,8-dihydropyrano[2,3-f]chromene derivatives in Table 1 in accordance with the method in Example 1:

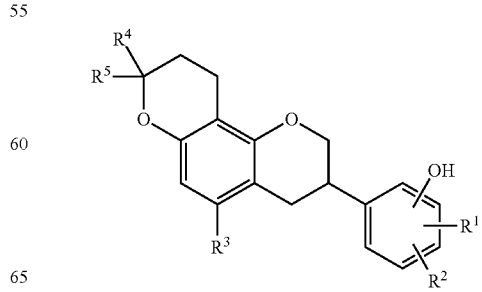

TABLE 2

| Number of Example (Number of Preparation Example corresponding to the reactant used) | Chemical structure | $^1$H-NMR (CDCl3, δ) |
|---|---|---|
| 1 (Preparation Example 1) | 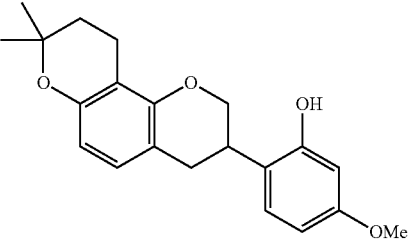 [SMILES: COc1ccc(C2COc3c(ccc4c3CCC(C)(C)O4)C2)c(O)c1]<br>(Compound I-1) | 7.022 (d, 1H, J = 8.8 Hz), 6.838 (d, 1H, J = 8.4 Hz), 6.488 (dd, 1H, J = 8.4, 2.4 Hz), 6.388 (d, 1H, J = 8.8 Hz), 6.364 (d, 1H, J = 2.4 Hz), 5.059 (s, 1H), 4.392 (m, 1H, J = 10.4, 2.4, 0.8 Hz), 4.024 (t, 1H, J = 10.4 Hz), 3.768 (s, 1H), 3.488 (m, 1H), 3.017 (dd, 1H, J = 15.6, 10.4 Hz), 2.875 (ddd, 1H, J = 15.6, 5.2, 2.4 Hz), 2.646 (m, 2H), 1.778 (t, 2H, J = 5.8 Hz), 1.335 (s, 3H), 1.321 (s, 3H). |
| 2 (Preparation Example 2) | 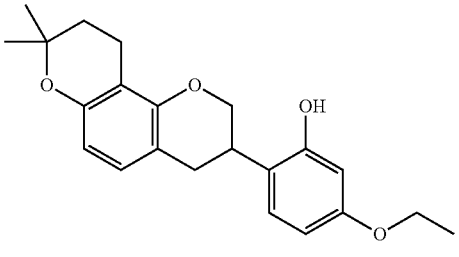 [SMILES: CCOc1ccc(C2COc3c(ccc4c3CCC(C)(C)O4)C2)c(O)c1]<br>(Compound I-2) | 6.989 (d, 1H, J = 8.4 Hz), 6.825 (d, 1H, J = 8.0 Hz), 6.458 (dd, 1H, J = 8.0, 2.4 Hz), 6.387 (d, 1H, J = 8.4 Hz), 6.324 (d, 1H, J = 2.4 Hz), 5.355 (s, 1H), 4.386 (m, 1H, J = 10.4, 3.2, 2.0 Hz), 4.007 (t, 1H, J = 10.4 Hz), 3.954 (q, 2H, J = 7.2 Hz), 3.484 (m, 1H), 3.006 (dd, 1H, J = 15.6, 11.2 Hz), 2.852 (m, 1H, J = 15.6, 4.8, 1.6 Hz), 2.641 (m, 2H), 1.770 (t, 2H, J = 6.8 Hz), 1.378 (t, 2H, J = 6.8 Hz), 1.331 (s, 3H), 1.316 (s, 3H). |
| 3 (Preparation Example 3) | 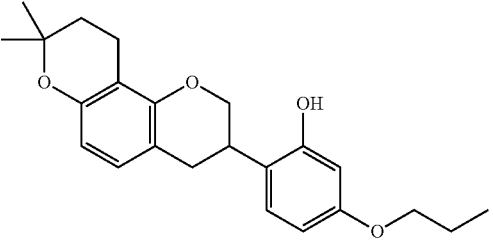 [SMILES: CCCOc1ccc(C2COc3c(ccc4c3CCC(C)(C)O4)C2)c(O)c1]<br>(Compound I-3) | 6.976 (d, 1H, J = 8.4 Hz), 6.817 (d, 1H, J = 8.4 Hz), 6.452 (dd, 1H, J = 8.4, 2.0 Hz), 6.391 (d, 1H, J = 8.4 Hz), 6.316 (d, 1H, J = 2.0 Hz), 5.600 (s, 1H), 4.385 (d, 1H, J = 10.0 Hz), 4.000 (t, 1H, J = 10.0 Hz), 3.812 (t, 2H, J = 6.4 Hz), 3.488 (m, 1H), 2.997 (dd, 1H, J = 15.6, 11.2 Hz), 2.837 (dd, 1H, J = 15.6, 4.4 Hz), 2.640 (m, 2H), 1.782 (t, 2H, J = 6.8 Hz), 1.765 (m, 2H), 1.329 (s, 3H), 1.314 (s, 3H), 0.994 (t, 3H, J = 7.2 Hz). |
| 4 (Preparation Example 5) | 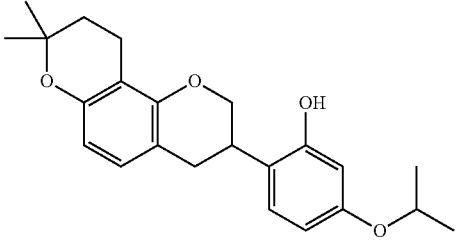 [SMILES: CC(C)Oc1ccc(C2COc3c(ccc4c3CCC(C)(C)O4)C2)c(O)c1]<br>(Compound I-4) | 7.000 (d, 1H, J = 8.4 Hz), 6.845 (d, 1H, J = 8.0 Hz), 6.472 (dd, 1H, J = 8.0, 2.4 Hz), 6.404 (d, 1H, J = 8.4 Hz), 6.344 (d, 1H, J = 2.4 Hz), 5.333 (s, 1H), 4.450 (m, 1H, J = 6.0 Hz), 4.409 (m, 1H, J = 10.4, 3.2, 2.0 Hz), 4.026 (t, 1H, J = 10.4 Hz), 3.498 (m, 1H), 3.026 (dd, 1H, J = 15.2, 11.2 Hz), 2.871 (m, 1H, J = 15.2, 4.8, 1.6 Hz), 2.669 (m, 2H), 1.789 (t, 2H, J = 6.8 Hz), 1.378 (t, 2H, J = 6.8 Hz), 1.349 (s, 3H), 1.331 (s, 3H), 1.324 (d, 6H, J = 6.0 Hz). |

TABLE 2-continued

| Number of Example (Number of Preparation Example corresponding to the reactant used) | Chemical structure | $^1$H-NMR (CDCl3, δ) |
|---|---|---|
| 5 (Preparation Example 6) | 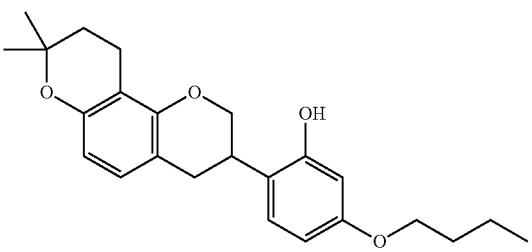 [SMILES: CCCCOc1ccc(C2COc3c(ccc4c3CCC(C)(C)O4)C2)c(O)c1]<br>(Compound I-5) | 6.995 (d, 1H, J = 8.0 Hz), 6.831 (d, 1H, J = 8.0 Hz), 6.469 (dd, 1H, J = 8.0, 2.4 Hz), 6.384 (d, 1H, J = 8.0 Hz), 6.342 (d, 1H, J = 2.4 Hz), 5.029 (s, 1H), 4.387 (m, 1H, J = 10.4 Hz), 4.011 (t, 1H, J = 10.4 Hz), 3.901 (t, 2H, J = 6.4 Hz), 3.478 (m, 1H), 3.012 (dd, 1H, J = 15.6, 11.2 Hz), 2.879 (m, 1H, J = 15.6, 4.4 Hz), 2.642 (m, 2H), 1.68~1.81 (m, 4H), 1.468 (m, 2H), 1.331 (s, 3H), 1.316 (s, 3H), 0.962 (t, 3H, J = 7.2 Hz). |
| 6 (Preparation Example 7) | 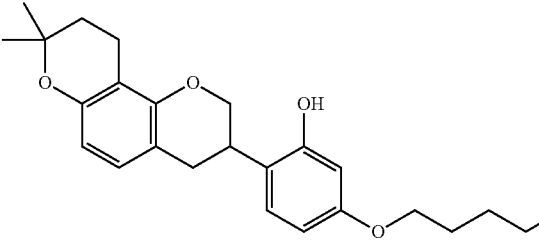<br>(Compound I-6) | 7.008 (d, 1H, J = 8.0 Hz), 6.846 (d, 1H, J = 8.0 Hz), 6.482 (dd, 1H, J = 8.0, 2.4 Hz), 6.408 (d, 1H, J = 8.0 Hz), 6.355 (d, 1H, J = 2.4 Hz), 5.313 (s, 1H), 4.406 (m, 1H, J = 10.4 Hz), 4.027 (t, 1H, J = 10.4 Hz), 3.906 (t, 2H, J = 6.4 Hz), 3.503 (m, 1H), 3.027 (dd, 1H, J = 15.6, 11.2 Hz), 2.874 (m, 1H, J = 15.6, 4.4 Hz), 2.662 (m, 2H), 1.71~1.81 (m, 4H), 1.40~1.87 (m, 4H), 1.353 (s, 3H), 1.338 (s, 3H), 0.941 (t, 3H, J = 7.2 Hz). |
| 7 (Preparation Example 9) | 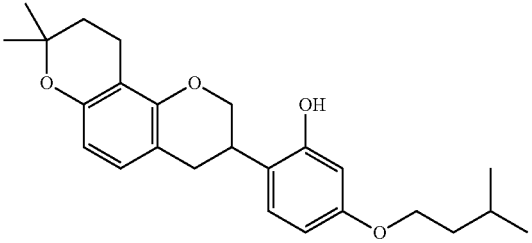 [SMILES: CC(C)CCOc1ccc(C2COc3c(ccc4c3CCC(C)(C)O4)C2)c(O)c1]<br>(Compound I-7) | 6.991 (d, 1H, J = 8.4 Hz), 6.827 (d, 1H, J = 8.4 Hz), 6.468 (dd, 1H, J = 8.4, 2.4 Hz), 6.385 (d, 1H, J = 8.4 Hz), 6.335 (d, 1H, J = 2.4 Hz), 5.083 (s, 1H), 4.387 (m, 1H, J = 10.4, 3.2, 2.0 Hz), 4.011 (t, 1H, J = 10.4 Hz), 3.918 (t, 2H, J = 6.4 Hz), 3.484 (m, 1H), 3.008 (dd, 1H, J = 15.6, 11.2 Hz), 2.857 (m, 1H, J = 15.6, 3.6, 1.6 Hz), 2.642 (m, 2H), 1.806 (m, 1H), 1.772 (t, 2H, J = 6.4 Hz), 1.643 (q, 2H, J = 6.4 Hz), 1.331 (s, 3H), 1.316 (s, 3H), 0.949 (d, 6H, J = 6.4 Hz). |
| 8 (Preparation Example 10) | 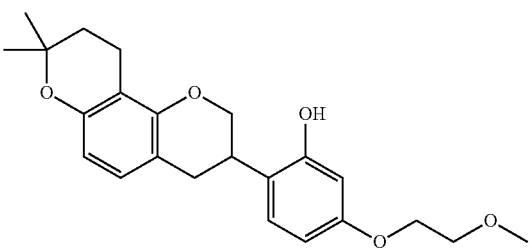<br>(Compound I-8) | 6.976 (d, 1H, J = 8.4 Hz), 6.833 (d, 1H, J = 8.4 Hz), 6.489 (d, 1H, J = 2.4 Hz), 6.433 (dd, 1H, J = 8.4, 2.4 Hz), 6.386 (d, 1H, J = 8.4 Hz), 6.170 (s, 1H), 4.388 (m, 1H, J = 10.4, 2.4 Hz), 4.083 (t, 2H, J = 4.4 Hz), 3.997 (t, 1H, J = 10.4 Hz), 3.784 (t, 2H, J = 4.4 Hz), 3.500 (m, 1H), 3.475 (s, 3H), 3.006 (dd, 1H, J = 15.6, 11.2 Hz), 2.853 (m, 1H, J = 15.6, 3.6 Hz), 2.650 (t, 2H), 1.777 (t, 2H, J = 6.8 Hz), 1.336 (s, 3H), 1.322 (s, 3H). |

TABLE 2-continued

| Number of Example (Number of Preparation Example corresponding to the reactant used) | Chemical structure | $^1$H-NMR (CDCl3, δ) |
|---|---|---|
| 9 (Preparation Example 11) | (Compound I-9) | 6.909 (d, 1H, J = 8.0 Hz), 6.829 (d, 1H, J = 8.4 Hz), 6.395 (dd, 1H, J = 8.4, 2.4 Hz), 6.287 (d, 1H, J = 2.4 Hz), 5.597 (b, 2H), 4.355 (m, 1H), 4.034 (t, 1H, J = 10.0 Hz), 3.478 (m, 1H), 2.983 (dd, 1H, J = 15.6, 10.4 Hz), 2.878 (ddd, 1H, J = 15.6, 4.8, 1.6 Hz), 2.634 (t, 2H, J = 6.8 Hz), 1.763 (t, 2H, J = 6.8 Hz), 1.323 (s, 3H), 1.314 (s, 3H). |
| 10 (Preparation Example 12) | (Compound I-10) | 6.939 (d, 1H, J = 8.4 Hz), 6.824 (d, 1H, J = 8.4 Hz), 6.421 (d, 1H, 2.4 Hz), 6.36~6.40 (m, 2H), 5.269 (s, 1H), 4.343 (m, 1H, J = 10.0, 2.0, 0.8 Hz), 3.968 (t, 1H, J = 10.0 Hz), 3.762 (s, 3H), 3.536 (m, 1H), 2.965 (dd, 1H, J = 15.2, 11.6 Hz), 2.821 (dd, 1H, J = 15.2, 3.2 Hz), 2.645 (t, 2H, J = 6.4 Hz), 1.774 (t, 2H, J = 6.4 Hz), 1.334 (s, 3H), 1.319 (s, 3H). |
| 11 (Preparation Example 13) | (Compound I-11) | 6.934 (d, 1H, J = 8.4 Hz), 6.829 (d, 1H, J = 8.4 Hz), 6.412 (d, 1H, 2.4 Hz), 6.35~6.40 (m, 2H), 5.143 (s, 1H), 4.341 (m, 1H, J = 10.0, 2.0, 0.8 Hz), 4.012 (t, 1H, J = 10.0 Hz), 3.989 (q, 2H, J = 6.4 Hz), 3.562 (m, 1H), 2.961 (dd, 1H, J = 15.2, 11.6 Hz), 2.851 (dd, 1H, J = 15.2, 3.2 Hz), 2.648 (t, 2H, J = 6.4 Hz), 1.776 (t, 2H, J = 6.4 Hz), 1.392 (t, 2H, J = 6.4 Hz), 1.334 (s, 3H), 1.323 (s, 3H). |
| 12 (Preparation Example 14) | (Compound I-12) | 6.937 (d, 1H, J = 8.4 Hz), 6.829 (d, 1H, J = 8.4 Hz), 6.409 (d, 1H, 2.4 Hz), 6.35~6.40 (m, 2H), 4.446 (m, 1H, J = 10.0, 2.0, 0.8 Hz), 3999 (t, 1H, J = 10.0 Hz), 3.889 (q, 2H, J = 6.4 Hz), 3.572 (m, 1H), 2.965 (dd, 1H, J = 15.2, 11.6 Hz), 2.846 (dd, 1H, J = 15.2, 3.2 Hz), 2.646 (t, 2H, J = 6.4 Hz), 1.75~1.87 (m, 4H), 1.332 (s, 3H), 1.324 (s, 3H), 1.023 (t, 3H, J = 6.4 Hz). |

TABLE 2-continued

| Number of Example (Number of Preparation Example corresponding to the reactant used) | Chemical structure | $^1$H-NMR (CDCl3, δ) |
|---|---|---|
| 13 (Preparation Example 18) | 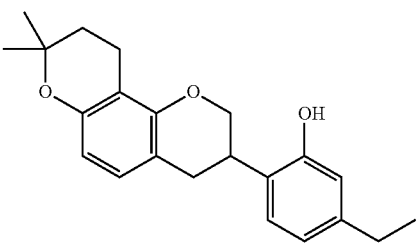 [SMILES: CCc1ccc(C2COc3c(ccc4c3CCC(C)(C)O4)C2)c(O)c1]<br>(Compound I-13) | 7.029 (d, 1H, J = 8.0 Hz), 6.834 (d, 1H, J = 8.0 Hz), 6.766 (dd, 1H, J = 8.0, 1.2 Hz), 6.596 (d, 1H, J = 1.2 Hz), 6.389 (d, 1H, J = 8.0 Hz), 4.909 (s, 1H), 4.415 (m, 1H, J = 10.4, 3.2, 2.0 Hz), 4.041 (t, 1H, J = 10.4 Hz), 3.542 (m, 1H), 3.034 (dd, 1H, J = 15.6, 10.4 Hz), 2.875 (ddd, 1H, J = 15.6, 5.2, 2.0 Hz), 2.647 (m, 2H), 2.574 (q, 2H, J = 7.6 Hz), 1.774 (t, 2H, J = 6.8 Hz), 1.332 (s, 3H), 1.318 (s, 3H), 1.208 (t, 3H, J = 7.6 Hz). |
| 14 (Preparation Example 21) | 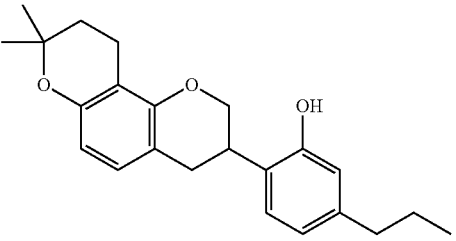 [SMILES: CCCc1ccc(C2COc3c(ccc4c3CCC(C)(C)O4)C2)c(O)c1]<br>(Compound I-14) | 7.029 (d, 1H, J = 8.0 Hz), 6.842 (d, 1H, J = 8.0 Hz), 6.755 (d, 1H, J = 8.0 Hz), 6.597 (s, 1H), 6.390 (d, 1H, J = 8.4 Hz), 4.804 (s, 1H), 4.423 (m, 1H, J = 10.4, 2.4 Hz), 4.046 (t, 1H, J = 10.4 Hz), 3.537 (m, 1H), 3.042 (dd, 1H, J = 15.6, 11.2 Hz), 2.886 (m, 1H), 2.652 (m, 2H), 2.518 (t, 2H, J = 7.6 Hz), 1.781 (t, 2H, J = 6.8 Hz), 1.612 (m, 2H, J = 7.2 Hz), 1.338 (s, 3H), 1.323 (s, 3H), 0.947 (t, 3H, J = 7.2 Hz). |
| 15 (Preparation Example 27) | 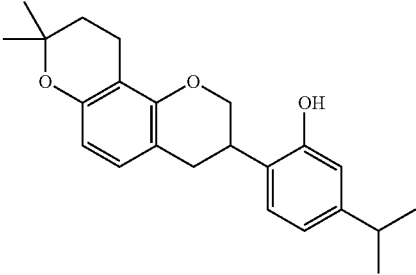 [SMILES: CC(C)c1ccc(C2COc3c(ccc4c3CCC(C)(C)O4)C2)c(O)c1]<br>(Compound I-15) | 7.058 (d, 1H, J = 8.0 Hz), 6.853 (d, 1H, J = 8.0 Hz), 6.812 (dd, 1H, J = 8.0, 1.2 Hz), 6.641 (d, 1H, J = 1.2 Hz), 6.408 (d, 1H, J = 8.0 Hz), 4.973 (s, 1H), 4.444 (m, 1H, J = 10.4, 3.2, 2.0 Hz), 4.060 (t, 1H, J = 10.4 Hz), 3.552 (m, 1H), 3.056 (dd, 1H, J = 15.6, 11.2 Hz), 2.892 (m, 1H, J = 15.6, 5.2, 1.6 Hz), 2.859 (m, 1H, J = 6.8 Hz), 2.668 (m, 2H), 1.794 (t, 2H, J = 6.8 Hz), 1.352 (s, 3H), 1.337 (s, 3H), 1.235 (d, 6H, J = 6.8 Hz). |
| 16 (Preparation Example 28) | 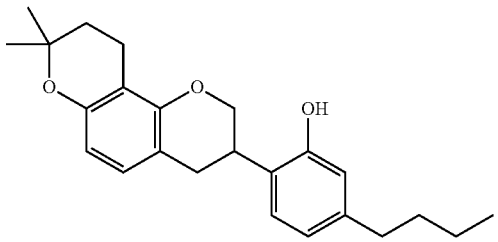 [SMILES: CCCCc1ccc(C2COc3c(ccc4c3CCC(C)(C)O4)C2)c(O)c1]<br>(Compound I-16) | 7.034 (d, 1H, J = 8.0 Hz), 6.851 (d, 1H, J = 8.0 Hz), 6.756 (dd, 1H, J = 8.0, 1.2 Hz), 6.595 (d, 1H, J = 1.2 Hz), 6.406 (d, 1H, J = 8.0 Hz), 4.904 (s, 1H), 4.426 (m, 1H, J = 10.4, 3.2, 2.0 Hz), 4.056 (t, 1H, J = 10.4 Hz), 3.549 (m, 1H), 3.050 (dd, 1H, J = 15.6, 11.2 Hz), 2.892 (m, 1H, J = 15.6, 5.2, 1.6 Hz), 2.667 (m, 2H), 2.546 (t, 2H, J = 4.4H), 1.792 (t, 2H, J = 6.8 Hz), 1.584 (m, 2H), 1.375 (m, 2H), 1.351 (s, 3H), 1.336 (s, 3H), 0.939 (t, 2H, J = 7.4 Hz). |

| Number of Example (Number of Preparation Example corresponding to the reactant used) | Chemical structure | $^1$H-NMR (CDCl3, δ) |
|---|---|---|
| 17 (Preparation Example 29) | (Compound I-17) | 7.033 (d, 1H, J = 8.0 Hz), 6.849 (d, 1H, J = 8.0 Hz), 6.756 (dd, 1H, J = 8.0, 1.2 Hz), 6.598 (d, 1H, J = 1.2 Hz), 6.403 (d, 1H, J = 8.0 Hz), 4.898 (s, 1H), 4.437 (m, 1H, J = 10.4, 3.2, 2.0 Hz), 4.054 (t, 1H, J = 10.4 Hz), 3.548 (m, 1H), 3.048 (dd, 1H, J = 15.6, 11.2 Hz), 2.895 (m, 1H, J = 15.6, 5.2, 1.6 Hz), 2.667 (m, 2H), 2.536 (t, 2H, J = 4.4H), 1.790 (t, 2H, J = 6.8 Hz), 1.599 (m, 2H), 1.36 (m, 4H), 1.348 (s, 3H), 1.333 (s, 3H), 0.908 (t, 2H, J = 7.4 Hz). |
| 18 (Preparation Example 31) | (Compound I-18) | 6.901 (d, 1H, J = 8.0 Hz), 6.857 (d, 1H, J = 8.4 Hz), 6.790 (d, 1H, J = 8.0 Hz), 6.411 (d, 1H, J = 8.4 Hz), 4.834 (s, 1H), 4.430 (m, 1H, J = 10.0, 3.2, 2.0 Hz), 4.051 (t, 1H, J = 10.0 Hz), 3.543 (m, 1H), 3.036 (dd, 1H, J = 15.6, 11.2 Hz), 2.896 (m, 1H, J = 15.6, 5.2, 2.0 Hz), 2.672 (m, 2H), 2.297 (s, 3H), 2.199 (s, 3H), 1.798 (t, 2H, J = 6.8 Hz), 1.357 (s, 3H), 1.344 (s, 3H). |
| 19 (Preparation Example 32) | (Compound I-19) | 6.886 (s, 1H), 6.857 (d, 1H, J = 4.8 Hz), 6.579 (s, 1H), 6.418 (d, 1H, J = 4.8 Hz), 4.965 (s, 1H), 4.433 (dd, 1H, J = 6.0 Hz), 4.053 (t, 1H, J = 6.0 Hz), 3.534 (m, 1H), 3.067 (dd, 1H, J = 8.8, 6.8 Hz), 2.873 (ddd, 1H, J = 8.8, 2.4, 0.8 Hz), 2.680 (m, 2H), 2.203 (s, 6H), 1.803 (t, 2H, J = 4.0 Hz), 1.364 (s, 3H), 1.348 (s, 3H). |
| 20 (Preparation Example 35) | (Compound I-20) | 6.839 (d, 1H, J = 8.0 Hz), 6.819 (d, 1H, J = 8.0 Hz), 6.395 (d, 1H, J = 8.0 Hz), 6.385 (d, 1H, J = 8.0 Hz), 4.927 (s, 1H), 4.891 (s, 1H), 4.388 (m, 1H, J = 10.4, 3.2, 2.0 Hz), 4.011 (t, 1H, J = 10.4 Hz), 3.469 (m, 1H), 2.997 (dd, 1H, J = 15.6, 11.2 Hz), 2.869 (ddd, 1H, J = 15.6, 5.2, 1.6 Hz), 2.653 (m, 2H), 2.167 (s, 3H), 1.783 (t, 2H, J = 6.8 Hz), 1.341 (s, 3H), 1.328 (s, 3H). |

TABLE 2-continued

| Number of Example (Number of Preparation Example corresponding to the reactant used) | Chemical structure | $^1$H-NMR (CDCl3, δ) |
|---|---|---|
| 21 (Preparation Example 36) | (Compound I-21) | 7.044 (dd, 1H, J = 8.4, 6.4 Hz), 6.834 (dd, 1H, J = 8.4, 2.0 Hz), 6.620 (dt, 1H, J = 8.4, 2.4 Hz), 6.501 (dd, 1H, J = 9.6, 2.4 Hz), 6.396 (d, 1H, J = 8.4 Hz), 5.400 (s, 1H), 4.379 (m, 1H, J = 10.0, 3.6, 2.0 Hz), 4.039 (t, 1H, J = 10.0 Hz), 3.523 (m, 1H), 2.997 (dd, 1H, J = 15.6, 10.4 Hz), 2.892 (ddd, 1H, J = 15.6, 5.2, 2.0 Hz), 2.642 (m, 2H), 1.777 (t, 2H, J = 6.8 Hz), 1.335 (s, 3H), 1.321 (s, 3H). |
| 22 (Preparation Example 37) | (Compound I-22) | 7.025 (d, 1H, J = 8.4 Hz), 6.888 (dd, 1H, J = 8.4, 2.0 Hz), 6.832 (d, 1H, J = 8.4 Hz), 6.759 (d, 1H, J = 2.0 Hz), 6.397 (d, 1H, J = 8.4 Hz), 5.256 (s, 1H), 4.375 (m, 1H, J = 10.0, 3.6, 2.0 Hz), 4.047 (t, 1H, J = 10.0 Hz), 3.532 (m, 1H), 2.989 (dd, 1H, J = 15.6, 10.4 Hz), 2.896 (ddd, 1H, J = 15.6, 5.2, 1.6 Hz), 2.637 (m, 2H), 1.775 (t, 2H, J = 6.8 Hz), 1.333 (s, 3H), 1.320 (s, 3H). |
| 23 (Preparation Example 48) | (Compound I-23) | 7.010 (d, 1H, J = 8.4 Hz), 6.475 (dd, 1H, J = 8.4, 2.4 Hz), 6.341 (d, 1H, J = 2.4 Hz), 6.311 (s, 1H), 5.189 (s, 1H), 4.352 (m, 1H, J = 10.4, 3.2, 2.0 Hz), 4.007 (t, 1H, J = 10.4 Hz), 3.966 (q, 2H, J = 7.2 Hz), 3.484 (m, 1H), 3.006 (dd, 1H, J = 15.6, 11.2 Hz), 2.816 (m, 1H), 2.756 (m, 1H), 2.621 (m, 2H), 2.138 (s, 3H), 1.742 (t, 2H, J = 6.8 Hz), 1.385 (t, 2H, J = 6.8 Hz), 1.325 (s, 3H), 1.309 (s, 3H). |
| 24 (Preparation Example 49) | (Compound I-24) | 7.008 (d, 1H, J = 8.4 Hz), 6.476 (dd, 1H, J = 8.4, 2.4 Hz), 6.347 (d, 1H, J = 2.4 Hz), 6.312 (s, 1H), 5.263 (s, 1H), 4.352 (m, 1H, J = 10.4, 3.2, 2.0 Hz), 4.006 (t, 1H, J = 10.4 Hz), 3.850 (t, 2H, J = 7.2 Hz), 3.593 (m, 1H), 2.826 (dd, 1H, J = 15.6, 11.2 Hz), 2.756 (dd, 1H, J = 15.6, 10.0 Hz)), 2.621 (m, 2H), 2.137 (s, 3H), 1.731.82 (m, 4H), 1.325 (s, 3H), 1.309 (s, 3H), 1.011 (t, 2H, J = 6.8 Hz). |

TABLE 2-continued

| Number of Example (Number of Preparation Example corresponding to the reactant used) | Chemical structure | $^1$H-NMR (CDCl3, δ) |
|---|---|---|
| 25 (Preparation Example 50) | (Compound I-25) | 7.007 (d, 1H, J = 8.4 Hz), 6.441 (dd, 1H, J = 8.4, 2.4 Hz), 6.310 (d, 1H, J = 2.4 Hz), 6.009 (s, 1H), 5.439 (s, 1H), 4.358 (m, 1H, J = 10.4, 3.2, 2.0 Hz), 3.978 (t, 1H, J = 10.4 Hz), 3.933 (q, 2H, J = 7.2 Hz), 3.735 (s, 3H), 3.424 (m, 1H), 2.922 (dd, 1H, J = 15.6, 11.2 Hz), 2.722 (dd, 1H, J = 15.6, 10.8), 2.582 (m, 2H), 2.621 (m, 2H), 1.756 (t, 2H, J = 6.8 Hz), 1.367 (t, 2H, J = 6.8 Hz), 1.334 (s, 3H), 1.321 (s, 3H). |
| 26 (Preparation Example 51) | (Compound I-26) | 7.022 (d, 1H, J = 8.4 Hz), 6.462 (dd, 1H, J = 8.4, 2.4 Hz), 6.344 (d, 1H, J = 2.4 Hz), 6.004 (s, 1H), 5.024 (s, 1H), 4.360 (m, 1H, J = 10.4, 3.2, 2.0 Hz), 3.978 (t, 1H, J = 10.4 Hz), 3.858 (t, 2H, J = 6.8 Hz), 3.744 (s, 3H), 3.412 (m, 1H), 2.929 (dd, 1H, J = 15.6, 11.2 Hz), 2.721 (dd, 1H, J = 15.6, 10.8), 2.583 (m, 2H), 1.73~1.80 (m, 4H), 1.336 (s, 3H), 1.323 (s, 3H). 1.014 (t, 2H, J = 7.2 Hz). |

Synthesis Example 1: Preparation of (R)-3-(2-hydroxy-4-ethoxyphenyl)-8,8-dimethyl-2,3,4,8,9,10-hexahydropyrano[2,3-f]chromene (Compound I-2a) and (S)-3-(2-hydroxy-4-ethoxyphenyl)-8,8-dimethyl-2,3,4,8,9,10-hexahydropyrano[2,3-f]chromene (Compound I-2b)

1-1: Preparation of (R)-3-(2-benzyloxy-4-ethoxyphenyl)-8,8-dimethyl-2,3,4,8,9,10-hexahydropyrano[2,3-f]chromene (Compound 6-2a) and (S)-3-(2-benzyloxy-4-ethoxyphenyl)-8,8-dimethyl-2,3,4,8,9,10-hexahydropyrano[2,3-f]chromene (Compound 6-2b)

20.0 g (43.8 mmol) of 3-(2-benzyloxy-4-ethoxyphenyl)-8,8-dimethyl-2,8-dihydropyrano[2,3-f]chromene (Compound 5-2) obtained in Preparation Example 2 was dissolved in 50 ml of methylene chloride (CH$_2$Cl$_2$), and 400 mg of UbaPHOX [((4S,5S)-Cy2-UbaPHOX)Ir(COD)]BARF was added thereto. Next, 7 atm of hydrogen was added thereto, and then the resulting mixture was stirred for 12 hours in a state where the temperature of the reactor was maintained at 35° C. The reaction was terminated, and then the solvent was concentrated, thereby obtaining 19.68 g (yield 98%) of (R)-3-(2-benzyloxy-4-ethoxyphenyl)-8,8-dimethyl-2,3,4,8,9,10-hexahydropyrano[2,3-f]chromene (Compound 6-2a).

UbaPHOX [((4R,5R)-Cy2-UbaPHOX)Ir(COD)]BARF was used by the same method, thereby obtaining (S)-3-(2-benzyloxy-4-ethoxyphenyl)-8,8-dimethyl-2,3,4,8,9,10-hexahydropyrano[2,3-f]chromene (Compound 6-2b). $^1$H-NMR results for the obtained Compound are as follows.

$^1$H-NMR (CDCl3): 7.30~7.45 (m, 5H), 7.026 (d, 1H, J=8.4 Hz), 6.824 (d, 1H, J=8.4 Hz), 6.545 (d, 1H, J=2.0 Hz), 6.466 (dd, 1H, J=8.4, 2.0 Hz), 6.373 (d, 1H, J=8.4 Hz), 5.075 (s, 2H), 4.371 (m, 1H, J=10.4, 3.6, 2.0 Hz), 4.002 (t, 1H, J=10.4 Hz), 3.991 (q, 2H, J=7.0 Hz), 3.652 (m, 1H), 2.983 (dd, 1H, J=15.6, 10.8 Hz), 2.866 (m, 1H, J=15.6, 5.2, 1.6 Hz), 2.628 (t, 2H, J=6.8 Hz), 1.762 (t, 2H, J=6.8 Hz), 1.388 (t, 2H, J=7.0 Hz), 1.322 (s, 3H), 1.313 (s, 3H).

1-2: Preparation of (R)-3-(2-hydroxy-4-ethoxyphenyl)-8,8-dimethyl-2,3,4,8,9,10-hexahydropyrano[2,3-f]chromene (Compound I-2a) and (S)-3-(2-hydroxy-4-ethoxyphenyl)-8,8-dimethyl-2,3,4,8,9,10-hexahydropyrano[2,3-f]chromene (Compound I-2b)

After 19.68 g (42.9 mmol) of (R)-3-(2-benzyloxy-4-ethoxyphenyl)-8,8-dimethyl-2,3,4,8,9,10-hexahydropyrano[2,3-f]chromene (Compound 6-2a) obtained in Synthesis Example 1-1 was dissolved in 50 ml of THF, a high-pressure reactor was filled with the resulting solution, and 400 mg of 10% Pd/C was added thereto. 5 atm of hydrogen was added thereto in a state where the temperature of the reactor was maintained at 50° C., and then the resulting mixture was vigorously stirred for 15 hours. Thereafter, hydrogen was removed from the high-pressure reactor, the reactor was replaced with a nitrogen atmosphere, and then the Pd/C catalyst was removed by filtering the reaction solution with a celite pad. The filtered solution was thoroughly concentrated by performing distillation under reduced pressure, and then recrystallized with IPA, thereby obtaining 14.96 g (40.6 mmol) of a white powder (R)-3-(2-hydroxy-4-ethoxyphenyl)-8,8-dimethyl-2,3,4,8,9,10-hexahydropyrano[2,3-f]chromene (Compound I-2a) (Yield: 94.5%).

(S)-3-(2-hydroxy-4-ethoxyphenyl)-8,8-dimethyl-2,3,4,8,9,10-hexahydropyrano[2,3-f]chromene (Compound I-2b) was obtained from (S)-3-(2-benzyloxy-4-ethoxyphenyl)-8,8-dimethyl-2,3,4,8,9,10-hexahydropyrano[2,3-f]chromene (Compound 6-2b) by using the same method. $^1$H-NMR, $^{13}$C-NMR, optical rotation, and M.P. results for the obtained Compound are as follows.

$^1$H-NMR (CDCl3): 6.989 (d, 1H, J=8.4 Hz), 6.825 (d, 1H, J=8.0 Hz), 6.458 (dd, 1H, J=8.0, 2.4 Hz), 6.387 (d, 1H, J=8.4 Hz), 6.324 (d, 1H, J=2.4 Hz), 5.355 (s, 1H), 4.386 (m, 1H, J=10.4, 3.2, 2.0 Hz), 4.007 (t, 1H, J=10.4 Hz), 3.954 (q, 2H, J=7.2 Hz), 3.484 (m, 1H), 3.006 (dd, 1H, J=15.6, 11.2 Hz), 2.852 (m, 1H, J=15.6, 4.8, 1.6 Hz), 2.641 (m, 2H), 1.770 (t, 2H, J=6.8 Hz), 1.378 (t, 2H, J=6.8 Hz), 1.331 (s, 3H), 1.316 (s, 3H).

$^{13}$C-NMR (CDCl3): 158.552, 154.340, 152.719, 152.091, 128.075, 127.465, 119.882, 112.909, 109.305, 109.248, 106.572, 102.504, 73.798, 70.018, 63.450, 32.311, 31.749, 30.614, 26.776, 26.390, 17.116, 14.781.

Optical Rotation Data
R-enantiomer—$[\alpha]_D^{20}$: −6.2° (c=0.025, ethanol); and
S-enantiomer—$[\alpha]_D^{20}$: +6.0° (c=0.025, ethanol).
M. P.
R-enantiomer: 132.5° C.; and
S-enantiomer: 132.0° C.

Synthesis Example 2: Preparation of (R)-3-(2-hydroxy-4-propoxyphenyl)-8,8-dimethyl-2,3,4,8,9,10-hexahydropyrano[2,3-f]chromene (Compound I-3a) and (S)-3-(2-hydroxy-4-propoxyphenyl)-8,8-dimethyl-2,3,4,8,9,10-hexahydropyrano[2,3-f]chromene (Compound I-3b)

19.68 g (yield 98%) of (R)-3-(2-benzyloxy-4-propoxyphenyl)-8,8-dimethyl-2,3,4,8,9,10-hexahydropyrano[2,3-f]chromene (Compound 6-3a) was obtained from 20.0 g of 3-(2-benzyloxy-4-poropoxyphenyl)-8,8-dimethyl-2,8-dihydropyrano[2,3-f]chromene (Compound 5-3) obtained in Preparation Example 3 by using the same method as in Synthesis Example 1. Further, (S)-3-(2-benzyloxy-4-propoxyphenyl)-8,8-dimethyl-2,3,4,8,9,10-hexahydropyrano[2,3-f]chromene (Compound 6-3b) was obtained by using the same method as in Synthesis Example 1-1, and $^1$H-NMR and $^{13}$C-NMR results for the obtained Compound are as follows.

$^1$H-NMR (CDCl3): 7.30~7.45 (m, 5H), 7.031 (d, 1H, J=8.4 Hz), 6.828 (d, 1H, J=8.4 Hz), 6.558 (d, 1H, J=2.4 Hz), 6.476 (dd, 1H, J=8.4, 2.4 Hz), 6.373 (d, 1H, J=8.4 Hz), 5.082 (s, 2H), 4.371 (m, 1H, J=10.4, 3.6, 2.0 Hz), 4.002 (t, 1H, J=10.4 Hz), 3.886 (q, 2H, J=7.0 Hz), 3.647 (m, 1H), 2.949 (dd, 1H, J=15.6, 10.8 Hz), 2.868 (m, 1H, J=15.6, 5.2, 1.6 Hz), 2.628 (t, 2H, J=6.8 Hz), 1.796 (t, 2H, J=6.8 Hz), 1.764 (m, 2H), 1.325 (s, 3H), 1.316 (s, 3H), 1.024 (t, 2H, J=7.6 Hz).

$^{13}$C-NMR (CDCl3): 158.989, 157.253, 152.783, 152.207, 136.917, 128.581, 127.827, 127.600, 127.430, 127.132, 122.230, 112.913, 109.236, 109.120, 105.244, 100.336, 73.614, 70.224, 70.004, 69.541, 32.315, 31.317, 30.807, 26.790, 26.482, 22.553, 17.127, 10.536.

In addition, (R)- and (S)-3-(2-hydroxy-4-propoxyphenyl)-8,8-dimethyl-2,3,4,8,9,10-hexahydropyrano[2,3-f]chromenes were obtained from (R)- and (S)-3-(2-benzyloxy-4-propoxyphenyl)-8,8-dimethyl-2,3,4,8,9,10-hexahydropyrano[2,3-f]chromenes (Compounds 6-3a and 6-3b), respectively, by using the same method as in Synthesis Example 1-2. $^1$H-NMR, $^{13}$C-NMR, optical rotation, and M.P. results for the obtained Compounds are as follows.

$^1$H-NMR (CDCl3): 6.976 (d, 1H, J=8.4 Hz), 6.817 (d, 1H, J=8.4 Hz), 6.452 (dd, 1H, J=8.4, 2.0 Hz), 6.391 (d, 1H, J=8.4 Hz), 6.316 (d, 1H, J=2.0 Hz), 5.600 (s, 1H), 4.385 (d, 1H, J=10.0 Hz), 4.000 (t, 1H, J=10.0 Hz), 3.812 (t, 2H, J=6.4 Hz), 3.488 (m, 1H), 2.997 (dd, 1H, J=15.6, 11.2 Hz), 2.837 (dd, 1H, J=15.6, 4.4 Hz), 2.640 (m, 2H), 1.782 (t, 2H, J=6.8 Hz), 1.765 (m, 2H), 1.329 (s, 3H), 1.314 (s, 3H), 0.994 (t, 3H, J=7.2 Hz).

$^{13}$C-NMR (CDCl3): 158.678, 154.412, 152.596, 152.054, 128.015, 127.483, 119.827, 113.016, 109.299, 109.226, 106.588, 102.460, 73.888, 70.014, 69.537, 32.287, 31.702, 30.552, 26.728, 26.349, 22.453, 17.096, 10.458.

Optical Rotation Data
R-enantiomer—$[\alpha]_D^{20}$: −5.3° (c=0.025, ethanol); and
S-enantiomer—$[\alpha]_D^{20}$: +5.8° (c=0.025, ethanol).
M. P.
R-enantiomer: 153.6° C.; and
S-enantiomer: 153.4° C.

Synthesis Example 3: Preparation of (R)-3-(2-hydroxy-4-butoxyphenyl)-8,8-dimethyl-2,3,4,8,9,10-hexahydropyrano[2,3-f]chromene (Compound I-5a) and (S)-3-(2-hydroxy-4-butoxyphenyl)-8,8-dimethyl-2,3,4,8,9,10-hexahydropyrano[2,3-f]chromene (Compound I-5b)

(R)- and (S)-3-(2-hydroxy-4-butoxyphenyl)-8,8-dimethyl-2,3,4,8,9,10-hexahydropyrano[2,3-f]chromenes with >96% ee were synthesized by using 3-(2-benzyloxy-4-butoxyphenyl)-8,8-dimethyl-2,8-dihydropyrano[2,3-f]chromene (Compound 5-6) synthesized in Preparation Example 6 and the method in Synthesis Example 1, respectively, and $^1$H-NMR, $^{13}$C-NMR, optical rotation, and M.P. results for the obtained Compounds are as follows.

$^1$H-NMR (CDCl3): 6.995 (d, 1H, J=8.0 Hz), 6.831 (d, 1H, J=8.0 Hz), 6.469 (dd, 1H, J=8.0, 2.4 Hz), 6.384 (d, 1H, J=8.0 Hz), 6.342 (d, 1H, J=2.4 Hz), 5.029 (s, 1H), 4.387 (m, 1H, J=10.4 Hz), 4.011 (t, 1H, J=10.4 Hz), 3.901 (t, 2H, J=6.4 Hz), 3.478 (m, 1H), 3.012 (dd, 1H, J=15.6, 11.2 Hz), 2.879 (m, 1H, J=15.6, 4.4 Hz), 2.642 (m, 2H), 1.68-1.81 (m, 4H), 1.468 (m, 2H), 1.331 (s, 3H), 1.316 (s, 3H), 0.962 (t, 3H, J=7.2 Hz).

$^{13}$C-NMR (CDCl3): 158.793, 154.331, 152.721, 152.092, 128.047, 127.461, 119.777, 112.909, 109.299, 109.248, 106.628, 102.511, 73.786, 70.023, 67.738, 32.317, 31.756, 31.227, 30.626, 26.777, 26.390, 19.193, 17.117, 13.807.

Optical Rotation Data
R-enantiomer—$[\alpha]_D^{20}$: −5.3° (c=0.025, ethanol); and
S-enantiomer—$[\alpha]_D^{20}$: +5.1° (c=0.025, ethanol).
M. P.
R-enantiomer: 115.9° C.; and
S-enantiomer: 114.6° C.

Synthesis Example 4: Preparation of (R)-3-(2-hydroxy-4-isopentyloxyphenyl)-8,8-dimethyl-2,3,4,8,9,10-hexahydropyrano[2,3-f]chromene (Compound I-7a) and (S)-3-(2-hydroxy-4-isopentyloxyphenyl)-8,8-dimethyl-2,3,4,8,9,10-hexahydropyrano[2,3-f]chromene (Compound I-7b)

(R)- and (S)-3-(2-hydroxy-4-isopentyloxyphenyl)-8,8-dimethyl-2,3,4,8,9,10-hexahydropyrano[2,3-f]chromenes with >96% ee were synthesized by using 3-(2-benzyloxy-4-isopentyloxyphenyl)-8,8-dimethyl-2,8-dihydropyrano[2,3-f]chromene (Compound 5-9) synthesized in Preparation Example 9 and the method in Synthesis Example 1, respectively, and ¹H-NMR, ¹³C-NMR, optical rotation, and M.P. results for the obtained Compounds are as follows.

¹H-NMR (CDCl3): 6.991 (d, 1H, J=8.4 Hz), 6.827 (d, 1H, J=8.4 Hz), 6.468 (dd, 1H, J=8.4, 2.4 Hz), 6.385 (d, 1H, J=8.4 Hz), 6.335 (d, 1H, J=2.4 Hz), 5.083 (s, 1H), 4.387 (m, 1H, J=10.4, 3.2, 2.0 Hz), 4.011 (t, 1H, J=10.4 Hz), 3.918 (t, 2H, J=6.4 Hz), 3.484 (m, 1H), 3.008 (dd, 1H, J=15.6, 11.2 Hz), 2.857 (m, 1H, J=15.6, 3.6, 1.6 Hz), 2.642 (m, 2H), 1.806 (m, 1H), 1.772 (t, 2H, J=6.4 Hz), 1.643 (q, 2H, J=6.4 Hz), 1.331 (s, 3H), 1.316 (s, 3H), 0.949 (d, 6H, J=6.4 Hz).

¹³C-NMR (CDCl3): 158.881, 154.197, 152.861, 152.137, 128.120, 127.459, 119.736, 112.789, 109.288, 109.284, 106.724, 102.561, 73.700, 70.031, 66.431, 37.940, 32.345, 31.805, 30.710, 26.836, 26.434, 25.031, 22.573, 17.150.

Optical Rotation Data

R-enantiomer—[α]$_D^{20}$: −1.7° (c=0.001, methylene chloride); and

S-enantiomer—[α]$_D^{20}$: +1.5° (c=0.001, methylene chloride).

M. P.

R-enantiomer: 164.7° C.; and

S-enantiomer: 164.1° C.

Synthesis Example 5: Preparation of (R)-3-(2,4-dihyroxyphenyl)-8,8-dimethyl-2,3,4,8,9,10-hexahydropyrano[2,3-f]chromene (Compound I-9a) and (S)-3-(2,4-dihyroxyphenyl)-8,8-dimethyl-2,3,4,8,9,10-hexahydropyrano[2,3-f]chromene (Compound I-9b)

(R)- and (S)-3-(2,4-dihydroxyphenyl)-8,8-dimethyl-2,3,4,8,9,10-hexahydropyrano[2,3-f]chromenes with >96% ee were synthesized by using 3-(2-benzyloxy-4-dihydroxyphenyl)-8,8-dimethyl-2,8-dihydropyrano[2,3-f]chromene (Compound 5-11) synthesized in Preparation Example 11 and the same method as in Synthesis Example 1, respectively, and ¹H-NMR, ¹³C-NMR, and optical rotation results for the obtained Compounds are as follows.

¹H-NMR (DMSO-d6): 9.372 (b, 1H), 9.117 (b, 1H), 6.854 (d, 1H, J=8.4 Hz), 6.774 (d, 1H, J=8.4 Hz), 6.321 (d, 1H, J=2.4 Hz), 6.233 (d, 1H, J=8.4 Hz), 6.183 (dd, 1H, J=8.4, 2.4 Hz), 4.226 (m, 1H, J=10.4, 2.8, 20 Hz), 3.894 (t, 1H, J=10.4 Hz), 3.288 (m, 1H), 2.897 (dd, 1H, J=15.6, 11.6 Hz), 2.673 (ddd, 1H, J=15.6 Hz), 2.520 (t, 2H, J=6.8 Hz), 1.698 (t, 2H, J=6.8 Hz), 1.233 (s, 6H).

¹³C-NMR (DMSO-d6): 156.832, 155.862, 152.311, 151.702, 127.543, 127.368, 117.543, 112.893, 108.621, 108.464, 106.286, 102.499, 73.216, 69.717, 31.705, 30.978, 30.132, 26.442, 26.249, 16.839.

13C-NMR (CDCl3): 155.094, 154.575, 152.696, 152.038, 128.285, 127.498, 120.023, 112.956, 109.343, 107.765, 103.055, 73.881, 70.000, 32.285, 31.619, 30.477, 26.783, 26.403, 17.103.

Optical Rotation Data

R-enantiomer—[α]$_D^{20}$: −7.0° (c=0.025, ethanol); and

S-enantiomer—[α]$_D^{20}$: +7.9° (c=0.025, ethanol).

Synthesis Example 6: Preparation of (R)-3-(2-hydroxy-4-ethylphenyl)-8,8-dimethyl-2,3,4,8,9,10-hexahydropyrano[2,3-f]chromene (Compound I-13a) and (S)-3-(2-hydroxy-4-ethylphenyl)-8,8-dimethyl-2,3,4,8,9,10-hexahydropyrano[2,3-f]chromene (Compound I-13b)

(R)- and (S)-3-(2-benzyloxy-4-ethylphenyl)-8,8-dimethyl-2,3,4,8,9,10-hexahydropyrano[2,3-f]chromenes (Compounds 6-13a and 6-13b) were obtained by using 3-(2-benzyloxy-4-ethylphenyl)-8,8-dimethyl-2,8-dihydropyrano[2,3-f]chromene (Compound 5-18) synthesized in Preparation Example 18 and the method in Synthesis Example 1-1, respectively. ¹H-NMR and ¹³C-NMR results for the obtained Compounds are as follows.

In addition, (R)- and (S)-3-(2-hydroxy-4-ethylphenyl)-8,8-dimethyl-2,3,4,8,9,10-hexahydropyrano[2,3-f]chromenes with >96% ee were synthesized from (R)- and (S)-3-(2-benzyloxy-4-ethylphenyl)-8,8-dimethyl-2,3,4,8,9,10-hexahydropyrano[2,3-f]chromenes (Compounds 6-13a and 6-13b), respectively, by using the same method as in Synthesis Example 1-2, and ¹H-NMR, ¹³C-NMR, and optical rotation results for the obtained Compounds are as follows.

¹H-NMR (CDCl3): 7.28~7.45 (m, 5H), 7.063 (d, 1H, J=8.0 Hz), 6.827 (d, 1H, J=8.0 Hz), 6.817 (s, 1H), 6.906 (d, 1H, J=8.0 Hz), 6.376 (d, 1H, J=8.0 Hz), 5.104 (s, 2H), 4.395 (m, 1H, J=10.4, 3.6, 2.0 Hz), 4.024 (t, 1H, J=10.4 Hz), 3.710 (m, 1H), 3.004 (dd, 1H, J=15.6, 11.2 Hz), 2.876 (m, 1H, J=15.6, 5.2, 1.6 Hz), 2.650 (t, 2H, J=7.2 Hz), 2.632 (t, 2H, J=7.2 Hz), 1.763 (t, 2H, J=7.2 Hz), 1.323 (s, 3H), 1.313 (s, 3H), 1.226 (t, 2H, J=7.6 Hz).

¹³C-NMR (CDCl3): 156.350, 152.801, 152.217, 144.082, 137.160, 128.558, 127.778, 127.436, 127.331, 127.159, 127.107, 120.322, 112.897, 111.702, 109.250, 109.147, 73.611, 70.132, 70.015, 32.328, 31.619, 30.780, 28.802, 26.793, 26.488, 17.133, 15.483.

Synthesis Example 7: Preparation of (R)-3-(2-hydroxy-4-propylphenyl)-8,8-dimethyl-2,3,4,8,9,10-hexahydropyrano[2,3-f]chromene (Compound I-14a) and (S)-3-(2-hydroxy-4-propylphenyl)-8,8-dimethyl-2,3,4,8,9,10-hexahydropyrano[2,3-f]chromene (Compound I-14b)

(R)- and (S)-3-(2-benzyloxy-4-propylphenyl)-8,8-dimethyl-2,3,4,8,9,10-hexahydropyrano[2,3-f]chromenes (Compounds 6-14a and 6-14b) were synthesized by using 3-(2-benzyloxy-4-propylphenyl)-8,8-dimethyl-2,8-dihydropyrano[2,3-f]chromene (Compound 5-21) synthesized in Preparation Example 21 and the same method as in Synthesis Example 1-1, respectively. ¹H-NMR and ¹³C-NMR results for the obtained Compounds are as follows.

¹H-NMR (CDCl3): 7.28~7.45 (m, 5H), 7.052 (d, 1H, J=8.0 Hz), 6.828 (d, 1H, J=8.0 Hz), 6.791 (s, 1H), 6.784 (d, 1H, J=8.0 Hz), 6.375 (d, 1H, J=8.0 Hz), 5.102 (s, 2H), 4.395 (m, 1H, J=10.4, 3.6, 2.0 Hz), 4.023 (t, 1H, J=10.4 Hz), 3.713 (m, 1H), 3.003 (dd, 1H, J=15.6, 11.2 Hz), 2.876 (m, 1H, J=15.6, 5.2, 1.6 Hz), 2.632 (t, 2H, J=6.8 Hz), 2.554 (t, 2H, J=7.6 Hz), 1.766 (t, 2H, J=6.8 Hz), 1.626 (m, 2H, J=7.6 Hz), 1.325 (s, 3H), 1.315 (s, 3H), 0.937 (t, 2H, J=7.6 Hz).

¹³C-NMR (CDCl3): 156.242, 152.786, 152.210, 142.542, 137.154, 128.549, 127.766, 127.435, 127.295, 127.154, 126.979, 120.981, 112.917, 112.244, 109.247, 109.128, 73.617, 70.139, 69.992, 38.015, 32.319, 31.605, 30.779, 26.793, 26.481, 24.489, 17.132, 13.892.

In addition, 10 g of (R)-3-(2-hydroxy-4-propylphenyl)-8,8-dimethyl-2,3,4,8,9,10-hexahydropyrano[2,3-f]chromene and 10 g of (S)-3-(2-hydroxy-4-propylphenyl)-8,8-dimethyl-2,3,4,8,9,10-hexahydropyrano[2,3-f]chromene (>96% ee) were synthesized from (R)- and (S)-3-(2-benzyloxy-4-propylphenyl)-8,8-dimethyl-2,3,4,8,9,10-hexahydropyrano[2,3-f]chromenes (Compounds 6-14a and 6-14b), respectively, by using the same method as in Synthesis Example 1-2, and ¹H-NMR, ¹³C-NMR, and optical rotation results for the obtained Compounds are as follows.

¹H-NMR (CDCl3): 7.029 (d, 1H, J=8.0 Hz), 6.842 (d, 1H, J=8.0 Hz), 6.755 (d, 1H, J=8.0 Hz), 6.597 (s, 1H), 6.390 (d,

1H, J=8.4 Hz), 4.804 (s, 1H), 4.423 (m, 1H, J=10.4, 2.4 Hz), 4.046 (t, 1H, J=10.4 Hz), 3.537 (m, 1H), 3.042 (dd, 1H, J=15.6, 11.2 Hz), 2.886 (m, 1H), 2.652 (m, 2H), 2.518 (t, 2H, J=7.6 Hz), 1.781 (t, 2H, J=6.8 Hz), 1.612 (m, 2H, J=7.2 Hz), 1.338 (s, 3H), 1.323 (s, 3H), 0.947 (t, 3H, J=7.2 Hz).

$^{13}$C-NMR (CDCl3): 153.296, 152.802, 152.143, 142.679, 127.463, 127.331, 124.838, 121.188, 115.572, 112.888, 109.322, 109.286, 73.749, 69.933, 37.502, 32.366, 32.149, 30.605, 26.809, 26.411, 24.276, 17.141, 13.846.

Optical Rotation Data

R-enantiomer—$[\alpha]_D^{20}$: −3.9° (c=0.025, ethanol); and

S-enantiomer—$[\alpha]_D^{20}$: +2.4° (c=0.025, ethanol).

When the methods disclosed in the Preparation Examples, the Examples, and the Synthesis Examples are used, it is possible to simply prepare a 3-phenyl-2,3,4,8,9,10-hexahydropyrano[2,3-f]chromene derivative, or an optical isomer thereof from a 3-phenyl-2,8-dihydropyrano[2,3-f]chromene derivative through the hydrogen addition reaction and the de-protecting process.

From the foregoing, the present invention has been reviewed mainly based on the preferred examples thereof. A person with ordinary skill in the art to which the present invention pertains will be able to understand that the present invention may be implemented in a modified form without departing from the essential characteristics of the present invention. Therefore, the disclosed examples should be considered not from a restrictive viewpoint, but from an explanatory viewpoint. The scope of the present invention is defined not in the above-described explanation, but in the claims, and it should be interpreted that all the differences within a range equivalent thereto are included in the present invention.

The invention claimed is:

1. A method for synthesizing a 3-phenyl-2,3,4,8,9,10-hexahydropyrano[2,3-f]chromene derivative of Chemical Formula (I), the method comprising:

a) coupling a Compound represented by Chemical Formula 1 with a Compound represented by Chemical Formula 2 to form a Compound of Chemical Formula 3;

b) reducing the Compound of Chemical Formula 3 to form a Compound of Chemical Formula 4; and c) cyclizing the Compound of Chemical Formula 4 to form a Compound of Chemical Formula 5:

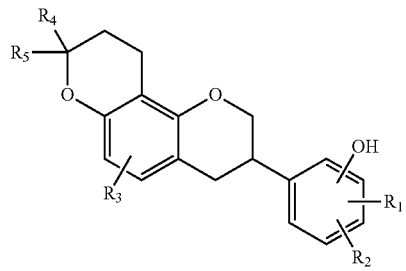

(I)

Reaction Formula I

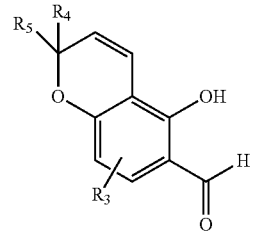

Chemical Formula 1

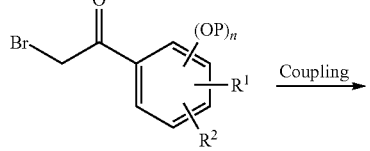

Chemical Formula 2

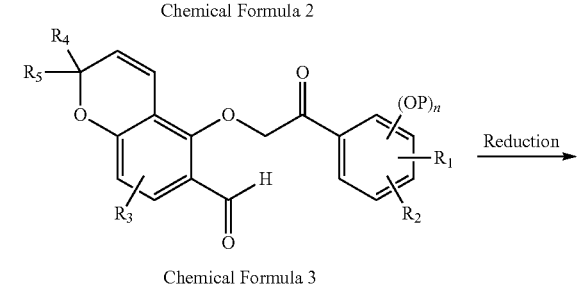

Chemical Formula 3

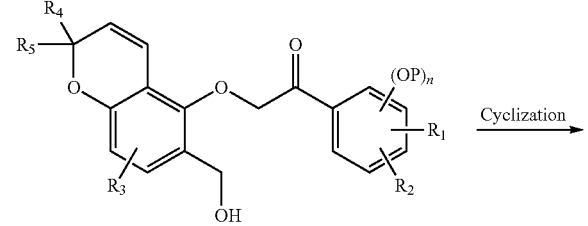

Chemical Formula 4

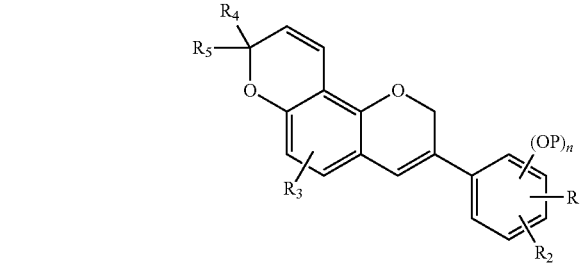

Chemical Formula 5 wherein, $R_1$ and $R_2$ are each independently hydrogen atom; hydroxy group; straight or branched $C_1$ to $C_6$ alkyl group unsubstituted or substituted with halogen atom, straight or branched $C_1$ to $C_5$ alkyl group, straight or branched $C_1$ to $C_5$ alkoxy group, or straight or branched $C_1$ to $C_3$ thioalkyl group; halogen atom; straight or branched $C_1$ to $C_6$ alkoxy group unsubstituted or substituted with halogen atom, straight or branched $C_1$ to $C_5$ alkyl group, straight or branched $C_1$ to $C_5$ alkoxy group, or straight or branched $C_1$ to $C_3$ thioalkyl group; straight or branched $C_1$ to $C_4$ thioalkyl group unsubstituted or substituted with halogen atom, straight or branched $C_1$ to $C_5$ alkyl group, straight or branched $C_1$ to $C_5$ alkoxy group, or straight or branched $C_1$ to $C_3$ thioalkyl group; allyloxy group unsubstituted or substituted with halogen atom, straight or branched $C_1$ to $C_5$ alkyl group, straight or branched $C_1$ to $C_5$ alkoxy group, or straight or branched $C_1$ to $C_3$ thioalkyl group; or aryloxy group unsubstituted or substituted with halogen atom, straight or branched $C_1$ to $C_5$ alkyl group, straight or branched $C_1$ to $C_5$ alkoxy group, or straight or branched $C_1$ to $C_3$ thioalkyl group;

$R_3$ is hydrogen atom or $C_1$ to $C_2$ alkyl group or $C_1$ to $C_2$ alkoxy group;

$R_4$ and $R_5$ are each independently hydrogen atom or $C_1$ to $C_6$ alkyl group;

P is a protecting group selected from straight or branched $C_1$ to $C_4$ alkyl group unsubstituted or substituted with halogen atom, straight or branched $C_1$ to $C_5$ alkyl group, straight or branched $C_1$ to $C_5$ alkoxy group, or straight or branched $C_1$ to $C_3$ thioalkyl group; benzyl group unsubstituted or substituted with halogen atom, straight or branched $C_1$ to $C_5$ alkyl group, straight or branched $C_1$ to $C_5$ alkoxy group, or straight or branched $C_1$ to $C_3$ thioalkyl group; allyl group unsubstituted or substituted with halogen atom, straight or branched $C_1$ to $C_5$ alkyl group, straight or branched $C_1$ to $C_5$ alkoxy group, or straight or branched $C_1$ to $C_3$ thioalkyl group; tert-butyldimethylsilyl group; tert-butyldiphenylsilyl group; methylphenylsilyl group; trimethylphenylsilyl group; $MeSO_2$ and $p-TsSO_2$;

n is 1 to 3; and two or more OPs are the same or different from each other.

2. The method of claim 1, further comprising:
reducing the Compound of Chemical Formula 5.

3. The method of claim 1, wherein the coupling in Step a) is performed under basic conditions.

4. The method of claim 3, wherein the basic conditions are created by adding one or more weak basic Compounds selected from a group consisting of sodium carbonate ($Na_2CO_3$), lithium carbonate ($Li_2CO_3$), potassium carbonate ($K_2CO_3$), sodium hydrogen carbonate ($NaHCO_3$), potassium hydrogen carbonate ($KHCO_3$), triethylamine, and pyridine.

5. The method of claim 1, wherein the reducing in Step b) is carried out by adding any one or more reducing agents selected from a group consisting of L-Selectride, N-Selectride, K-Selectride, and LS-Selectride.

6. The method of claim 5, wherein the reducing agent is added at −10° C. or less.

7. The method of claim 1, wherein the cyclizing in Step c) includes the following steps:
i) dissolving the Compound of Chemical Formula 4 in acetonitrile and adding triphenylphosphonium bromide ($Ph_3P.HBr$) thereinto;
ii) concentrating the resulting product in Step i); and
iii) dissolving the concentrate obtained in Step ii) and adding sodium ethoxide (NaOEt) thereinto.

8. A Compound represented by the following Chemical Formula 3, or a solvate thereof:

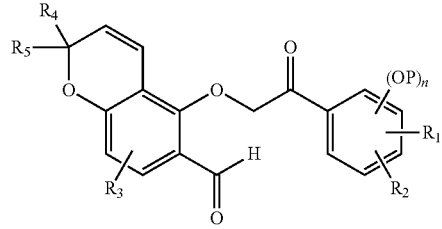

Chemical Formula 3 wherein, $R_1$ and $R_2$ are each independently hydrogen atom; hydroxy group; straight or branched $C_1$ to $C_6$ alkyl group unsubstituted or substituted with halogen atom, straight or branched $C_1$ to $C_5$ alkyl group, straight or branched $C_1$ to $C_5$ alkoxy group, or straight or branched $C_1$ to $C_3$ thioalkyl group; halogen atom; straight or branched $C_1$ to $C_6$ alkoxy group unsubstituted or substituted with halogen atom, straight or branched $C_1$ to $C_5$ alkyl group, straight or branched $C_1$ to $C_5$ alkoxy group, or straight or branched $C_1$ to $C_3$ thioalkyl group; straight or branched $C_1$ to $C_4$ thioalkyl group unsubstituted or substituted with halogen atom, straight or branched $C_1$ to $C_5$ alkyl group, straight or branched $C_1$ to $C_5$ alkoxy group, or straight or branched $C_1$ to $C_3$ thioalkyl group; allyloxy group unsubstituted or substituted with halogen atom, straight or branched $C_1$ to $C_5$ alkyl group, straight or branched $C_1$ to $C_5$ alkoxy group, or straight or branched $C_1$ to $C_3$ thioalkyl group; or aryloxy group unsubstituted or substituted with halogen atom, straight or branched $C_1$ to $C_5$ alkyl group, straight or branched $C_1$ to $C_5$ alkoxy group, or straight or branched $C_1$ to $C_3$ thioalkyl group;

$R_3$ is hydrogen atom or $C_1$ to $C_2$ alkyl group or $C_1$ to $C_2$ alkoxy group;

$R_4$ and $R_5$ are each independently hydrogen atom or $C_1$ to $C_6$ alkyl group;

P is a protecting group selected from straight or branched $C_1$ to $C_4$ alkyl group unsubstituted or substituted with halogen atom, straight or branched $C_1$ to $C_5$ alkyl group, straight or branched $C_1$ to $C_5$ alkoxy group, or straight or branched $C_1$ to $C_3$ thioalkyl group; benzyl group unsubstituted or substituted with halogen atom, straight or branched $C_1$ to $C_5$ alkyl group, straight or branched $C_1$ to $C_5$ alkoxy group, or straight or branched $C_1$ to $C_3$ thioalkyl group; allyl group unsubstituted or substituted with halogen atom, straight or branched $C_1$ to $C_5$ alkyl group, straight or branched $C_1$ to $C_5$ alkoxy group, or straight or branched $C_1$ to $C_3$ thioalkyl group; tert-butyldimethylsilyl group; tert-butyldiphenylsilyl group; methylphenylsilyl group; trimethylphenylsilyl group; $MeSO_2$ and $p-TsSO_2$;

n is 1 to 3; and two or more OPs are the same or different from each other.

9. A Compound represented by the following Chemical Formula 4, or a solvate thereof:

Chemical Formula 4

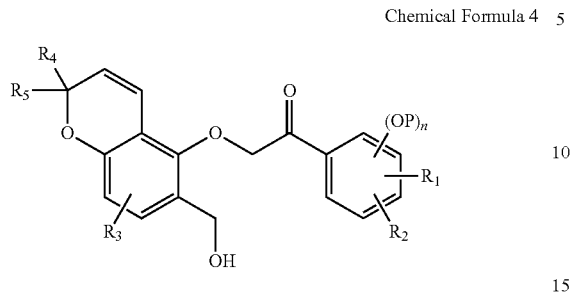

wherein, $R_1$ and $R_2$ are each independently hydrogen atom; hydroxy group; straight or branched $C_1$ to $C_6$ alkyl group unsubstituted or substituted with halogen atom, straight or branched $C_1$ to $C_5$ alkyl group, straight or branched $C_1$ to $C_5$ alkoxy group, or straight or branched $C_1$ to $C_3$ thioalkyl group; halogen atom; straight or branched $C_1$ to $C_6$ alkoxy group unsubstituted or substituted with halogen atom, straight or branched $C_1$ to $C_5$ alkyl group, straight or branched $C_1$ to $C_5$ alkoxy group, or straight or branched $C_1$ to $C_3$ thioalkyl group; straight or branched $C_1$ to $C_4$ thioalkyl group unsubstituted or substituted with halogen atom, straight or branched $C_1$ to $C_5$ alkyl group, straight or branched $C_1$ to $C_5$ alkoxy group, or straight or branched $C_1$ to $C_3$ thioalkyl group; allyloxy group unsubstituted or substituted with halogen atom, straight or branched $C_1$ to $C_5$ alkyl group, straight or branched $C_1$ to $C_5$ alkoxy group, or straight or branched $C_1$ to $C_3$ thioalkyl group; or aryloxy group unsubstituted or substituted with halogen atom, straight or branched $C_1$ to $C_5$ alkyl group, straight or branched $C_1$ to $C_5$ alkoxy group, or straight or branched $C_1$ to $C_3$ thioalkyl group;

$R_3$ is hydrogen atom or $C_1$ to $C_2$ alkyl group or $C_1$ to $C_2$ alkoxy group;

$R_4$ and $R_5$ are each independently hydrogen atom or $C_1$ to $C_6$ alkyl group;

P is a protecting group selected from straight or branched $C_1$ to $C_4$ alkyl group unsubstituted or substituted with halogen atom, straight or branched $C_1$ to $C_5$ alkyl group, straight or branched $C_1$ to $C_5$ alkoxy group, or straight or branched $C_1$ to $C_3$ thioalkyl group; benzyl group unsubstituted or substituted with halogen atom, straight or branched $C_1$ to $C_5$ alkyl group, straight or branched $C_1$ to $C_5$ alkoxy group, or straight or branched $C_1$ to $C_3$ thioalkyl group; allyl group unsubstituted or substituted with halogen atom, straight or branched $C_1$ to $C_5$ alkyl group, straight or branched $C_1$ to $C_5$ alkoxy group, or straight or branched $C_1$ to $C_3$ thioalkyl group; tert-butyldimethylsilyl group; tert-butyldiphenylsilyl group; methylphenylsilyl group; trimethylphenylsilyl group; $MeSO_2$ and p-$TsSO_2$;

n is 1 to 3; and two or more OPs are the same or different from each other.

10. A method for synthesizing an optical isomer of a 3-phenyl-2,3,4,8,9,10-hexahydropyrano[2,3-]chromene derivative of Chemical Formula (I), the method comprising:

A) coupling a Compound represented by Chemical Formula 1 with a Compound represented by Chemical Formula 2 to form a Compound of Chemical Formula 3;

B) reducing the Compound of Chemical Formula 3 to form a Compound of Chemical Formula 4;

C) cyclizing the Compound of Chemical Formula 4 to form a Compound of Chemical Formula 5; and D) subjecting the Compound represented by Chemical Formula 5 to an asymmetric hydrogenation reaction to form an optical isomer Compound of Chemical Formula 6a (R-form) or 6b (S-form):

(I)

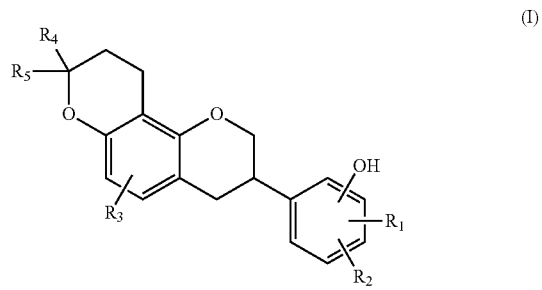

Reaction Formula 2

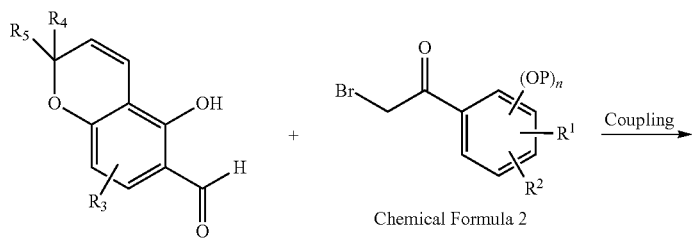

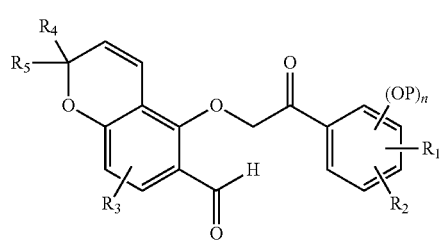

Chemical Formula 3

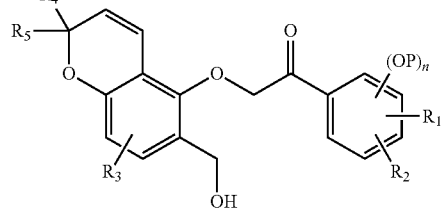

Chemical Formula 4

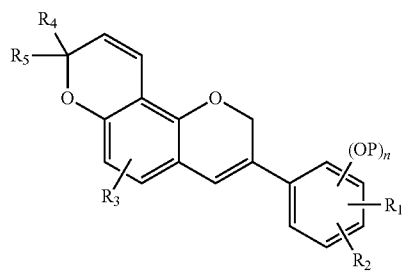

Chemical Formula 5

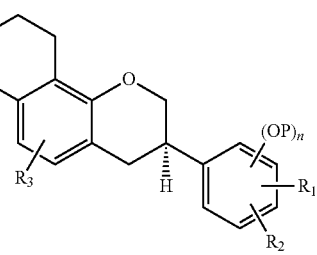

Chemical Formula 6a(R-form)

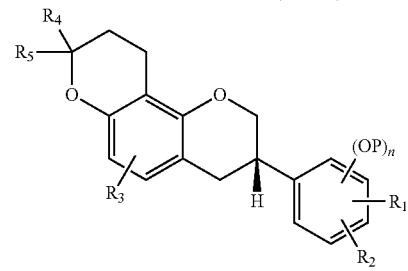

Chemical Formula 6b(S-form)

wherein, $R_1$ and $R_2$ are each independently hydrogen atom; hydroxy group; straight or branched $C_1$ to $C_6$ alkyl group unsubstituted or substituted with halogen atom, straight or branched $C_1$ to $C_5$ alkyl group, straight or branched $C_1$ to $C_5$ alkoxy group, or straight or branched $C_1$ to $C_3$ thioalkyl group; halogen atom; straight or branched $C_1$ to $C_6$ alkoxy group unsubstituted or substituted with halogen atom, straight or branched $C_1$ to $C_5$ alkyl group, straight or branched $C_1$ to $C_5$ alkoxy group, or straight or branched $C_1$ to $C_3$ thioalkyl group; straight or branched $C_1$ to $C_4$ thioalkyl group unsubstituted or substituted with halogen atom, straight or branched $C_1$ to $C_3$ alkyl group, straight or branched $C_1$ to $C_5$ alkoxy group, or straight or branched $C_1$ to $C_3$ thioalkyl group; allyloxy group unsubstituted or substituted with halogen atom, straight or branched $C_1$ to $C_5$ alkyl group, straight or branched $C_1$ to $C_5$ alkoxy group, or straight or branched $C_1$ to $C_3$ thioalkyl group; or aryloxy group unsubstituted or substituted with halogen atom, straight or branched $C_1$ to $C_5$ alkyl group, straight or branched $C_1$ to $C_5$ alkoxy group, or straight or branched $C_1$ to $C_3$ thioalkyl group;

$R_3$ is hydrogen atom or $C_1$ to $C_2$ alkyl group or $C_1$ to $C_2$ alkoxy group;

$R_4$ and $R_5$ are each independently hydrogen atom or $C_1$ to $C_6$ alkyl group;

P is a protecting group selected from straight or branched $C_1$ to $C_4$ alkyl group unsubstituted or substituted with halogen atom, straight or branched $C_1$ to $C_5$ alkyl group, straight or branched $C_1$ to $C_5$ alkoxy group, or straight or branched $C_1$ to $C_3$ thioalkyl group; benzyl group unsubstituted or substituted with halogen atom, straight or branched $C_1$ to $C_5$ alkyl group, straight or branched $C_1$ to $C_5$ alkoxy group, or straight or branched $C_1$ to $C_3$ thioalkyl group; allyl group unsubstituted or substituted with halogen atom, straight or branched $C_1$ to $C_5$ alkyl group, straight or branched $C_1$ to $C_5$ alkoxy group, or straight or branched $C_1$ to $C_3$ thioalkyl group; tert-butyldimethylsilyl group; tert-butyldiphenylsilyl group; methylphenylsilyl group; trimethylphenylsilyl group; $MeSO_2$ and $p-TsSO_2$;

n is 1 to 3; and two or more OPs are the same or different from each other.

11. The method of claim 10, wherein the coupling in Step A) is performed under basic conditions.

12. The method of claim 11, wherein the basic conditions are created by adding one or more weak basic Compounds selected from a group consisting of sodium carbonate ($Na_2CO_3$), lithium carbonate ($Li_2CO_3$), potassium carbonate ($K_2CO_3$), sodium hydrogen carbonate ($NaHCO_3$), potassium hydrogen carbonate ($KHCO_3$), triethylamine, and pyridine.

13. The method of claim 10, wherein the reducing in Step B) is carried out by adding any one or more reducing agents selected from a group consisting of L-Selectride, N-Selectride, K-Selectride, and LS-Selectride.

14. The method of claim 13, wherein the reducing agent is added at −10° C. or less.

15. The method of claim 10, wherein the cyclization reaction in Step C) includes the following steps:
  i) dissolving the Compound of Chemical Formula 4 in acetonitrile and adding triphenylphosphonium bromide ($Ph_3P \cdot HBr$) thereinto;
  ii) concentrating the resulting product in Step i); and
  iii) dissolving the concentrate obtained in Step ii) and adding sodium ethoxide (NaOEt) thereinto.

16. The method of claim 10, wherein the asymmetric hydrogenation reaction in Step D) is a reaction caused by adding a chiral ligand.

17. The method of claim 16, wherein the chiral ligand is any one selected from the group consisting of a phospholane ligand, a SimplePHOX ligand, a PHOX ligand, and UbaPHOX.

* * * * *